US011793781B2

(12) United States Patent
Chandraratna et al.

(10) Patent No.: US 11,793,781 B2
(45) Date of Patent: *Oct. 24, 2023

(54) AUTOIMMUNE DISORDER TREATMENT USING RXR AGONISTS

(71) Applicants: Io Therapeutics, Inc., Spring, TX (US); Trustees of Dartmouth College, Hanover, NH (US)

(72) Inventors: Roshantha A. Chandraratna, San Juan Capistrano, CA (US); Ethan Dmitrovsky, Hanover, NH (US); Elizabeth Nowak, West Lebanon, NH (US); Randolph Noelle, Plainfield, NH (US)

(73) Assignees: Io Therapeutics, Inc., Spring, TX (US); Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,657

(22) Filed: Jan. 27, 2022

(65) Prior Publication Data
US 2022/0151964 A1 May 19, 2022

Related U.S. Application Data

(63) Continuation of application No. 17/126,787, filed on Dec. 18, 2020, now Pat. No. 11,246,845, which is a continuation of application No. 16/742,616, filed on Jan. 14, 2020, which is a continuation of application No. 16/228,217, filed on Dec. 20, 2018, now Pat. No. 10,945,976, which is a continuation of application No. 15/852,580, filed on Dec. 22, 2017, now Pat. No. 10,201,512, which is a continuation of application No. 15/341,969, filed on Nov. 2, 2016, now Pat. No. 10,285,960, which is a continuation of application No. 13/714,051, filed on Dec. 13, 2012, now abandoned.

(60) Provisional application No. 61/570,182, filed on Dec. 13, 2011.

(51) Int. Cl.
*A61K 31/192* (2006.01)
*A61K 31/216* (2006.01)
*A61K 31/201* (2006.01)
*A61K 31/353* (2006.01)
*A61K 31/343* (2006.01)
*A61K 31/47* (2006.01)
*A61K 31/4704* (2006.01)
*A61K 9/00* (2006.01)

(52) U.S. Cl.
CPC .......... *A61K 31/192* (2013.01); *A61K 9/0073* (2013.01); *A61K 31/201* (2013.01); *A61K 31/216* (2013.01); *A61K 31/343* (2013.01); *A61K 31/353* (2013.01); *A61K 31/47* (2013.01); *A61K 31/4704* (2013.01); *Y02A 50/30* (2018.01)

(58) Field of Classification Search
CPC .................................................... A61K 31/192
See application file for complete search history.

(56) References Cited

U.S. PATENT DOCUMENTS

| | | | |
|---|---|---|---|
| 4,756,911 | A | 7/1988 | Drost |
| 5,378,475 | A | 1/1995 | Smith |
| 5,455,265 | A | 10/1995 | Chandraratna |
| 5,466,861 | A | 11/1995 | Dawson et al. |
| 5,663,367 | A | 9/1997 | Vuligonda et al. |
| 5,675,033 | A | 10/1997 | Vuligonda et al. |
| 5,728,846 | A | 3/1998 | Vuligonda et al. |
| 5,739,338 | A | 4/1998 | Beard et al. |
| 5,763,635 | A | 6/1998 | Vuligonda et al. |
| 5,773,594 | A | 6/1998 | Johnson et al. |
| 5,776,699 | A | 7/1998 | Klein et al. |
| 5,780,647 | A | 7/1998 | Vuligonda et al. |
| 5,817,836 | A | 10/1998 | Vuligonda et al. |
| 5,856,490 | A | 1/1999 | Teng |
| 5,877,207 | A | 3/1999 | Klein et al. |
| 5,917,082 | A | 6/1999 | Vuligonda et al. |
| 5,919,970 | A | 7/1999 | Song et al. |
| 5,952,345 | A | 9/1999 | Klein et al. |
| 5,958,954 | A | 9/1999 | Klein et al. |
| 5,965,606 | A | 10/1999 | Teng |
| 5,998,655 | A | 12/1999 | Vuligonda et al. |

(Continued)

FOREIGN PATENT DOCUMENTS

| EP | 2322147 A1 | 5/2011 |
|---|---|---|
| EP | 2556827 A1 | 2/2013 |

(Continued)

OTHER PUBLICATIONS

Inoue et al., Rexinoids isolated from Sophora tonkinensis with a gene expression profile distinct from the synthetic rexinoid bexarotene. J. Nat. Prod. 77:1670-1677 (2014).

(Continued)

*Primary Examiner* — Yong S. Chong
(74) *Attorney, Agent, or Firm* — K&L Gates LLP; Louis C. Cullman; Michelle Glasky Bergman

(57) ABSTRACT

The present specification provides RXR agonist compounds, compositions comprising such RXR agonists, and methods using such compounds and compositions to treat an autoimmune disorder, inflammation associated with an autoimmune disorder and/or a transplant rejection as well as use of such RXR agonists to manufacture a medicament and use of such compounds and compositions to treat an autoimmune disorder, inflammation associated with an autoimmune disorder and/or a transplant rejection.

23 Claims, 4 Drawing Sheets

(56) References Cited

U.S. PATENT DOCUMENTS

| | | |
|---|---|---|
| 6,008,204 A | 12/1999 | Klein et al. |
| 6,048,873 A | 1/2000 | Vasudevan et al. |
| 6,034,242 A | 3/2000 | Vuligonda et al. |
| 6,037,488 A | 3/2000 | Song et al. |
| 6,043,381 A | 3/2000 | Vuligonda et al. |
| 6,063,768 A | 5/2000 | First |
| 6,087,505 A | 7/2000 | Vuligonda et al. |
| 6,090,810 A | 7/2000 | Klein et al. |
| 6,114,533 A | 9/2000 | Vuligonda et al. |
| 6,117,987 A | 9/2000 | Johnson et al. |
| 6,147,224 A | 11/2000 | Vuligonda et al. |
| 6,187,750 B1 | 2/2001 | Chein |
| 6,211,385 B1 | 4/2001 | Vuligonda et al. |
| 6,218,128 B1 | 4/2001 | Klein et al. |
| 6,225,494 B1 | 5/2001 | Song et al. |
| 6,228,848 B1 | 5/2001 | Klein et al. |
| 6,235,923 B1 | 5/2001 | Song et al. |
| 6,313,163 B1 | 11/2001 | Vuligonda et al. |
| 6,313,168 B1 | 11/2001 | Pacifici et al. |
| 6,387,950 B2 | 5/2002 | Nehme |
| 6,403,638 B1 | 6/2002 | Vuligonda et al. |
| 6,521,624 B1 | 2/2003 | Klein et al. |
| 6,521,641 B1 | 2/2003 | Klein et al. |
| 6,538,149 B1 | 3/2003 | Vuligonda et al. |
| 6,555,690 B2 | 4/2003 | Johnson et al. |
| 6,610,744 B2 | 8/2003 | Teng et al. |
| 6,630,463 B2 | 10/2003 | Kikuchi et al. |
| 6,653,483 B1 | 11/2003 | Johnson et al. |
| 6,720,423 B2 | 4/2004 | Vasudevan et al. |
| 6,720,425 B2 | 4/2004 | Johnson et al. |
| 6,776,984 B1 | 8/2004 | Schwartz |
| 6,818,775 B2 | 11/2004 | Johnson et al. |
| 6,942,980 B1 | 9/2005 | Klein et al. |
| 7,048,946 B1 | 5/2006 | Wong |
| 7,105,566 B2 | 9/2006 | Chandraratna et al. |
| 7,166,726 B2 | 1/2007 | Vuligonda et al. |
| 8,101,662 B2 | 1/2012 | Chandraratna |
| 9,308,186 B2 | 4/2016 | Chandraratna |
| 9,655,872 B2 | 5/2017 | Chandraratna |
| 9,717,702 B2 | 8/2017 | Chandraratna |
| 10,039,731 B2 | 8/2018 | Chandraratna |
| 10,188,618 B2 | 1/2019 | Chandraratna |
| 10,590,059 B2 | 3/2020 | Chandraratna et al. |
| 10,596,133 B2 | 3/2020 | Chandraratna |
| 10,806,713 B2 | 10/2020 | Chandraratna et al. |
| 10,835,507 B2 | 11/2020 | Chandraratna et al. |
| 10,857,117 B2 | 12/2020 | Chandraratna et al. |
| 10,966,950 B2 | 4/2021 | Sanders et al. |
| 10,973,791 B2 | 4/2021 | Chandraratna et al. |
| 10,980,759 B2 | 4/2021 | Chandraratna et al. |
| 11,065,219 B2 | 7/2021 | Chandraratna et al. |
| 2001/0037025 A1 | 11/2001 | Murray |
| 2002/0156022 A1 | 10/2002 | Edwards et al. |
| 2002/0156054 A1 | 10/2002 | Klein et al. |
| 2002/0173631 A1 | 11/2002 | Johnson et al. |
| 2002/0193403 A1 | 12/2002 | Yuan et al. |
| 2003/0013766 A1 | 1/2003 | Lamph et al. |
| 2003/0077664 A1 | 4/2003 | Zhao et al. |
| 2003/0130341 A1 | 7/2003 | Li et al. |
| 2003/0144330 A1 | 7/2003 | Spiegelman |
| 2003/0219832 A1 | 11/2003 | Klein et al. |
| 2004/0005304 A1* | 1/2004 | Brudnak ............ A61K 45/06 514/23 |
| 2004/0049072 A1 | 3/2004 | Ardecky |
| 2004/0147611 A1 | 7/2004 | Yuan et al. |
| 2004/0037025 A1 | 11/2004 | Murray et al. |
| 2005/0004213 A1 | 1/2005 | Sinha et al. |
| 2005/0171151 A1 | 8/2005 | Yuan et al. |
| 2005/0181017 A1 | 8/2005 | Hughes |
| 2005/0244464 A1 | 11/2005 | Hughes |
| 2006/0286127 A1 | 12/2006 | Van Schaack et al. |
| 2007/0054882 A1 | 3/2007 | Klein et al. |
| 2007/0077652 A1 | 4/2007 | Peled et al. |
| 2007/0078129 A1 | 4/2007 | Lagu et al. |
| 2007/0122476 A1 | 5/2007 | Hanshew |
| 2007/0185055 A1* | 8/2007 | Jiang ................ A61K 31/215 514/432 |
| 2007/0265449 A1 | 11/2007 | Vuligonda et al. |
| 2009/0004291 A1 | 1/2009 | Song |
| 2009/0136470 A1 | 5/2009 | Hilde et al. |
| 2009/0203720 A1 | 8/2009 | Zhao et al. |
| 2009/0209601 A1 | 8/2009 | Nagpal et al. |
| 2009/0227674 A1 | 9/2009 | Richon et al. |
| 2010/0112079 A1 | 5/2010 | Mousa et al. |
| 2010/0298434 A1 | 11/2010 | Rouillard |
| 2011/0008437 A1 | 1/2011 | Altman |
| 2012/0115912 A1 | 5/2012 | Landreth |
| 2012/0238623 A1 | 9/2012 | Chandraratna |
| 2012/0309833 A1 | 12/2012 | Wagner et al. |
| 2013/0190395 A1 | 7/2013 | Chandraratna et al. |
| 2014/0235676 A1 | 8/2014 | Landreth |
| 2014/0286973 A1 | 9/2014 | Powell, Jr. |
| 2015/0038585 A1 | 2/2015 | Chandraratna et al. |
| 2015/0196517 A1 | 7/2015 | Chandraratna et al. |
| 2015/0342917 A1 | 12/2015 | Chandraratna et al. |
| 2016/0263189 A1 | 9/2016 | Burstein |
| 2017/0056348 A1 | 3/2017 | Chandraratna et al. |
| 2017/0119713 A1 | 5/2017 | Chandraratna et al. |
| 2017/0119714 A1 | 5/2017 | Chandraratna et al. |
| 2018/0064670 A1 | 3/2018 | Chandraratna et al. |
| 2018/0116985 A1 | 5/2018 | Chandraratna et al. |
| 2018/0263939 A1 | 9/2018 | Chandraratna et al. |
| 2018/0318241 A1 | 11/2018 | Chandraratna et al. |
| 2018/0369181 A1 | 12/2018 | Chandraratna et al. |
| 2019/0083441 A1 | 3/2019 | Chandraratna et al. |
| 2019/0117603 A1 | 4/2019 | Chandraratna et al. |
| 2019/0125705 A1 | 5/2019 | Chandraratna et al. |
| 2019/0201358 A1 | 7/2019 | Chandraratna et al. |
| 2019/0231726 A1 | 8/2019 | Chandraratna et al. |
| 2019/0298678 A1 | 10/2019 | Chandraratna et al. |
| 2019/0365681 A1 | 12/2019 | Chandraratna et al. |
| 2019/0381022 A1 | 12/2019 | Chandraratna et al. |
| 2020/0155488 A1 | 5/2020 | Chandraratna et al. |
| 2020/0155489 A1 | 5/2020 | Chandraratna et al. |
| 2020/0163915 A1 | 5/2020 | Chandraratna et al. |
| 2020/0170985 A1 | 6/2020 | Chandraratna et al. |
| 2020/0190008 A1 | 6/2020 | Chandraratna et al. |
| 2020/0390736 A1 | 12/2020 | Sanders et al. |
| 2021/0077445 A1 | 3/2021 | Chandraratna et al. |
| 2021/0128503 A1 | 5/2021 | Chandraratna et al. |
| 2021/0128504 A1 | 5/2021 | Chandraratna et al. |
| 2021/0161874 A1 | 6/2021 | Chandraratna et al. |
| 2021/0205243 A1 | 7/2021 | Chandraratna et al. |
| 2022/0117922 A1 | 4/2022 | Chandraratna et al. |
| 2022/0143000 A1 | 5/2022 | Chandraratna et al. |

FOREIGN PATENT DOCUMENTS

| | | |
|---|---|---|
| JP | 2010-280585 A | 12/2010 |
| WO | 1994/012880 A2 | 6/1994 |
| WO | 1994/014777 | 7/1994 |
| WO | 1996/039374 A1 | 12/1996 |
| WO | 1997/009297 A2 | 3/1997 |
| WO | 1999/008992 A1 | 2/1999 |
| WO | 1999/033821 A1 | 7/1999 |
| WO | 1999/063980 A1 | 12/1999 |
| WO | 2000/020370 A1 | 4/2000 |
| WO | 2001/007028 A2 | 2/2001 |
| WO | 2002/089781 A2 | 11/2002 |
| WO | 2002/089842 | 11/2002 |
| WO | 2003/027090 A2 | 4/2003 |
| WO | 2003/062369 | 7/2003 |
| WO | 2003/078567 | 9/2003 |
| WO | 2003/093257 A1 | 11/2003 |
| WO | 2003/101928 | 12/2003 |
| WO | 2004/046096 | 6/2004 |
| WO | 2005/013949 A2 | 2/2005 |
| WO | 2005/027895 A2 | 3/2005 |
| WO | 2007/022408 A2 | 2/2007 |
| WO | 2007/041076 A2 | 4/2007 |
| WO | 2007/041398 | 4/2007 |
| WO | 2008/157394 A2 | 12/2008 |
| WO | 2010/041149 A2 | 4/2010 |
| WO | 2010/041449 | 4/2010 |

(56) References Cited

FOREIGN PATENT DOCUMENTS

| | | |
|---|---|---|
| WO | 2010/132671 A1 | 11/2010 |
| WO | 2011/006157 A2 | 1/2011 |
| WO | 2013/020966 | 2/2013 |
| WO | 2013/090616 A1 | 6/2013 |
| WO | 2015/059632 A1 | 4/2015 |
| WO | 2015/066197 A2 | 5/2015 |
| WO | 2016/144976 A1 | 9/2016 |
| WO | 2017/075610 | 5/2017 |
| WO | 2017/075612 A1 | 5/2017 |
| WO | 2017/155577 A1 | 9/2017 |
| WO | 2017/155578 A1 | 9/2017 |
| WO | 2019/046591 A1 | 3/2019 |
| WO | 2019/060600 A1 | 3/2019 |

OTHER PUBLICATIONS

"Intranasal medication delivery—brief overview of the concept." Intranasal.net. Accessed Feb. 24, 2017.

Io Therapeutics, Inc. Brochure for the Symposium on IRX4204 at the 11th International Conference on Alzheimer's and Parkinson's Diseases (2013).

Jassem et al., A randomized phase III trial comparing bexarotene/cisplatin/vinorelbine versus cisplatin/vinorelbine in chemotherapy-naïve-patients with advanced or metastatic non-small cell lung cancer (NSCLC). Journal of Clinical Oncology, 2005 ASCO Annual Meeting Proceedings, vol. 23, No. 16S, Part I of II (June 1 Supplement), Abstract 7024 (2005).

Johnson et al., Synthesis and biological activity of high-affinity retinoic acid receptor antagonists. Bioorganic & Medicinal Chemistry, vol. 7, No. 7, pp. 1321-1338 (1999).

Kagechika et al., Synthetic retinoids: recent developments concerning structure and clinical utility. Journal of Medicinal Chemistry, vol. 48, No. 19: 5875-5883, (2005).

Kawata et al., RXR partial agonist produced by side chain repositioning of alkoxy RXR full agonist retains antitype 2 diabetes activity without the adverse effects. J. Med. Chem. 58(2):912-926 (2015).

Kimura et al., IL-6: Regulator of Treg/Th 17 balance. Eur. J. Immunol., 40:1830-1835 (2010).

Kim et al., Immunopathogenesis and therapy of cutaneous T cell lymphoma. Science in Medicine, The JCI Textbook of Molecular Medicine. Editors Marks et al., p. 164 (2007).

Klein et al., Cardiovascular involvement in general medial conditions. Thyroid disease and the heart. Circulation, 116:1725-1735 (2007).

Klein et al., Identification and functional separation of retinoic acid receptor neutral antagonists and inverse agonists. The Journal of Biological Chemistry, vol. 271, No. 37, pp. 22692-22696, 1996.

Knol et al., Absence of modulation of CD4+CD25high regulatory T cells in CTCL patients treated with bexarotene. Experimental Dermatology, 19:e95-e102 (2010).

Kotani et al., A naturally occurring rexinoid, honokiol, can serve as a regulator of various retinoid X receptor heterodimers. Biol. Pharm. Bull. 35(1):1-9 (2012).

Laclair et al., Treatment with bexarotene, a compound that increases apolipoprotein-E, provides no cognitive benefit in mutant APP/PS1 mice, Molecular Neurodegeneration 8:18 (10pp) (2013).

Lampen et al., Effects of receptor-selective retinoids on CYP26 gene expression and metabolism of all-trans-retinoic acid in intestinal cells. Drug Metabolism & Disposition, vol. 29, No. 3, pp. 742-747 (2001).

Lefebvre et al., Retinoid X receptors: common heterodimerization partners with distinct functions. Trends Endocrinol. Metab. 21:676-683 (2010).

Levasque et al., Nur77 and retinoid X receptors: crucial factors in dopamine-related neuroadaptation. Trends in Neuroscience, vol. 30, No. 1, pp. 22-30 (2007).

Li et al., Distinct Mechanisms of Glucose Lowering by Specific Agonists for Peroxisomal Proliferator Activated Receptor gamma and Retinoic Acid X Receptors, Journal of Biological Chemistry 280(46):38317-38327, 2005.

Liu et al., Combination Therapy of Insulin-Like Growth Factor Binding Protein-3 and Retinoid X Receptor Ligands Synergize on Prostate Cancer Cell Apoptosis In vitro and In vivo. Clin Cancer Res, 11(13):4851-4856 (2005).

Lowenthal et al., The Ethics of Early Evidence—Preparing for a Possible Breakthrough in Alzheimer's Disease, N Engl J Med., 367(6):488-490 (2012).

Macchia et al., RXR receptor agonist suppression of thryoid function: central effects in the absence of thyroid hormone receptor. Am. J. Physiol. Endocrinol. Metab., vol. 283, pp. E326-E331 (2002).

Mangelsdorf et al., Characterization of three RXR genes that mediate the action of 9-cis retinoic acid. Genes and Development 6:329-344 (1992).

Marketwire 2012: IRX4204 as a Potential Disease-Modifying Treatment for Alzheimer's Disease.

Marks et al., Science in Medicine: The JCI textbook of Molecular Medicine, p. 164 (2007).

Martin et al., Induction of the fatty acid transport protein 1 and acyl-CoA synthase genes by dimer-selective rexinoids suggests that the peroxisome proliferator-activated receptor-retinoid X receptor heterodimer is their molecular target. JBC 275(17):12612-12618 (2000).

McFarland et al., Low dose bexarotene treatment rescues dopamine neurons and restores behavioral function in models of Parkinson's disease. ACS Chem. Neurosci. 4:1430-1438 (2013).

Migliore, Intranasal Delivery of GDNF for the Treatment of Parkinson's Disease. Doctoral Thesis, Pharmaceutical Sciences, Northeastern University, Boston, MA (2008).

Miller et al., Initial clinical trial of a selective retinoid X receptor ligand, LGD1069. J Clin Oncol., 15(2):790-795 (1997).

Monahan et al., Neuroinflammation and peripheral immune infiltration in Parkinson's disease: an autoimmune hypothesis. Cell Transplant, 17:363-372 (2008).

Morris & Burns, Insulin: An Emerging Treatment for Alzheimer's Disease Dementia? Curr. Neurol. Neurosci. Rep. 12(5):520-527 (2012).

Munhoz et al., Parkinson's disease and thyroid dysfunction. Parkinsonism & Related Disorders, 10(6):381-383 (2004).

National Multiple Sclerosis Society, Medications, accessed May 12, 2017, pp. 1-5.

Natrajan et al., Retinoid X receptor activation reverses age-related deficiencies in myelin debris phagocytosis and remyelination. Brain A Journal of Neurology, 138:3581-3597 (2015).

Nishimaki-Mogami et al., The RXR agonists PA024 and HX630 have different abilities to activate LXR/RXR and to induce ABCA1 expression in macrophage cell lines. Biochemical Pharmacology, 76: 1006-1013 (2008).

Ohsawa et al., Modification of the lipophilic domain of RXR agonists differentially influences activation of RXR heterodimers. ACS Med Chem Lett., 1:521-525 (2010).

Olson et al., Immunomodulation as a neuroprotective and therapeutic strategy for Parkinson's disease. Curr Opin Pharmacol 26:87-95 (2016).

Park et al., Salvage chemotherapy of gemcitabine, dexamethasone, and cisplatin (GDP) for patients with relapsed or refractory peripheral T-cell lymphomas: a consortium for improving survival of lymphoma (CISL) trial. Ann. Hematol., vol. 94, No. 11, pp. 1845-1851, see abstract (2015).

Perlmann et al., A novel pathway for vitamin A signaling mediated by RXR heterodimerization with NGFI-B and NURR1. Genes & Develop. 9:769-782 (1995).

Petty et al., Weekly paclitaxel (Taxol®), carboplatin (Paraplatin®), and bexarotene (Tagretin®) for the treatment of patients with advanced non-small cell lung cancer: Efficacy results from a Phase I/II study. Journal of Clinical ONcolocy, 2005 ASCO Annual Meeting Proceedings, vol. 23, No. 16S, Part I of II (Jun. 1 Supplement) Abstract 7243 (2005).

(56) References Cited

OTHER PUBLICATIONS

Pierrot et al., Targretin Improves Cognitive and Biological Markers in a Patient with Alzheimer's Disease. Journal of Alzheimer's Disease, 49:271-276 (2016).
Price et al., Comment on ApoE-directed Therapeutics Rapidly Clear beta-Amyloid and Reverse Deficits in AD Mouse Models. Science 340:924-d (2013).
Ramaswamy et al., Trophic factors therapy in Parkinson's disease. Prog. Brain Res., 175:201-216 (2009).
Ramlau et al., Randomized phase III trial comparing bexarotene (L1069-49)/cisplatin/vinorelbine with cisplatin/vinorelbine in chemotherapy-naïve patients with advanced or metastic non-small-cell lung cancer: SPIRIT I. J. Clin. Oncol., 26:1886-1892 (2008).
Reynolds et al., Regulatory T cells attenuate Th17 cell-mediated nigrostriatal dopaminergic neurodegneration in a model of Parkinson's disease. J. Immunol., vol. 184, pp. 2261-2271 (2010).
Riancho et al., Neuroprotective effect of bexarotene in SOD1G93A mouse model of amyotrophic lateral sclerosis. Frontiers in Cellular Neuroscience 9:Article 250 (2015).
Rigas et al., Emerging role of rexinoids in non-small cell lung cancer: Focus on bexarotene. The Oncologist, 10:22-33 (2005).
Rizvi et al., A phase I study of LGD1069 in adults with advanced cancer. Clin. Cancer Res., 5:1658-1664 (1999).
Sacchetti et al., Requirements for heterodimerization between orphan nuclear receptor Nurr1 and Retinoid X Receptors. The Journal of Biological Chemistry, 277(38):35088-35096 (2002).
Salama et al., Role of L-thyroxin in counteracting rotenone induced neurotoxocity in rats. Environmental Toxicology and Pharmacology, 35:270-277 (2013).
Sherman et al., Central hypothyroidism associated with retinoid X receptor-selective ligands. The New England Journal of Medicine, vol. 340, No. 14, pp. 1075-1079 (1999).
Alcala-Barraza et al., Intranasal delivery of neurotrophic factors BDNF, CNTF, EPO, and NT-4 to the CNS. Journal of Drug Targeting, 18(3):179-190 (2009).
Altucci L et al., RAR and RXR modulation in cancer and metabolic disease. Nature Review Drug Discovery, vol. 6: 793-810 (2007).
Alzforum 2013: Can Cancer Therapy be Neurodegenerative Wonder Drug?
Annerbo et al., Review Article: A clinical review of the association of thyroid stimulating hormone and cognitive impairment ISRN Endocrinology, vol. 2013, Article ID 856017, 6 pages (2013).
Balasubramanian et al., Suppression of human pancreatic cancer cell proliferation by AGN194204, an RXR-selective retinoid. Carcinogenesis, 2004, vol. 25, No. 8, pp. 1377-1385.
Balducci et al., The Continuing Failure of Bexarotene in Alzheimer's Disease Mice. J Alzheimers Dis., 46:471-482 (2015).
Benson et al., All-trans retinoic acid mediates enhanced T reg cell growth, differentiation, and gut homing in the face of high levels of co-stimulation. The Journal of Experimental Medicine, vol. 204, No. 8, pp. 1765-1774 (2007).
Beyer et al., Weight change and body composition in patients with Parkinson's disease. J. Am. DietAssoc., vol. 95, pp. 979-983 (1995).
Bilbao et al., Insulin-like growth factor-1 stimulates regulatory T cells and suppresses autoimmune disease. EMBO Mol. Med., 6(11):1423-1435 (2014).
Blumenschein et al., A randomized phase III trial comparing bexarotene/carboplatin/paclitaxel versus carboplatin/paclitaxel in chemotherapy-naive patients with advanced or metastatic non-small cell lung cancer (NSCLC). Journal of Clinical Oncology, 2005 ASCO Annual Meeting Proceedings, vol. 23, No. 16S, Part I of II, Abstract 7001 (2005).
Bordoni et al., Bexarotene improves TTP in untreated, advanced NSCLC, when given in combination with carboplalin/paclitaxel. Journal of Clinical Oncology, ASCO 2005 Annual Meeting, Abstract 7270.
Breen et al., Regulation of Thyroid-Stimulating Hormone beta-Subunit and Growth Hormone Messenger Ribonucleic Acid Levels in the Rat: Effect of Vitamin A Status, Endocrinology 136:543-9 (1995).

Cal et al., Doxazosin: a new cytotoxic agent for prostate cancer? BJU Int. 85:672-675 (2000).
Calza et al., Thyroid hormone activates oligodendrocyte precursors and increases a myelin-forming protein and NGF content in the spinal cord during experimental allergic encephalomyelitis. PNAS, vol. 99, No. 5, pp. 3258-3263 (2002).
Coya et al., Retinoic Acid Inhibits In Vivo Thyroid-Stimulating Hormone Secretion, Life Sciences, Pharmacology Letters, 60:247-50, 1997.
Cramer et al., ApoE-directed therapeutics rapidly clear β-amyloid and reverse deficits in AD mouse models. Science, 335(6075): 1503-1506 (2012).
Crowe et al.,A retinoid X receptor (RXR)-selective retinoid reveals that RXR-alpha is potentially a therapeutic target in breast cancer cell lines, and that it potentiates antiproliferative and apoptotic responses to peroxisome proliferator-activated receptor ligands. Breast Cancer Res., vol. 6, No. 5, pp. R546-R555 (2004).
Cummings et al., Double-blind, placebo-controlled, proof-of-concept trial of bexarotene Xin moderate Alzheimer's disease Alzheimer's Research & Therapy, 8:4 (2016).
Debnath & Berk, Th17 Pathway-Mediated Immunopathogenesis of Schizophrenia: Mechanisms and Implications. Schizophrenia Bulletin, 40(6):1412-1421 (2014).
Dell'Acqua ML et al., Functional and molecular evidence of myelin- and neuroprotection by thyroid hormone administration in experimental allergic encephalomyelitis. Neuropath. Appl. Neurobiol., 38:454-470 (2012).
D'Intino G et al., Triiodothyronine administration ameliorates the demyelination/remyelination ratio in a non-human primate model of multiple sclerosis by corrected tissue hypothyroidism. J Neuroendocrin., 23:778-790 (2011).
Dore et al., Insulin-like growth factor I protects and rescues hippocampal neurons against beta-amyloid- and human amylin-induced toxicity. Proc. Natl. Acad. Sci. USA, 94:4772-4777 (1997).
Duvic et al., Phase 2 and 3 Clinical Trial of Oral Bexarotene (Targretin Capsules) for the Treatment of Refractory or Persistent Early-Stage Cutaneous T-Cell Lymphoma, Arch Dermatol. 137:581-593, 2001.
Estephan et al., Phase II trial of gemcitabine (G), carboplatin (C) and bexarotene (B) in patients (pts) with newly diagnosed, locally-advanced or metastatic non-small cell carcinoma of the lung. Journal of Clinical Oncology, 2005 ASCO Annual Meeting Proceedings, vol. 23, No. 16S, Part I of II (Jun. 1 Supplement, Abstract 7308 (2005).
Elias et al., Retinoic acid inhibits TH17 polarization and enhances FoxP3 expression through a Stat-3/Stat-5 independent signaling pathway. Blood, vol. 111, No. 3, pp. 1013-1020 (2008).
Fitz et al., Comment on ApoE-directed Therapeutics Rapidly Clear beta-Amyloid and Reverse Deficits in AD Mouse Models. Science 340:924-c (2013).
Franco et al., Thyroid hormones promote differentiation of oligodendrocyte progenitor cells and improve remyelination after cuprizone-induced demyelination. Experimental Neurology, 212, pp. 458-467, 2008 (2008).
Freiherr et al., Intranasal Insulin as a Treatment for Alzheimer's Disease: A Review of Basic Research and Clinical Evidence. CNS Drugs 27:505-514 (2013).
Friling et al., Activation of retinoid X receptor increases dopamine cell survival in models for Parkinson's disease. BMC Neuroscience, 10: 146 (2009).
Fu et al., Thyroid hormone prevents cognitive deficit in a mouse model of Alzheimer's disease. Neuropharmacology, 58:722-729 (2010).
Gibb et al., The substantia nigra and ventral tegmental area in Alzheimer's disease and Down's sydrome. J. Neurol. Neurosurg. and Psychiatry, 52:193-200 (1989).
Golub et al., Molecular classification of cancer: Class discovery and class prediction by gene expression monitoring. Science, vol. 286, Oct. 15, 1999, pp. 531-537.
Gonzalez et al., T-cell-mediated regulation of neuroinflammation involved in neurodegenerative diseases. J Neuroinflam 11:201-212 (2014).

(56) References Cited

OTHER PUBLICATIONS

Govindan et al., Phase II trial of bexarotene capsules in patients with non-small-cell lung cancer (NSCLC) who have Failed at least 2 prior systemic therapies for Stage IIIB/IV disease. Journal of Clinical Oncology, 2005 ASCO Annual Meeting Proceedings, vol. 23, No. 16S, Part I of II, Abstract 7116 (2005).
Graber et al., Protective autoimmunity in the nervous system. Pharmacol. Therapeut., 121:147-159 (2009).
Haugen et al., The Thyrotrope-Restricted Isoform of the Retinoid-X Receptor-y1 Mediates 9-cis-Retinoic Acid Suppression of Thyrotropin-beta Promoter Activity. Molecular Endocrinology 11:481-9, 1997.
Henkel et al., Regulatory T-lymphocytes mediate amyotrophic lateral sclerosis progression and survival. EMBO Mol. Med., 5:64-79 (2012).
Hu et al., Imbalance between IL-17A-Producing Cells and Regulatory T Cells during Ischemic Stroke. Mediators of Inflammation 2014: Article ID 813045, 2014.
Huang et al., Retinoid X receptor gamma signaling accelerates CNS remyelination, Nature Neuroscience, 14(1): 45-53, 2011 (Epub Dec. 5, 2010).
International Search Report and Written Opinion dated Mar. 28, 2013 for International Application Serial No. PCT/US2012/069566 filed on Dec. 13, 2012.
International Search Report and Written Opinion dated Jan. 5, 2017 for International Application Serial No. PCT/US2016/059770 filed Oct. 31, 2016.
International Search Report for PCT/US2007/011730 dated May 2, 2008.
International Search Report and Written Opinion dated Sep. 25, 2007 for International Application No. PCT/US2006/038252 filed on Oct. 2, 2006.
International Search Report and Written Opinion dated Dec. 29, 2016 for International Application No. PCT/US2016/059775 filed on Oct. 31, 2016.
International Search Report and Written Opinion dated Jan. 10, 2017 for International Application No. PCT/US2016/059776 filed on Oct. 31, 2016.
International Search Report and Written Opinion dated Dec. 29, 2016 for International Application No. PCT/US2016/059779 filed on Oct. 31, 2016.
International Search Report and Written Opinion dated May 22, 2017 for International Application No. PCT/US2016/059772 filed on Oct. 31, 2016.
International Search Report and Written Opinion dated Jan. 18, 2019 for International Application No. PCT/US2018/052031 filed on Sep. 20, 2018.
International Search Report and Written Opinion dated Dec. 11, 2018 for International Application No. PCT/US2018/048876 filed on Aug. 30, 2018.
Alsudais et al., Retinoid X receptor-selective signaling in the regulation of Akt/protein kinase B isoform-specific expression. The Journal of Biological Chemistry, vol. 291, No. 6, pp. 3090-3099 (2015).
Silvestroff et al., Cuprizone-induced demyelination in the rat cerebral cortex and thyroid hormone effects on cortical remyelination. Experimental Neurology, 235, pp. 357-367 (2012).
Smit et al., Bexarotene-induced hypothrodism: bexarotene stimulates the peripheral metabolism of thyroid hormones. J. Clin. Endocrinol. Metab., 92(7):2496-2499 (2007).
Suh et al., Prevention and treatment of experimental breast cancer with the combination of a new selective estrogen receptor modulator, Arzoxifene, and a new rexinoid, LG 100268. Clin Cancer Res, 8:3270-3275 (2002).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Teng et al., Identification of highly potent retinoic acid receptor alpha-selective antagonists. Journal of Medicinal Chemistry, vol. 40, pp. 2445-2451 (1997).

Tesseur et al., Comment on ApoE-directed Therapeutics Rapidly Clear beta-Amyloid and Reverse Deficits in AD Mouse Models. Science, 340:924-e (2013).
Tovar-Y-Romo et al., Trophic factors as modulators of motor neuron physiology and survival: implications for ALS therapy. Frontiers in Cellular Neuroscience, 8:Article 61 (2014).
Trillo et al., Ascending monoaminergic systems alterations in Alzheimer's disease. Translating basic science into clinical care. Neuroscience and Biobehavioral Riviews, 37:1363-1379 (2013).
Assaf et al., Minimizing adverse side-effects of oral bexarotene in cutaneous T-cell lymphoma: an expert opinion. British Journal of Dermatology, 155, pp. 261-266 (2006).
Diab et al., Ligands for the peroxisome proliferator-activated receptor-gamma and the retinoid X receptor exert additive anti-inflammatory effects on experimental autoimmune encephalomyelitis. Journal of Neuroimmunology, 148, pp. 116-126 (2004).
Extended European Search Report, dated Oct. 1, 2019, for European Application No. 16893789.4 filed Oct. 31, 2016.
Farmer et al., Retinoic acid receptor ligands based on the 6-cyclopropyl-2,4-hexadienoic acid. Bioorganic & Medicinal Chemistry Letters, 13:261-264 (2003).
Hsu et al., Generation and characterization of monoclonal antibodies directed against the surface antigens of cervical Cancer cells. Hybrid Hybridomics, vol. 23, No. 2, pp. 121-125 (2004)—abstract.
Uslu et al., Doxazosin: a new cytotoxic agent for prostate cancer? BJU International, vol. 85, pp. 672-675 (2000).
Veeraraghavalu et al., Comment on ApoE-directed Therapeutics Rapidly Clear beta-Amyloid and Reverse Deficits in AD Mouse Models. Science 340:924-f, 2013.
Volakakis et al., Nurr1 and Retinoid X Receptor ligands stimulate Ret signaling in dopamine neurons and can alleviate alpha-synuclein disrupted gene expression. J. Neurosci., 35(42):14370-14385 (2015).
Walkley et al., Retinoic acid receptor anatagonism in vivo expands the numbers of precursor cells during granulopoiesis. Leukemia, vol. 16, No. 9, pp. 1763-1772 (2002).
Wallen-MacKenzie et al., Nurr1-RXR heterodimers mediate RXR ligand-induced signaling in neuronal cells. Genes and Development, 17: 3036-3047 (2003).
Wang et al., Selective brain penetrable Nurr1 transactivator for treating Parkinson's disease. Oncotarget 7 (7):7469-7479 (2016).
Wang, (2013) Slide presentation at the Symposium on IRX4204 at the 11th International Conference on Alzheimer's and Parkinson's Diseases: The Novel RXR agonist IRX4204 as a Potential Disease-Modifying Agent in Alzheimer's Disease.
WebMD, Common Drugs and Medicines to Treat Multiple Sclerosis; Drugs & Medications Search, accessed May 12, 2017; pp. 1-3.
Xiao et al., Retinoic acid increases Foxp3+ regulatory T cells and inhibits development of TH17 cells by enhancing TFG-β-driven Smad3 signaling and inhibiting IL-6 and IL-23 receptor expression. The Journal of Immunology, 181: 2277-2284 (2008).
Xiao et al., Adenomatous polyposis coli (APC)-independent regulation of beta-catenin degradation via a retinoid X receptor-mediated pathway. Journal of Biological Chemistry, vol. 278, No. 32, pp. 29954-29962 (2003).
Yacila & Sari, Potential Therapeutic Drugs and Methods for the Treatment of Amyotrophic Lateral Sclerosis. Curr. Med. Chem., 21(31):3583-3593 (2014).
Yamada et al., Retinoid X receptor ligands: a patent review (2007-2013). Expert Opin. Ther. Patents, 24(4):443-452 (2014).
Zapata-Gonzalez et al., 9-cis-retinoic acid (9cRA), a retinoid X receptor (RXR) ligand, exerts immunosuppressive effects on dendritic cells by RXR-dependent activation: inhibition of peroxisome proliferator-activated receptor gamma blocks some of the 9cRA activities, and precludes them to mature phenotype development The Journal of Immunogloy, 178:6130-6139 (2007).
Zhang et al., Thyroid hormone potentially benefits multiple sclerosis via facilitating remyelination. Mol. Neurobiol., 53, pp. 4406-4416 (2016).
Jones et al., Animal models of schizophrenia. British Journal of Pharmacology, 164:1162-1194 (2011).

(56) References Cited

OTHER PUBLICATIONS

Kabbinavar et al., An open-label phase II clinical trial of the RXR agonist IRX4204 in taxane-resistant, castration-resistant metastatic prostate cancer (CRPC). Journal of Clinical Oncology, vol. 32, No. 15 Suppl, p. 5073 (2014).
Kim, Chang H. Regulation of FoxP3+ regulatory T cells and Th17 cells by retinoids. Clinical and Developmental Immunology, vol. 2008, 12 pages (2008).
Koivusalo et al., The cytotoxicity of chemotherapy drugs varies in cervical cancer cells depending on the p53 status Cancer Biology and Therapy, vol. 3278(11):1177-1183 (2004).
Liu et al., Mechanism of selective retinoid X receptor agonist-induced hypothroidism in the rat. Endocrinology, 143(8):2880-2885 (2002).
Singaporean Written Opinion, dated Sep. 26, 2019, for Singaporean Application No. 11201807250P filed on Oct. 31, 2016.
Singaporean Written Opinion, dated Sep. 16, 2019, for Singaporean Application No. 11201807255Y filed on Oct. 31, 2016.
Supplementary European Search Report for European Patent Application Serial No. 16861057 dated May 22, 2019.
Supplementary European Search Report for European Patent Application Serial No. 16861059 dated May 16, 2019.
Vuligonda et al., Enantioselective syntheses of potent retinoid X receptor ligands: Differential biological activities of individual antipodes J. Med. Chem., 44. pp. 2298-2303 (2001).
Aranami et al., Th 17 cells and autoimmune encephalomyelitis (EAE/MS). Allergology International, 57:115-120 (2008).
Reagan-Shaw et al., Dose translation from animal to human studies revisted. FASEB J, 22:659-661 (2007).
Certo et al., Activation of RXXR/PPARy underlies neuroprotection by bexarotene in ischemic stroke. Pharm. Resc. 102:298-307 (2015).
Chinese Office Action, dated May 21, 2020, for Chinese Patent Application No. 201680083364.8 (original and translation included).
Extended European Search Report for EP 16861057, dated Jul. 6, 2019.
Graeppi-Dulac et al., Endocrine Side-Effects of Anti-Cancer Drugs: The impact of retinoids on the thryoid axis. European Journal of Endocrinology, 170(6), R253-R262 (2014).
Lalloyer et al., Rexinoid bexarotene modulates triglyceride but not cholesterol metabolism in the liver. Arterioscler Thromb Vase Biol 29(10):1488-1495 (2009).
Liby et al., A new rexinoid, NXR194204, prevents carcinogenesis in both the lung and mammary gland. Clin Cancer Res, 13(20):6237-6243 (2007).
Mor et al., Autoimmune encephalomyelitis and uveitis induced by T cell immunity to self beta-synuclein. The Journal of Immunology, 170:628-634 (2003).
Alsuliman A., et al. "A robust, good manufacturing practice-compliant, clinical-scale procedure to generate regulatoryT cells from patients with amyotrophic lateral sclerosis for adoptive cell therapy," Cytotherapy 18:1312-1324, 2016.
Trapp et al., Axonal transection in the lesions of multiple sclerosis. N Engl J Med 338:278-785 (1998).
Wikipedia, Schizophrenia, https://www.nimh.nih.gov/health/statistics/schizophrenia.html, accessed Feb. 20, 2020.
Bendele, Animal models of rheumatoid arthritis. J Musculoskel Neuron Interact, 1(4):377-385 (2001).
Harris, Retinoid therapy for rheumatoid arthritis. Annals of Internal Medicine, vol. 100(1), pp. 146-147 (1984).
Mucida et al., Supplemental Online Material: Reciprocal Th-17 and regulatory T cell differentiation mediated by retinoic acid. Retrieved on Mar. 5, 2021. Retrieved from internet, url:www.sciencemag.org/cgi/conent/full/1145697/DC1>(Year:2007).
Mucida et al., Reciprocal Th-17 and regulatory T cell differentiation mediated by retinoic acid. Science, vol. 317 (5835), pp. 256-260 (2007).
Science Daily [online] (2007), Potential role for retinoic acid in autoimmune and inflammatory diseases identified, La Jolla Institute for Allergy and Immunology p. 1-3 Retrieved from the internet, Retrieved on Mar. 5, 2021, <url:www.sciencedaily.com/releases/2007/06/070614151809.htm> (Year:2007).
Rittenhouse et al., Thyroxine administration prevents streptococcal cell wall-induced inflammatory responses. Endocrinology, 138(4):1434-1439 (1997).
Sugiyama et al., Dysfunctional blood and target tissue CD4+ CD25high regulatory T cells in psoriasis: Mechanism underlying unrestrained pathogenic effector T cell proliferation. J. Immunol, 174:164-173 (2005).
Waite et al., Review Article: Th17 response and inflammatory autoimmune diseaes. International Journal of Inflammation, vol. 2012, Article ID 819467, 10 pp (2011).
Wikipedia, Experimental autoimmune encephalomyelitis, https://en.wikipedia.org/wiki/Experimental_autoimmune_encephalomyelitis, accessed Jul. 1, 2019 (last edited on Feb. 10, 2019).
Zhao et al., Application of thyroid hormone in animal models of multiple sclerosis. Drug Evaluation Research, 39 (1):148-151 (2016).
Andreaone et al., Cerebral atrophy and white matter disruption in chronic schizophrenia. EUR Arch Psychiatry Clin Neurol 257:3-11 (Feb. 2007).
Andreaone et al., Cortical white-matter microstructure in schizophrenia. British J Psychiatry 191:113-119 (Aug. 2007).
Banati et al., Inflammatory reaction in experimental autoimmune encephalomyelitis (EAE) is accompanied by a microglial expression of the betaA4-amyloid precursor protein (APP). Gila 14:209-215 (1995).
Becher et al., Th17 cytokines in autoimmune neuro-inflammation. CurrOpin Immunol 23(6):707-712(2011).
Bettelli et al., Induction and effector functions of Th17 cells. Nature 453(7198):1051-1057 (2008).
Chandraratna et al., Treatment with retinoid X receptor agonist IRX4204 ameliorates experimental autoimmune encephalomyelitis. Am J Transl Res 8(2):1016-1026 (2016).
Davis et al., White matter changes in schizoprenia—Evidence for myelin-related dysfunction. Arch Gen Psychiatry 60:443-456 (2003).
Debnath & Berk, Functional implications of the IL-23/IL-17 immune axis in schizophrenia. Mol Neurobiol, 54:8170-8178 (2017).
Ding et al., Activation of Th17 cells in drug naive, first episode schizophrenia. Progress in Neuro-Pyschopharmacology & Biological Psychiatry, 51:78-82 (2014).
Domingues et al., Functional and pathogenic differences of Th1 and Th17 cells in experimental autoimmune encephalomyelitis. PLOS One, 5(11):e15531 (2010).
Drexhage et al., An activated set point of T-cell monocyte inflammatory networks in recent-onset schizophrenia patients involves both pro- and anti-inflammatory forces. International Journal of Neuropsychopharmacology, 14:746-755 (2011).
Flygt et al., Myelin loss and oligodendrocyte pathology in white matter tracts following traumatic brain injury in the rat. European Journal of Neuroscience 38:2153-2165 (2013).
Flynn et al., Abnormalities of myelination in schizophrenia detected in vivo with MRI, and post-mortem with analysis of oligodendrocyte proteins. Molecular Psychiatry, 8:811-820 (2003).
Gilgun-Sherki et al., Riluzole suppresses experimental autoimmune encephalomyelitis: implications for the treatment of multiple sclerosis. Brain Research, 989:196-201 (2003).
Haqqani et al., Intercellular interactomics of human brain endothelial cells and Th17 lymphocytes: a novel strategy for identifying therapeutic targets of CNS inflammation. Cardiovascular Psychiatry and Neurology 2011: ID175364 (2011).
Inglese et al., Therapeutic strategies in multiple sclerosis: A focus on neuroprotection and repair and relevance to schizophrenia. Schizophrenia Research, 161:94-101 (2015).
Johnson et al., Axonal pathology in traumatic brain injury. Exp Nuerol, 246:35-43 (2013).
Kebir et al., Human Th17 lymphocytes promote blood-brain barrier disruption and central nervous system inflammation. Nat Med 13(10):1173-1175 (2007).
Komiyama et al., IL-17 plays an important role in the development of experimental autoimmune encephalomyelitis. J. Immunol., 177:566-573 (2006).
Koster et al., Emerging drugs for schizophrenia: an update. Expert Opin Emerging Drugs, 19(4):511-531 (2014).

(56) References Cited

OTHER PUBLICATIONS

Li et al., Plasma levels of Th17-related cytokines and complement C3 correlated with aggressive behavior in patients with schizophrenia Psychiatry Research, 246:700-706 (2016).

Mai et al., T helpher 17 cells interplay with CD4+CD25highFoxp3+ Tregs in regulation of inflammations and autoimmune diseases. Front Biosci, 15:986-1006 (2010).

Miller et al., Meta-analysis of cytokine alterations in schizophrenia: Clinical status and antipsychotic effects. Biol Psychiatry, 70(7):663-671 (2011).

Miller et al., Meta-analysis of lymphocytes in schizophrenia: Clinical status and antipsychotic effects. Biol Psychiatry, 73(10):993-999 (2013).

Moriya et al., Edaravone, a free radical scavenger, ameliorates experimental autoimmune encephalomyelitis. Neuroscience Letters, 440:323-326, 2008.

Murphy et al., Infiltration of Th1 and Th17 cells and activation of microglia in the CNS during the course of experimental autoimmune encephalomyelitis. Brain Behavior and Immunity, 24:641-651 (2010).

Pastemak et al., The extent of diffusion MRI markers of neuroinflammation and white matter deterioration in chronic schizophrenia. Schizophrenia Research, 161(1):113-118 (2015).

Rostami et al., Role of Th17 cells in the pathogenesis of CNS inflammatory demyelination. J. Neurol Sci, 330:76-87 (2013).

Saresella et al., T helper-17 activation dominates the immunologic milieu of both amyotrophic lateral sclerosis and progressive multiple sclerosis. Clincal Immunology, 148:79-88 (2013).

Schneider et al., Hyperphosphorylation and aggregation of Tau in experimental autoimmune encephalomyelitis. J Biol Chem 279(53):55833-55839 (2004).

Segal, Th17 cells in autoimmune demyelinating disease. Semin Immunopathol, 32(1):71-77 (2010).

Smith, A comprehensive macrophage-T-lymphocyte theory of schizophrenia. Medical Hypotheses, 39:248-257 (1992).

Stromnes et al., Differential regulation of central nervous system autoimmunity by TH1 and TH17 cells. Nat Med, 14 (3):337-342 (2008).

Hueber et al., Effects of AIN457, a fully human antibody to interleukin-17A, on psoriasis, rheumatoid arthritis, and uveitis. Science Translational Medicine, vol. 2, Issue 52, 52ra72 (2010).

Singaporean Written Opinion, dated Apr. 22, 2021, for Singaporean Application No. 11201807255Y filed on Oct. 31, 2016.

* cited by examiner

AUTOIMMUNE DISORDER TREATMENT USING RXR AGONISTS

This patent application is a continuation of U.S. patent application Ser. No. 17/126,787, filed Dec. 18, 2020, now U.S. Pat. No. 11,246,845, which is a continuation of U.S. patent application Ser. No. 16/742,616, filed Jan. 14, 2020, which is a continuation of U.S. patent application Ser. No. 16/228,217, filed Dec. 20, 2018, now U.S. Pat. No. 10,945,976, which is a continuation of U.S. patent application Ser. No. 15/852,580, filed Dec. 22, 2017, now U.S. Pat. No. 10,201,512 which is a continuation of U.S. patent application Ser. No. 15/341,969, filed Nov. 2, 2016, now U.S. Pat. No. 10,285,960, which is a continuation of U.S. patent application Ser. No. 13/714,051 filed Dec. 13, 2012, now abandoned, which claims priority pursuant to 35 U.S.C. § 119(e) to U.S. Provisional Patent Application Ser. No. 61/570,182, filed Dec. 13, 2011, each of which is hereby incorporated by reference in its entirety.

This invention was made with government support under R01-CA062275 and R01-AT005382 awarded by National Institutes of Health (NIH). The government has certain rights in the invention.

Attempts to treat autoimmune disorders have met with limited success. This is due, in part, to the fact that the etiology of autoimmune disorders is a complex response based in part on a combination of factors, including, without limitation, genetic make-up of individual, gender or hormonal status, bacterial or viral infection, metal or chemical toxin exposure, vaccinations or immunizations, stress, trauma, smoking and/or nutritional deficiencies. Therefore, compounds, compositions, and methods that can reduce a symptom associated with an autoimmune disorder, inflammation associated with an autoimmune disorder, and/or a transplant rejection would be highly desirable.

Naïve CD4+ T cells play a central role in immune protection. They do so through their capacity to help B cells make antibodies, to induce macrophages to develop enhanced microbicidal activity, to recruit neutrophils, eosinophils, and basophils to sites of infection and inflammation, and, through their production of cytokines and chemokines, to orchestrate the full panoply of immune responses. Naïve CD4+ T cells are multipotential precursors that differentiate into various T cell subsets, such as, e.g., T helper (Th) cells (also called T effector cells) and T regulatory (Treg) cells. T helper cells are characterized by their distinct functions and include Th1, Th2, and Th17. Th1 cells aid in the clearance of intracellular bacteria and viruses, secrete IFN-γ in response to the cytokine interleukin-12 (IL-12), and require the transcription factors T-box21 (T-bet) and signal transducer and activator of transcription 1 (Stat1) and (Stat4). Th2 cells help control extracellular pathogens, secrete the cytokines IL-4, IL-5 and IL-13, and require transcription factors GATA-binding protein 3 (GATA-3) and Stat6. Th17 cells provide protection against fungi and various other extracellular bacteria, secrete the pro-inflammatory cytokine IL-17A, and express the transcription factor retinoic acid orphan receptor gamma (RORγt). Treg cells play a critical role in maintaining self-tolerance as well as in regulating immune responses and express the transcription factor forkhead box P3 (FoxP3). Tregs normally develop in the thymus, but can also differentiate from naïve CD4+ cells stimulated with TGF-β and IL-2. Development and differentiation of Treg cells, as well as expression of FoxP3, require the transcription factor Stat5.

Although several cytokines participate in Th17 cell differentiation, IL-6 and TGF-β are key factors for the generation of Th17 cells from naïve T CD4+ cells. On the other hand, IL-6 inhibits TGF-β-induced Treg cells which suppress adaptive T cell responses and prevent autoimmunity, and are thus important in the maintenance of immune homeostasis. The two T-cell subsets play prominent roles in immune functions: Th17 plays a key role in the pathogenesis of autoimmune diseases and protection against bacterial infections, while Treg functions to restrain excessive helper T-cell responses. Essentially immunosuppressive Tregs cells and pro-inflammatory Th17 cells functionally antagonize each other.

As such, a fine balance between Th17 and Treg cells may be crucial for the stability of immune homeostasis. Once the equilibrium is broken, the destabilization may lead to chronic inflammation and autoimmunity. For example, dysregulation or overproduction of IL-6 leads to autoimmune diseases such as multiple sclerosis (MS) and rheumatoid arthritis (RA), in which Th17 cells are considered to be the primary cause of pathology. Clinical evidence indicates that both defects in Treg function or reduced numbers, as well as Th17 activity are important in several autoimmune diseases, including seronegative arthritis in adults, and childhood arthritis (juvenile idiopathic arthritis). Therefore, an effective approach in the treatment of various autoimmune and inflammatory diseases will be to normalize the balance between Treg and Th17 cell development.

There are two main types of receptors that mediate the effects of derivatives of vitamin A in mammals (and other organisms), the Retinoic Acid Receptors (RARs) and the Retinoid X Receptors (RXRs). Within each type there are three subtypes designated RAR alpha, RAR beta, and RAR gamma for the RAR family and RXR alpha, RXR beta, and RXR gamma for the RXR family. These receptor types are evolutionarily related but are functionally distinct. The ligands that activate the RARs, referred to as retinoids, and the ligands that activate the RXRs, referred to as rexinoids, elicit quite different biological effects. Retinoic acid (RA), the physiological hormone of all three RARs, has been shown to enhance the in vitro differentiation of Treg cells that suppress immunity. RA can also inhibit the differentiation of pro-inflammatory Th17 cells that have been casually implicated in the development of many human autoimmune diseases. Based on this ability to restore a normal Th17/Treg cell ratio by decreasing Th17 cells while simultaneously increasing Treg cells, RAR agonists have been proposed as effective therapeutic compounds for the treatment of inflammatory and autoimmune disorders. However, recent findings have identified retinoid signaling through RARs as being required for the initial development of Th17 cell mediated immune responses and inflammation. These counteracting effects of RAR pan agonists on Th17 cell development bring into question the value of such compounds as anti-inflammatory and immunosuppressive agents.

Although RAR agonists like RA have been used to treat autoimmune disorders associated with inflammation, their usefulness in clinical practice has been limited due to unwanted side effects and counter-therapeutic inflammatory effects. Thus, what are needed are compounds and compositions that maintain the ability to inhibit Th17 cell formation and function and to promote Treg cell formation, but not possess any pro-inflammatory activities and other unwanted side effects associated with RAR pan agonists like RA. Such compounds will be of considerable therapeutic value as immunomodulatory agents.

The present specification discloses compounds, compositions, and methods for treating an individual suffering from an autoimmune disorder. This is accomplished by administering a therapeutically effective amount of a RXR agonist or composition comprising such agonist to an individual suffering from an autoimmune disorder. As disclosed herein, the disclosed RXR agonists can control the Th17/Treg cell number ratio by elevating Treg cell numbers and suppressing Th17 cell numbers. As such, the disclosed RXR agonists would be useful in treating an autoimmune disorder.

SUMMARY

Thus, aspects of the present specification disclose a RXR agonist. Non-limiting examples of a RXR agonist include a compound having the structure of formula I,

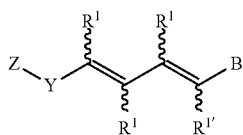

(I)

wherein Z is a radical having the structure of Formula II:

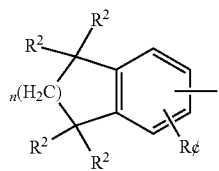

(II)

Y is cycloalkyl or cycloalkenyl of 3 to 8 carbons optionally substituted with one or two $R^4$ groups, or Y is selected from phenyl, pyridyl, thienyl, furyl, pyrrolyl, pyridazinyl, pyrimidiyl, pyrazinyl, thiazolyl, oxazolyl, and imidazolyl, the groups being optionally substituted with one or two $R^4$ groups, the divalent Y radical being substituted by the Z and —($CR^1$=$CR^1$—$CR^1$=$CR^1$)— groups on adjacent carbons; $R^1$ and $R^2$ independently are H, lower alkyl or fluoroalkyl; $R^3$ is hydrogen, lower alkyl, Cl or Br; $R^4$ is lower alkyl, fluoroalkyl or halogen, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$OCOR^7$, —$CR^7(OR^{12})_2$, —$CR^7OR^{13}O$, or tri-lower alkylsilyl, where $R^7$ is an alkyl, cycloalkyl or alkenyl group, containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, $R^{13}$ is divalent alkyl radical of 2-5 carbons; and n is 1 or 2.

Other aspects of the present specification disclose a method of treating an autoimmune disorder, the method comprising the step of administering to an individual in need thereof a therapeutically effective amount of a RXR agonist, wherein administration of the compound or composition reduces a symptom associated with the autoimmune disorder, thereby treating the individual. Aspects of the present specification also disclose a use of a RXR agonist to treat an autoimmune disorder, wherein administration of the compound or composition reduces a symptom associated with the autoimmune disorder, thereby treating the individual. Non-limiting examples of a RXR agonist include a compound or a composition disclosed herein. The autoimmune disorder can be a systemic autoimmune disorder or an organ-specific autoimmune disorder. Non-limiting examples of an autoimmune disorder that can be treated using a compound or a composition disclosed herein include an acute disseminated encephalomyelitis (ADEM), an Addison's disease, an allergy, allergic rhinitis, an Alzheimer's disease, an anti-phospholipid antibody syndrome (APS), an arthritis such as, e.g., a monoarthritis, an oligoarthritis, or a polyarthritis like an osteoarthritis, a rheumatoid arthritis, a juvenile idiopathic arthritis, a septic arthritis, a spondyloarthropathy, a gout, a pseudogout, or Still's disease, an asthma, an autoimmune deficiency syndrome (AIDS), an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an endometriosis, a gastrointestinal disorder such as, e.g., an irritable bowel disease or an inflammatory bowel disease like Crohn's disease or an ulcerative colitis, a Goodpasture's syndrome, a Graves' disease, a Guillain-Barré syndrome (GBS), a Hashimoto's thyroiditis, a hidradenitis suppurativa, an idiopathic thrombocytopenic purpura, an interstitial cystitis, a lupus, such as, e.g., a discoid lupus erythematosus, a drug-induced lupus erythematosus, a lupus nephritis, a neonatal lupus, a subacute cutaneous lupus erythematosus, or a systemic lupus erythematosus, a morphea, a multiple sclerosis (MS), a myasthenia gravis, a myopathy such as, e.g., a dermatomyositis, an inclusion body myositis, or a polymyositis, a myositis, a narcolepsy, a neuromyotonia, a Parkinson's disease, a pemphigus vulgaris, a pernicious anaemia, a primary biliary cirrhosis, a psoriasis, a recurrent disseminated encephalomyelitis, a rheumatic fever, a schizophrenia, a scleroderma, a Sjögren's syndrome, a skin disorder such as, e.g., dermatitis, an eczema, a statis dermatitis, a hidradenitis suppurativa, a psoriasis, a rosacea or a scleroderma, a tenosynovitis, a uveitis, vasculitis such as, e.g., a Buerger's disease, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a microscopic polyarteritis/polyangiitis, a polyarteritis nodosa, a polymyalgia rheumatica (PMR), a rheumatoid vasculitis, a Takayasu arteritis, or a Wegener's granulomatosis, or a vitiligo. Non-limiting examples of a symptom reduced by a method of treating an autoimmune disorder disclosed herein include inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue, or the destruction of an organ or tissue. Non-limiting examples of an inflammation symptom reduced by a method of treating an autoimmune disorder disclosed herein include edema, hyperemia, erythema, bruising, tenderness, stiffness, swollenness, fever, a chill, congestion of the respiratory tract including nose, and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

Yet other aspects of the present specification disclose a method of treating inflammation as a result of an autoimmune disorder, the method comprising the step of administering to an individual in need thereof a therapeutically effective amount of a RXR agonist, wherein administration of the compound or composition reduces a symptom associated with inflammation, thereby treating the individual. Aspects of the present specification also disclose a use of a RXR agonist to treat inflammation as a result of an autoimmune disorder, wherein administration of the compound or composition reduces a symptom associated with inflammation, thereby treating the individual. Non-limiting examples of a RXR agonist include a compound or a composition disclosed herein. Non-limiting examples of a symptom reduced by a method of treating inflammation disclosed herein include edema, hyperemia, erythema, bruising, tenderness, stiffness, swollenness, fever, a chill, congestion of the respiratory tract including nose, and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

Still aspects of the present specification disclose a method of treating a transplant rejection, the method comprising the step of administering to an individual in need thereof a therapeutically effective amount of a RXR agonist, wherein administration of the RXR agonist reduces a symptom associated with the transplant rejection, thereby treating the individual. Aspects of the present specification also disclose a use of a RXR agonist to treat a transplant rejection, wherein administration of the compound or composition reduces a symptom associated with the transplant rejection, thereby treating the individual. Non-limiting examples of a RXR agonist include a compound or a composition disclosed herein. Non-limiting examples of a transplant rejection include a hyperacute rejection, an acute rejection, or a chronic rejection, as well as, a graft-versus-host-disease. Non-limiting examples of a symptom reduced by a method of treating a transplant rejection disclosed herein include inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue, or the destruction of an organ or tissue. Non-limiting examples of an inflammation symptom reduced by a method of treating a transplant rejection include edema, hyperemia, erythema, bruising, tenderness, stiffness, swollenness, fever, a chill, congestion of the respiratory tract including nose, and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

Further aspects of the present specification disclose a method of promoting Treg cell differentiation in an individual, the method comprising the step of administering to the individual in need thereof a therapeutically effective amount of a RXR agonist, wherein administration of the RXR agonist promotes Treg cell differentiation. Aspects of the present specification also disclose a use of a RXR agonist to promote Treg cell differentiation in an individual, wherein administration of the RXR agonist to the individual promotes Treg cell differentiation. Administration of the RXR agonist to the individual can also inhibit Th17 cell differentiation.

Further aspects of the present specification disclose a method of inhibiting Th17 cell differentiation in an individual, the method comprising the step of administering to the individual in need thereof a therapeutically effective amount of a RXR agonist, wherein administration of the RXR agonist inhibits Th17 cell differentiation. Aspects of the present specification also disclose a use of a RXR agonist to inhibit Th17 cell differentiation in an individual, wherein administration of the RXR agonist to the individual inhibits Th17 cell differentiation. Administration of the RXR agonist to the individual can also promote Treg cell differentiation.

Other aspects of the present specification disclose a method of concurrently promoting Treg cell differentiation as well as inhibiting Th17 cell differentiation in an individual, the method comprising the step of administering to the individual in need thereof a therapeutically effective amount of a RXR agonist, wherein administration of the RXR agonist promotes Treg cell differentiation and inhibits Th17 cell differentiation. Aspects of the present specification also disclose a use of a RXR agonist to concurrently promote Treg cell differentiation as well as inhibit Th17 cell differentiation in an individual, wherein administration of the RXR agonist to the individual promotes Treg cell differentiation and inhibits Th17 cell differentiation.

BRIEF DESCRIPTION OF DRAWINGS

FIG. 1A shows that RXR agonists regulate Foxp3 expression and FIG. 1B shows that RXR agonists regulate and $\alpha 4\beta 7$ expression.

FIG. 2A shows that RXR agonists increase Treg differentiation under Th17 conditions and FIG. 2B shows that RXR agonists inhibit Th17 differentiation under Th17 conditions (B).

FIG. 6A shows that RXR agonists reduce CD4+ T cell infiltration into the central nervous system; and FIG. 6B shows that RXR agonists reduce myeloid dendritic cell infiltration into the central nervous system.

DESCRIPTION

Figure 1A:
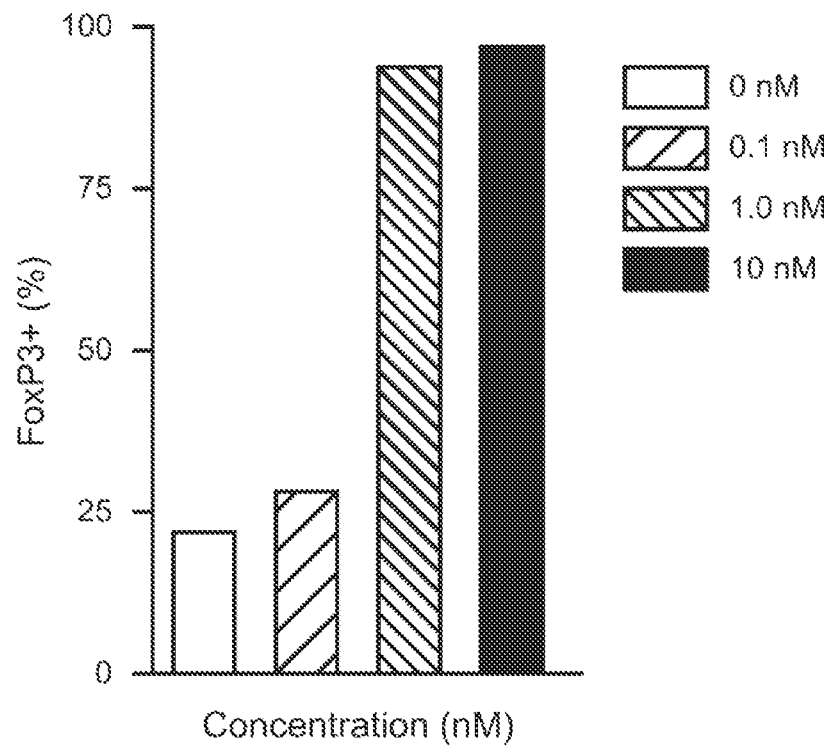
FIG. 1A-B shows RXR agonist effects on gene expression.

The RARs and RXRs and their cognate ligands function by distinct mechanisms. The RARs always form heterodimers with RXRs and these RAR/RXR heterodimers bind to specific response elements in the promoter regions of target genes. The binding of RAR agonists to the RAR receptor of the heterodimer results in activation of transcription of target genes leading to retinoid effects. On the other hand, RXR agonists do not activate RAR/RXR heterodimers. RXR heterodimer complexes like RAR/RXR, can be referred to as non-permissive RXR heterodimers as activation of transcription due to ligand-binding occurs only at the non-RXR protein (e.g., RAR); activation of transcription due to ligand binding does not occur at the RXR. RXRs also interact with nuclear receptors other than RARs and RXR agonists may elicit some of its biological effects by binding to such RXR/receptor complexes. These RXR/receptor complexes can be referred to as permissive RXR heterodimers as activation of transcription due to ligand-binding could occur at the RXR, the other receptor, or both receptors. Examples of RXR permissive heterodimers include, without limitation, peroxisome proliferator activated receptor/RXR (PPAR/RXR), farnesyl X receptor/RXR (FXR/RXR), or liver X receptor/RXR (LXR/RXR). Alternately, RXRs may form RXR/RXR homodimers which can be activated by RXR agonists leading to rexinoid effects. Also, RXRs interact with proteins other than nuclear receptors and ligand binding to an RXR within such protein complexes can also lead to rexinoid effects. Due to these differences in mechanisms of action, RXR agonists and RAR agonists elicit distinct biological outcomes and even in the instances where they mediate similar biological effects, they do so by different mechanisms. Moreover, the unwanted side effects of retinoids, such as pro-inflammatory responses or mucocutaneous toxicity, are mediated by activation of one or more of the RAR receptor subtypes. Stated another way, biological effects mediated via RXR pathways would not induce pro-inflammatory responses, and thus, would not result in unwanted side effects.

As disclosed herein, RXR agonists inhibit Th17 cell formation and promote Treg cell formation by mechanisms that do not involve their function as RAR agonists. As such, a selective RXR agonist that does not activate RARs would be a more effective agent in the treatment of an autoimmune disorder, inflammation associated with an autoimmune disorder, or a transplant rejection. In support of this, the present specification discloses that RXR agonists have cell differentiating effects in that they can regulate the Th17/Treg cell number ratio by elevating Treg cell numbers and suppressing Th17 cell numbers. In this manner, a normal balance of both these cell types can be achieved and immune homeostatis restored. Furthermore, since selective RXR agonists achieve these therapeutic effects without activation of RARs, they would be optimally effective and beneficial in treating an autoimmune disorder, inflammation associated with an autoimmune disorder, or a transplant rejection.

Thus, aspects of the present specification provide, in part, a RXR agonist. As used herein, the term "RXR agonist", is synonymous with "RXR selective agonist" and refers to a compound that selectively binds to one or more RXR receptors like a RXRα, a RXRβ, or a RXRγ in a manner that elicits gene transcription via an RXR response element. As used herein, the term "selectively binds," when made in reference to a RXR agonist, refers to the discriminatory binding of a RXR agonist to the indicated target receptor like a RXRα, a RXRβ, or a RXRγ such that the RXR agonist does not substantially bind with non-target receptors like a RARα, a RARβ or a RARγ.

A RXR agonist may be a pure RXR agonist. A pure RXR agonist is one which does not activate to any appreciable degree a permissive heterodimer such as, e.g., PPAR/RXR, FXR/RXR, and LXR/RXR. One example of a pure RXR agonist is 3,7-dimethyl-6(S),7(S)-methano,7-[1,1,4,4-tetramethyl-1,2,3,4-tetrahydronaphth-7-yl]2(E),4(E) heptadienoic acid (RXR agonist 194204) disclosed herein, the structure of which is shown in Formula XXIX. In an aspect of this embodiment, a pure RXR agonist shows no ability to activate a permissive heterodimer. In another aspect of this embodiment, a pure RXR agonist shows no ability to activate PPAR/RXR, FXR/RXR, and/or LXR/RXR. In other aspects of this embodiment, a pure RXR agonist activates a permissive heterodimer by 1% or less, 2% or less, 3% or less, 4% or less, 5% or less, 6% or less, 7% or less, 8% or less, 9% or less, or 10% or less relative to the ability of a non-pure RXR agonist to activate the same permissive heterodimer. A non-pure RXR agonist is one that can activate a permissive heterodimer like PPAR/RXR, FXR/RXR, or LXR/RXR. Example of a non-pure RXR agonist include, e.g., LGD1069 (bexarotene) and LGD268.

Selective binding of a RXR agonist to a RXR receptor includes binding properties such as, e.g., binding affinity and binding specificity. Binding affinity refers to the length of time a RXR agonist resides at its RXR receptor binding site, and can be viewed as the strength with which a RXR agonist binds its a RXR receptor. Binding affinity can be described as a RXR agonist's equilibrium dissociation constant (KD), which is defined as the ratio Kd/Ka at equilibrium, where Ka is a RXR agonist's association rate constant and kd is a RXR agonist's dissociation rate constant. Binding affinity is determined by both the association and the dissociation and alone neither high association nor low dissociation can ensure high affinity. The association rate constant (Ka), or on-rate constant (Kon), measures the number of binding events per unit time, or the propensity of a RXR agonist and its RXR receptor to associate reversibly into its agonist-receptor complex. The association rate constant is expressed in $M^{-1}$ $s^{-1}$, and is symbolized as follows: $[Ag] \times [Rc] \times Kon$. The larger the association rate constant, the more rapidly a RXR agonist binds to its RXR receptor, or the higher the binding affinity between agonist and receptor. The dissociation rate constant (Kd), or off-rate constant (Koff), measures the number of dissociation events per unit time propensity of an agonist-receptor complex to separate (dissociate) reversibly into its component molecules, namely the RXR agonist and the RXR receptor. The dissociation rate constant is expressed in $s^{-1}$, and is symbolized as follows: $[Ag+Rc] \times Koff$. The smaller the dissociation rate constant, the more tightly bound a RXR agonist is to its RXR receptor, or the higher the binding affinity between agonsit and receptor. The equilibrium dissociation constant (KD) measures the rate at which new agonist-receptor complexes formed equals the rate at which agonist-receptor complexes dissociate at equilibrium. The equilibrium dissociation constant is expressed in M, and is defined as $Koff/Kon=[Ag] \times [Rc]/[Ag+Rc]$, where [Ag] is the molar concentration of a RXR agonist, [Rc] is the molar concentration of the RXR receptor, and [Ag+Rc] is the of molar concentration of the agonist-receptor complex, where all concentrations are of such components when the system is at equilibrium. The smaller the equilibrium dissociation constant, the more tightly bound a RXR agonist is to its RXR receptor, or the higher the binding affinity between agonist and receptor.

In aspects of this embodiment, the binding affinity of a RXR agonist that selectively binds to a RXR receptor can have an association rate constant of, e.g., less than $1 \times 10^5$ $M^{-1}$ $s^{-1}$, less than $1 \times 10^6$ $M^{-1}$ $s^{-1}$, less than $1 \times 10^7$ $M^{-1}$ $s^{-1}$, or less than $1 \times 10^8$ $M^{-1}$ $s^{-1}$. In another embodiment, the binding affinity of a RXR agonist that selectively binds to a RXR receptor can have an association rate constant of, e.g., more than $1 \times 10^5$ $M^{-1}$ $s^{-1}$, more than $1 \times 10^6$ $M^{-1}$ $s^{-1}$, more than $1 \times 10^7$ $M^{-1}$ $s^{-1}$, or more than $1 \times 10^8$ $M^{-1}$ $s^{-1}$. In other aspects, the binding affinity of a RXR agonist that selectively binds to a RXR receptor can have an association rate constant between, e.g., $1 \times 10^5$ $M^{-1}$ $s^{-1}$ to $1 \times 10^8$ $M^{-1}$ $s^{-1}$, $1 \times 10^6$ $M^{-1}$ $s^{-1}$ to $1 \times 10^8$ $M^{-1}$ $s^{-1}$, $1 \times 10^5$ $M^{-1}$ $s^{-1}$ to $1 \times 10^7$ $M^{-1}$ $s^{-1}$, or $1 \times 10^6$ $M^{-1}$ $s^{-1}$ to $1 \times 10^7$ $M^{-1}$ $s^{-1}$.

In other aspects of this embodiment, the binding affinity of a RXR agonist that selectively binds to a RXR receptor can have a disassociation rate constant of, e.g., less than $1\times10^{-3}$ $s^{-1}$, less than $1\times10^{-4}$ $s^{-1}$, or less than $1\times10^{-5}$ $s^{-1}$. In another embodiment, the binding affinity of a RXR agonist that selectively binds to a RXR receptor can have a disassociation rate constant of, e.g., more than $1\times10^{-3}$ $s^{-1}$, more than $1\times10^{-4}$ $s^{-1}$, or more than $1\times10^{-5}$ $s^{-1}$. In other aspects, the binding affinity of a RXR agonist that selectively binds to a RXR receptor can have a disassociation rate constant between, e.g., $1\times10^{-3}$ $s^{-1}$ to $1\times10^{-5}$ $s^{-1}$, $1\times10^{-3}$ $s^{-1}$ to $1\times10^{-4}$ $s^{-1}$, or $1\times10^{-4}$ $s^{-1}$ to $1\times10^{-5}$ $s^{-1}$.

In yet other aspects of this embodiment, the binding affinity of a RXR agonist that selectively binds to a RXR receptor can have an equilibrium disassociation constant of less than 100 nM. In aspects of this embodiment, the binding affinity of a RXR agonist that selectively binds to a RXR receptor can have an equilibrium disassociation constant of, e.g., less than 100 nM, less than 90 nM, less than 80 nM, less than 70 nM, less than 60 nM, less than 50 nM, less than 40 nM, less than 30 nM, less than 20 nM, or less than 10 nM. In aspects of this embodiment, the binding affinity of a RXR agonist that selectively binds to a RXR receptor can have an equilibrium disassociation between, e.g., 0.1 nM to 10 nM, 0.1 nM to 50 nM, 0.1 nM to 100 nM, 0.5 nM to 10 nM, 0.5 nM to 50 nM, 0.5 nM to 100 nM, 1 nM to 10 nM, 1 nM to 50 nM, or 1 nM to 100 nM.

In still other aspects of this embodiment, the binding affinity of a RXR agonist that selectively binds to a RXR can have an association rate constant for a RAR receptor of, e.g., less than $1\times10^{0}$ $M^{-1}$ $s^{-1}$, less than $1\times10^{1}$ $M^{-1}$ $s^{-1}$, less than $1\times10^{2}$ $M^{-1}$ $s^{-1}$, less than $1\times10^{3}$ $M^{-1}$ $s^{-1}$, or less than $1\times10^{4}$ $M^{-1}$ $s^{-1}$. In another embodiment, the binding affinity of a RXR agonist that selectively binds to a RXR receptor can have an association rate constant of a RAR receptor of, e.g., at most $1\times10^{0}$ $M^{-1}$ $s^{-1}$, at most $1\times10^{1}$ $M^{-1}$ $s^{-1}$, at most $1\times10^{2}$ $M^{-1}$ $s^{-1}$, at most $1\times10^{3}$ $M^{-1}$ $s^{-1}$, or at most $1\times10^{4}$ $M^{-1}$ $s^{-1}$.

In further aspects of this embodiment, the binding affinity of a RXR agonist that selectively binds to a RXR receptor can have an equilibrium disassociation constant for a RAR receptor of, e.g., more than 500 nM, for than 1,000 nM, more than 5,000 nm, or more than 10,000 nM. In another embodiment, the binding affinity of a RXR agonist that selectively binds to a RXR receptor can have an equilibrium disassociation constant for a RAR receptor between, e.g., 500 nM to 10,000 nM, 1,000 nM to 10,000 nM, or 5,000 nM to 10,000 nM.

Binding specificity is the ability of a RXR agonist to discriminate between a RXR receptor and a receptor that does not contain its binding site, such as, e.g., a RAR receptor. One way to measure binding specificity is to compare the Kon association rate of a RXR agonist for its RXR relative to the Kon association rate of a RXR agonist for a receptor that does not contain its binding site. For example, comparing the association rate constant (Ka) of a RXR agonist for its RXR receptor relative to a RAR receptor.

In aspects of this embodiment, a RXR agonist that selectively binds to a RXR receptor can have an association rate constant (Ka) for a receptor not comprising its binding site of, e.g., less than $1\times10^{0}$ $M^{-1}$ $s^{-1}$, less than $1\times10^{1}$ $M^{-1}$ $s^{-1}$, less than $1\times10^{2}$ $M^{-1}$ $s^{-1}$, less than $1\times10^{3}$ $M^{-1}$ $s^{-1}$ or less than $1\times10^{4}$ $M^{-1}$ $s^{-1}$. In other aspects of this embodiment, a RXR agonist that selectively binds to a RXR receptor can have an association rate constant (Ka) for a receptor not comprising its binding site of, e.g., at most $1\times10^{0}$ $M^{-1}$ $s^{-1}$, at most $1\times10^{1}$ $M^{-1}$ $s^{-1}$, at most $1\times10^{2}$ $M^{-1}$ $s^{-1}$, at most $1\times10^{3}$ $M^{-1}$ $s^{-1}$ or at most $1\times10^{4}$ $M^{-1}$ $s^{-1}$.

In other aspects of this embodiment, a RXR agonist that selectively binds to a RXR receptor can have an association rate constant (Ka) for a receptor not comprising its binding site of, e.g., at least 2-fold more, at least 3-fold more, at least 4-fold more, at least 5-fold more, at least 6-fold more, at least 7-fold more, at least 8-fold more, or at least 9-fold more. In further aspects of this embodiment, a RXR agonist that selectively binds to a RXR receptor can have an association rate constant (Ka) for a receptor not comprising its binding site of, e.g., at least 10-fold more, at least 100-fold more, at least 1,000-fold more or at least 10,000-fold more. In yet other aspects of this embodiment, a RXR agonist that selectively binds to a RXR receptor can have an association rate constant (Ka) for a receptor not comprising its binding site of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, a RXR agonist that selectively binds to a RXR receptor can have an association rate constant (Ka) for a receptor not comprising its binding site of, e.g., at most 10-fold more, at most 100-fold more, at most 1,000-fold more or at most 10,000-fold more.

The binding specificity of a RXR agonist that selectively binds to a RXR receptor can also be characterized as a binding ratio that such a RXR agonist can discriminate its RXR receptor relative to a receptor not comprising its binding site, such as, e.g., a RAR receptor. In aspects of this embodiment, a RXR agonist that selectively binds to a RXR receptor has a binding ratio for its RXR receptor relative to a receptor not comprising its binding site of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In other aspects of this embodiment, a RXR agonist that selectively binds to a RXR receptor has a binding ratio for its RXR receptor relative to a RAR receptor of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

In aspects of this embodiment, a RXR agonist will have a ratio of activity at a RXR receptor relative to a RAR receptor of, e.g., at least 5 greater, at least 10 greater, at least 15, or at least 20 greater.

The binding specificity of a RXR agonist that selectively binds to a RXR receptor can also be characterized as an activity ratio that such a RXR agonist can exert activity through binding to its RXR receptor relative to a receptor not comprising its binding site, such as, e.g., a RAR receptor. In aspects of this embodiment, a RXR agonist that selectively binds to a RXR receptor has an activity ratio through its RXR receptor relative to a receptor not comprising its binding site of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In other aspects of this embodiment, a RXR agonist that selectively binds to a RXR receptor has an activity ratio through its RXR receptor relative to a RAR receptor of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

In an aspect of this embodiment, a RXR agonist is a compound having the structure of formula I:

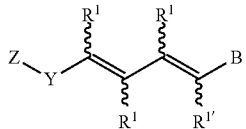

(I)

wherein Z is a radical having the structure of Formula II:

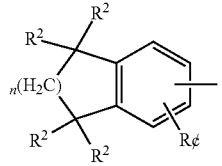

(II)

Y is cycloalkyl or cycloalkenyl of 3 to 8 carbons optionally substituted with one or two $R^4$ groups, or Y is selected from phenyl, pyridyl, thienyl, furyl, pyrrolyl, pyridazinyl, pyrimidiyl, pyrazinyl, thiazolyl, oxazolyl, and imidazolyl, the groups being optionally substituted with one or two $R^4$ groups, the divalent Y radical being substituted by the Z and —$(CR^1$=$CR^1$—$CR^1$=$CR^1)$— groups on adjacent carbons; $R^1$ and $R^2$ independently are H, lower alkyl or fluoroalkyl; $R^3$ is hydrogen, lower alkyl, Cl or Br; $R^4$ is lower alkyl, fluoroalkyl or halogen, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$OCOR^7$, —$CR^7(OR^{12})_2$, —$CR^7OR^{13}O$, or tri-lower alkylsilyl, where $R^7$ is an alkyl, cycloalkyl or alkenyl group, containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, $R^{13}$ is divalent alkyl radical of 2-5 carbons; and n is 1 or 2.

In an aspect of this embodiment, a RXR agonist is a compound having the structure of formula III:

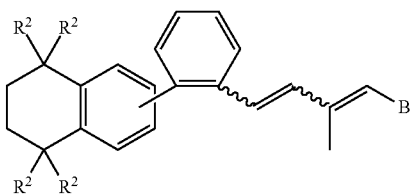

(III)

wherein $R^2$ is hydrogen or lower alkyl; $R^3$ is hydrogen or lower alkyl, and B is hydrogen, COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or tri-lower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

In an aspect of this embodiment, a RXR agonist is a compound having the structure of formula IV:

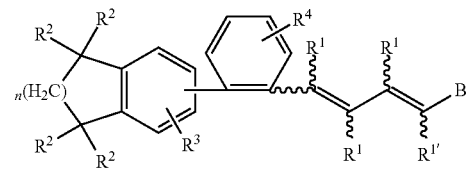

(IV)

wherein n is 1 or 2; $R^1$ and $R^2$ independently are H, lower alkyl or fluoroalkyl; $R^3$ is hydrogen, lower alkyl, Cl or Br; $R^4$ is H, lower alkyl, fluoroalkyl or halogen, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or trilower alkylsilyl where $R^7$ is an alkyl, cycloalkyl or alkenyl group containing 1 to 5 carbons, $R^8$ is an alkyl group of 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

In an aspect of this embodiment, a RXR agonist is a compound having the structure of formula V:

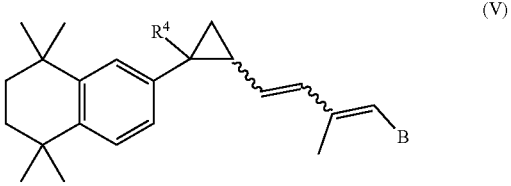

(V)

where $R^4$ is lower alkyl of 1 to 6 carbons; B is —COOH or —$COOR^8$ where $R^8$ is lower alkyl of 1 to 6 carbons, and the configuration about the cyclopropane ring is cis, and the configuration about the double bonds in the pentadienoic acid or ester chain attached to the cyclopropane ring is trans in each of the double bonds, or a pharmaceutically acceptable salt of the compound.

In an aspect of this embodiment, a RXR agonist is a compound having the structure of formula VI:

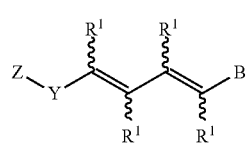

(VI)

wherein Z is a radical having the structure of Formula VII:

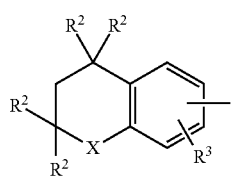
(VII)

Y is cycloalkyl or cycloalkenyl of 3 to 8 carbons optionally substituted with one or two $R^4$ groups, or Y is selected from phenyl, pyridyl, thienyl, furyl, pyrrolyl, pyridazinyl, pyrimidiyl, pyrazinyl, thiazolyl, oxazolyl, and imidazolyl, the groups being optionally substituted with one or two $R^4$ groups, the divalent Y radical being substituted by the Z and —(CR$^1$═CR$^1$—CR$^1$═CR$^1$)— groups on adjacent carbons; X is S or O; $R^1$ and $R^2$ independently are H, lower alkyl or fluoroalkyl; $R^3$ is hydrogen, lower alkyl, Cl or Br; $R^4$ is lower alkyl, fluoroalkyl or halogen, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —OCOR$^7$, —CR$^7$(OR$^{12}$)$_2$, —CR$^7$OR$^{13}$O, or tri-lower alkylsilyl, where $R^7$ is an alkyl, cycloalkyl or alkenyl group, containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

In an aspect of this embodiment, a RXR agonist is a compound having the structure of formula VIII:

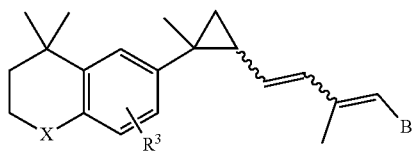
(VIII)

wherein X is S or O; $R^2$ is hydrogen or lower alkyl; $R^3$ is hydrogen or lower alkyl, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

In an aspect of this embodiment, a RXR agonist is a compound having the structure of formula IX:

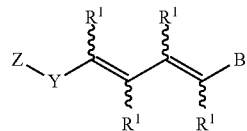
(IX)

wherein Z is a radical having the structure of Formula X:

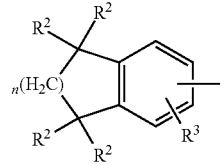
(X)

Y is selected from pyridyl, pyrrolyl, pyridazinyl, pyrimidinyl, pyrazinyl, thiazolyl, oxazolyl, and imidazolyl, the groups being optionally substituted with one or two $R^4$ groups, the divalent Y radical being substituted by the Z and —(CR$^1$═CR$^1$—CR$^1$═CR$^1$)— groups on adjacent carbons; X is NR$^5$; n is 1 or 2; $R^1$ and $R^2$ independently are H, lower alkyl or fluoroalkyl; $R^3$ is hydrogen, lower alkyl, Cl or Br; $R^4$ is lower alkyl, fluoroalkyl or halogen; $R^5$ is H or lower alkyl, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

In an aspect of this embodiment, a RXR agonist is a compound having the structure of formula IX:

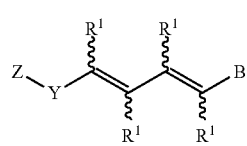
(IX)

wherein Z is a radical having the structure of Formula X:

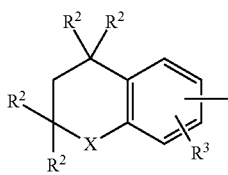
(XI)

Y is selected from pyridyl, pyrrolyl, pyridazinyl, pyrimidinyl, pyrazinyl, thiazolyl, oxazolyl, and imidazolyl, the groups being optionally substituted with one or two $R^4$ groups, the divalent Y radical being substituted by the Z and —$(CR^1=CR^1-CR^1=CR^1)$— groups on adjacent carbons; X is $NR^5$; n is 1 or 2; $R^1$ and $R^2$ independently are H, lower alkyl or fluoroalkyl; $R^3$ is hydrogen, lower alkyl, Cl or Br; $R^4$ is lower alkyl, fluoroalkyl or halogen; $R^5$ is H or lower alkyl, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

In an aspect of this embodiment, a RXR agonist is a compound having the structure of formula XII:

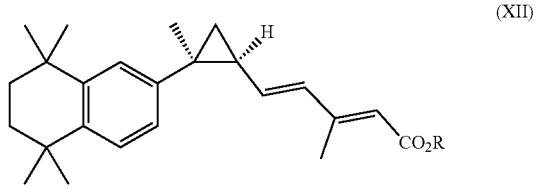

(XII)

wherein R is H, lower alkyl or 1 to 6 carbons, or a pharmaceutically acceptable salt of the compound.

In an aspect of this embodiment, a RXR agonist is a compound having the structure of formula XII:

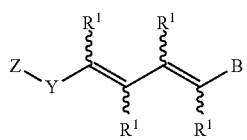

(XIII)

wherein Z is a radical having the structure of Formula XIV:

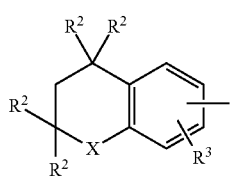

(XIV)

Y is cyclopropyl, the Y group being optionally substituted with one or two $R^4$ groups, the divalent Y radical being substituted by the Z and —$(CR^1=CR^1-CR^1=CR^1)$— groups on adjacent carbons; X is $NR^5$; $R^1$ and $R^2$ independently are H, lower alkyl or fluoalalyl; $R^3$ is hydrogen, lower alkyl, Cl or Br; $R^4$ is lower alkyl, fluoroalkyl or hydrogen; $R^5$ is H or lower alkyl, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

In an aspect of this embodiment, a RXR agonist is a compound having the structure of formula XV:

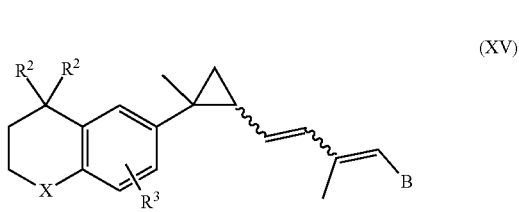

(XV)

wherein X is $NR^5$; $R^5$ is H or lower alkyl; $R^2$ is H or lower alkyl; $R^3$ is H or lower alkyl, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

In an aspect of this embodiment, a RXR agonist is a compound having the structure of formula XVI:

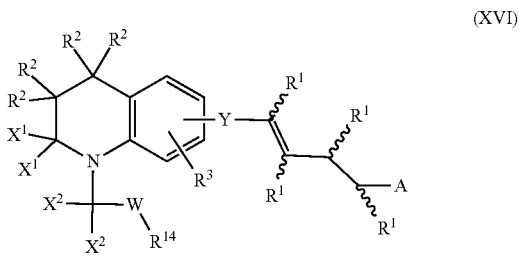

(XVI)

where Y is a bivalent radical having the structure of Formula XVII:

(XVII)

the two $X^1$ groups jointly represent an oxo (=O) or thione (=S) function, or $X^1$ is independently selected from H or alkyl of 1 to 6 carbons; the two $X^2$ groups jointly represent an oxo (=O) or a thione (=S) function, or $X^2$ independently selected from H or alkyl of 1 to 6 carbons, with the proviso that one of the joint $X^1$ grouping or of the joint $X^2$ grouping represents an oxo (═O) or thione (═S) function; W is O, $C(R^1)_2$, or W does not exist; $R^1$ is independently H, lower alkyl of 1 to 6 carbons, or lower fluoroalkyl of 1 to 6 carbons; $R^2$ is independently H, lower alkyl of 1 to 6 carbons, or lower fluoroalkyl of 1 to 6 carbons; $R^3$ is hydrogen, lower alkyl of 1 to 6 carbons, $OR^1$, fluoro substituted lower alkyl of 1 to 6 carbons halogen, $NO_2$, $NH_2$, —NHCO($C_1$-$C_6$) alkyl, or —NHCO($C_1$-$C_6$) alkenyl; A is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CH(OR$^{13}$O), —COR$^7$, —CR$^7$(OR$^{12}$)$_2$, —CR$^7$(OR$^{13}$O), or —Si(C$_1$-C$_6$)$_3$, where $R^7$ is an alkyl, cycloalkyl or alkenyl group containing 1 to 5 carbons, $R^8$ is an alkyl group of 1 to 10 carbons or (trimethylsilyl)alkyl where the alkyl group has 1 to 10 carbons, or a cycloalkyl group of 5 to 10 carbons, or $R^8$ is phenyl or lower alkyphenyl, $R^9$ and $R^{10}$ independently are hydrogen, an alkyl group of 1 to 10 carbons, or a cycloalkyl group of 5-10 carbons, or phenyl, hydroxyphenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons, and $R^{14}$ is H, alkyl of 1 to 10 carbons, fluoro-substituted alkyl of 1 to 10 carbons, alkenyl of 2 to 10 carbons and having 1 to 3 double bonds.

In an aspect of this embodiment, a RXR agonist is a compound having the structure of formula XVIII:

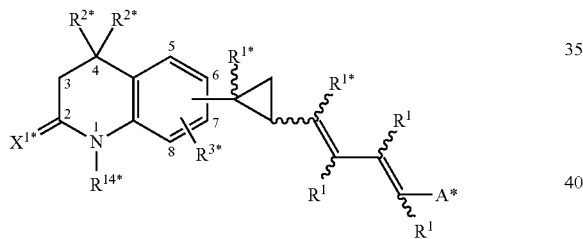

wherein $R^1$ is independently H, lower alkyl of 1 to 6 carbons, or lower fluoroalkyl of 1 to 6 carbons; $R^{1*}$ is hydrogen or $C_{1-6}$-alkyl; $R^{2*}$ is independently H, lower alkyl of 1 to 6 carbons, or lower fluoroalkyl of 1 to 6 carbons; $R^{3*}$ is hydrogen, lower alkyl of 1 to 6 carbons, fluoro substituted lower alkyl of 1 to 6 carbons or halogen; $X^{1*}$ is an oxo (═O) or a thione (═S) group; A* is hydrogen, —COOH or a pharmaceutically acceptable salt thereof, —COOR$^8$, —CONR$^9$R$^{10}$, where $R^8$ is an alkyl group of 1 to 10 carbons or (trimethylsilyl)alkyl where the alkyl group has 1 to 10 carbons, or a cycloalkyl group of 5 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl, hydroxyphenyl or lower alkylphenyl, and the cyclopropyl group is attached to the 6 or 7 position of the tetrahydroquinoline moiety, and $R^{14*}$ is alkyl of 1 to 10 carbons or fluoro-substituted alkyl of 1 to 10 carbons.

In an aspect of this embodiment, a RXR agonist is a compound having the structure of formulae XIX, XX, or XXI:

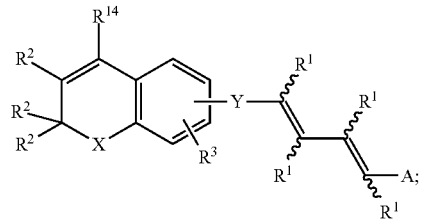

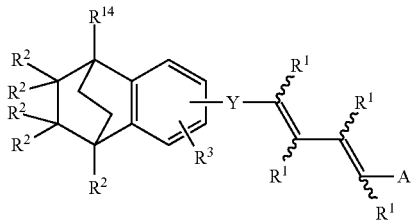

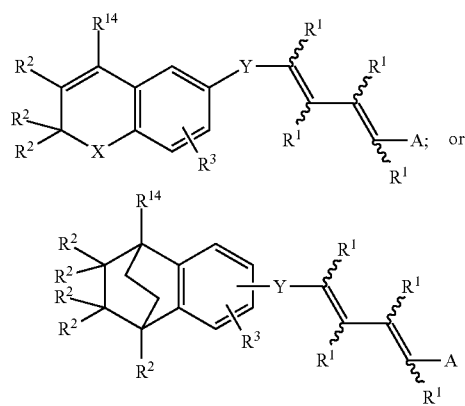

where X is O, S, or $(CR^1R^1)_n$ where n is 0, 1 or 2; Y is a bivalent radical having the structure of Formulae XXII or XXIII where o is an integer between 1 through 4

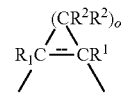

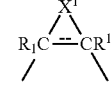

or Y is a bivalent aryl or 5 or 6 membered heteroaryl radical having 1 to 3 heteroatoms selected from N, S and O, the aryl or heteroaryl groups being unsubstituted, or substituted with 1 to 3 $C_{1-6}$ alkyl or with 1 to 3 $C_{1-6}$ fluoroalkyl groups with the proviso that when the compound is in accordance with Formula II then Y is not a 5 or 6 membered ring; $X^1$ is S or NH; $R^1$ is independently H, lower alkyl of 1 to 6 carbons, or lower fluoroalkyl of 1 to 6 carbons; $R^2$ is independently H, lower alkyl of 1 to 6 carbons, $OR^1$, adamantly, or lower fluoroalkyl of 1 to 6 carbons, or the two $R^2$ groups jointly represent an oxo (═O) group with the proviso that when the compound is in accordance with Formula II then at least one of the $R^2$ substituents is branched-chain alkyl or adamantly; $R^3$ is hydrogen, lower alkyl of 1 to 6 carbons, $OR^1$, fluoro substituted lower alkyl of 1 to 6 carbons or halogen, $NO_2$, $NH_2$, —NHCO($C_1$-$C_6$) alkyl, or —NHCO($C_1$-$C_6$) alkenyl; A is —COOH or a pharmaceutically acceptable salt thereof, COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CH(OR$^{13}$O), —COR$^7$, —CR$^7$ (OR$^{12}$)$_2$, CR$^7$(OR$^{13}$O), or —Si(C$_{1-6}$alkyl)$_3$, where $R^7$ is an alkyl, cycloalkyl or alkenyl group containing 1 to 5 carbons, $R^8$ is an alkyl group of 1 to 10 carbons or (trimethylsilyl) alkyl where the alkyl group has 1 to 10 carbons, or a cycloalkyl group of 5 to 10 carbons, or R$^8$ is phenyl or lower alkylphenyl, R$^9$ and R$^{10}$ independently are hydrogen, an alkyl group of 1 to 10 carbons, or a cycloalkyl group of 5-10 carbons, or phenyl, hydroxyphenyl or lower alkylphenyl, R$^{12}$ is lower alkyl, and R$^{13}$ is divalent alkyl radical of 2-5 carbons, and R$^{14}$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$-$C_{10}$-alkylphenyl, naphthyl, $C_1$-$C_{10}$-alkylnaphthyl, phenyl-$C_1$-$C_{10}$-alkyl, naphthyl-$C_1$-$C_{10}$ alkyl, $C_1$-$C_{10}$-alkenylphenyl having 1 to 3 double bonds, $C_1$-$C_{10}$-alkynylphenyl having 1 to 3 triple bonds, phenyl-$C_1$-$C_{10}$ alkenyl having 1 to 3 double bonds, phenyl-$C_1$-$C_{10}$ alkenyl having 1 to 3 triple bonds, hydroxyl alkyl of 1 to 10 carbons, hydroxyalkenyl having 2 to 10 carbons and 1 to 3 double bonds, hydroxyalkynyl having 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds, acyloxyalkyl of 1 to 10 carbons, acyloxy-alkenyl having 2 to 10 carbons and 1 to 3 double bonds, or acyloxyalkynyl of 2 to 10 carbons and 1 to 3 triple bonds where the acyl group is represented by —COR$^8$, or R$^{14}$ is a 5 or 6 membered heteroaryl group having 1 to 3 heteroatoms, the heteroatoms being selected from a group consisting of 0, S, and N, the heteroaryl group being unsubstituted or substituted with a $C_1$-$C_{10}$ alkyl group, with a $C_1$-$C_{10}$ fluoroalkyl group, or with halogen, and the dashed line in Formula XXII represents a bond or absence of a bond.

In an aspect of this embodiment, a RXR agonist is a compound having the structure of formula XXIV:

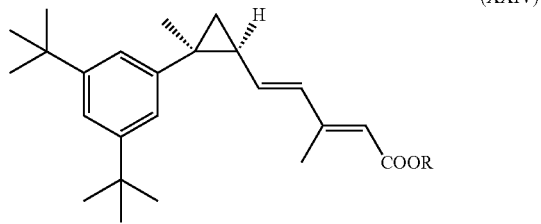

(XXIV)

wherein R is H, lower alkyl of 1 to 6 carbons, or a pharmaceutically acceptable salt of the compound.

In an aspect of this embodiment, a RXR agonist is a compound having the structure of formula XXV:

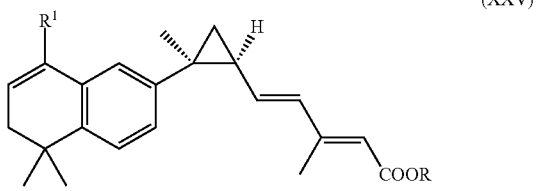

(XXV)

wherein R is H, lower alkyl of 1 to 6 carbons, and R$^1$ is iso-propyl or tertiary-butyl, or a pharmaceutically acceptable salt of the compound.

In an aspect of this embodiment, a RXR agonist is a compound having the structure of formula XXVI:

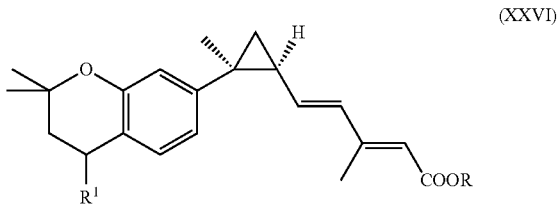

(XXVI)

wherein R is H, lower alkyl of 1 to 6 carbons, and R$^1$ is iso-propyl, n-butyl or tertiary-butyl, or a pharmaceutically acceptable salt of the compound.

In an aspect of this embodiment, a RXR agonist is a compound having the structure of formula XXVII:

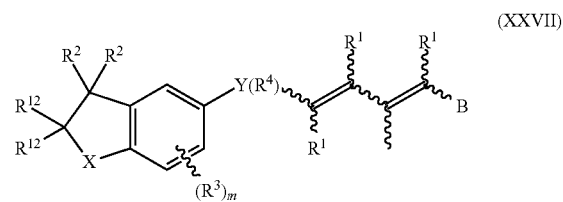

(XXVII)

where X is O or S; Y is a bivalent cycloalkyl or cycloalkenyl radical optionally substituted with one to four R$^4$ groups, the cycloalkenyl radical having 5 to 6 carbons and one double bond, or Y is a bivalent aryl or 5 or 6 membered heteroaryl radical having 1 to 3 heteroatoms selected from N, S and O, the aryl or heteroaryl groups optionally substituted with 1 to 4 R$^4$ groups with the proviso that the cycloalkyl or the cycloalkenyl radical is not substituted on the same carbon with the condensed cyclic moiety and with the diene containing moiety; R$^1$ is independently H, alkyl of 1 to 6 carbons, or fluoroalkyl of 1 to 6 carbons; R$^2$ is independently H, alkyl of 1 to 8 carbons, or fluoroalkyl of 1 to 8 carbons; R$^{12}$ is independently H, alkyl of 1 to 8 carbons, or fluoroalyl of 1 to 8 carbons; R$^3$ is hydrogen, alkyl of 1 to 10 carbons, fluoro substituted alkyl of 1 to 10 carbons, halogen, alkoxy of 1 to 10 carbons, or alkylthio of 1 to 10 carbons; NO$_2$, NH$_2$, —NHCO($C_1$-$C_6$) alkyl, —NHCO($C_1$-$C_6$) alkenyl, —NR$^1$H or N(R$^1$)$_2$, benzyloxy, $C_1$-$C_6$ alkyl-substituted benzyloxy, or R$^3$ is selected from the groups shown below:

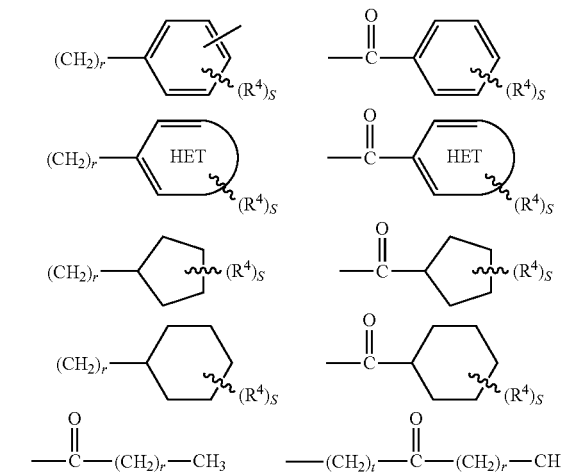

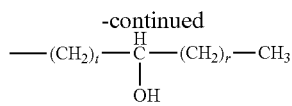

$R^4$ is H, halogen, alkyl of 1 to 10 carbons, fluoro substituted alkyl of 1 to 6 carbons, alkoxy of 1 to 10 carbons, or alkylthio of 1 to 10 carbons; m is an integer having the values of 0 to 3; r is an integer having the values of 1 to 10; s is an integer having the values 1 to 4; t is an integer having the values 1 to 5;

represents a 5 or 6 membered heteroaryl ring having 1 to 3 heteroatoms selected from the group consisting of N, S and O; B is hydrogen, COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl, where R$^7$ is an alkyl, cycloalkyl or alkenyl group containing 1 to 5 carbons, R$^8$ is an alkyl group of 1 to 10 carbons, a cycloalkyl group of 5 to 10 carbons or trimethylsilylalkyl where the alkyl group has 1 to 10 carbons, or R$^8$ is phenyl or lower alkylphenyl, R$^9$ and R$^{10}$ independently are hydrogen, an alkyl group of 1 to 10 carbons, or a cycloalkyl group of 5-10 carbons, or phenyl or lower alkylphenyl, R$^{11}$ is lower alkyl, phenyl or lower alkylphenyl, R$^{12}$ is lower alkyl, and R$^{13}$ is divalent alkyl radical of 2 to 5 carbons.

In an aspect of this embodiment, a RXR agonist is a compound having the structure of formula XXVIII:

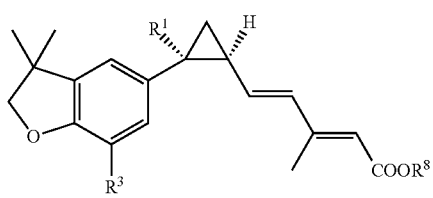

(XXVIII)

wherein R$^1$ is H or methyl; R$^8$ is H, alkyl of 1 to 6 carbons, or a pharmaceutically acceptable cation, and R$^3$ is hydrogen, alkyl of 1 to 10 carbons, halogen, alkoxy of 1 to 10 carbons, or R$^3$ is selected from the groups shown below:

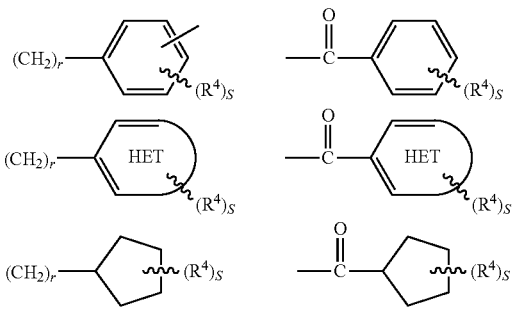

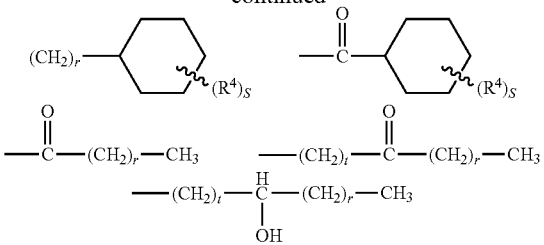

where R$^4$ is H, halogen, alkyl of 1 to 10 carbons, carbons, alkoxy of 1 to 10; r is an integer having the values of 1 to 10; s is an integer having the values 1 to 4;

represents a 5 or 6 membered heteroaryl ring having 1 to 3 heteroatoms selected from the group consisting of N, S and O, and t is an integer having the values 1 to 5.

In an aspect of this embodiment, a RXR agonist is 3,7-dimethyl-6(S),7(S)-methano, 7-[1,1,4,4-tetramethyl-1,2,3,4-tetrahydronaphth-7-yl]2(E),4(E) heptadienoic acid, and has the structure of formula XXIX:

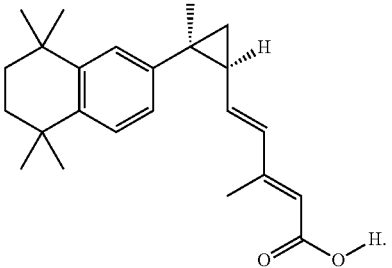

(XXIX)

Aspects of the present specification provide, in part, a RXR agonist having activity that promotes Treg cell differentiation. In aspects of this embodiment, a RXR agonist promotes Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%. In other aspects of this embodiment, a RXR agonist promotes Treg cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%.

In an embodiment, a RXR agonist has activity that results in increased Foxp3 expression in cells exposed to the RXR agonist. In aspects of this embodiment, a RXR agonist increases Foxp3 expression in cells by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same RXR agonist. In other aspects of this embodiment, a RXR agonist increases Foxp3 expression in cells by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to cells not exposed to the same RXR agonist.

In another aspect of this embodiment, a RXR agonist has activity that results in increased Foxp3 expression in naive CD4$^+$ CD25$^-$ FoxP3$^-$ cells cultured under Treg cell differentiation conditions. In other aspects of this embodiment, a RXR agonist increases Foxp3 expression in naive CD4$^+$ OD25$^-$ FoxP3$^-$ cells cultured under Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive CD4$^+$ CD25$^-$ FoxP3$^-$ cells cultured under Treg cell differentiation not exposed to the same RXR agonist. In yet other aspects of this embodiment, a RXR agonist increases Foxp3 expression in naive CD4$^+$ CD25$^-$ FoxP3$^-$ cells cultured under Treg cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to naive CD4$^+$ CD25$^-$ FoxP3$^-$ cells cultured under Treg cell differentiation not exposed to the same RXR agonist.

In an embodiment, a RXR agonist has activity that results in increased α4β7 expression in cells exposed to the RXR agonist. In aspects of this embodiment, a RXR agonist increases α4β7 expression in cells by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same RXR agonist. In other aspects of this embodiment, a RXR agonist increases α4β7 expression in cells by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to cells not exposed to the same RXR agonist.

In another aspect of this embodiment, a RXR agonist has activity that results in increased α4β7 expression in naive CD4$^+$ CD25$^-$ FoxP3$^-$ cells cultured under Treg cell differentiation conditions. In other aspects of this embodiment, a RXR agonist increases α4β7 expression in naive CD4$^+$ CD25$^-$ FoxP3$^-$ cells cultured under Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive CD4$^+$ CD25$^-$ FoxP3$^-$ cells cultured under Treg cell differentiation not exposed to the same RXR agonist. In yet other aspects of this embodiment, a RXR agonist increases α4β7 expression in naive CD4$^+$ CD25$^-$ FoxP3$^-$ cells cultured under Treg cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to naive CD4$^+$ CD25$^-$ FoxP3$^-$ cells cultured under Treg cell differentiation not exposed to the same RXR agonist.

Aspects of the present specification provide, in part, a RXR agonist having activity that inhibits Th17 cell differentiation. In aspects of this embodiment, a RXR agonist inhibits Th17 cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%. In other aspects of this embodiment, a RXR agonist inhibits Th17 cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%.

In an embodiment, a RXR agonist has activity that results in decreased IL-17A expression in cells exposed to the RXR agonist. In aspects of this embodiment, a RXR agonist decreases IL-17A expression in cells by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same RXR agonist. In other aspects of this embodiment, a RXR agonist decreases IL-17A expression in cells by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to cells not exposed to the same RXR agonist.

In another aspect of this embodiment, a RXR agonist has activity that results in decreased IL-17A expression in naive CD4$^+$ CD25$^-$ FoxP3$^-$ cells cultured under Th17 cell differentiation conditions. In other aspects of this embodiment, a RXR agonist decreases IL-17A expression in naive CD4$^+$ CD25$^-$ FoxP3$^-$ cells cultured under Th17 cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive CD4$^+$ CD25$^-$ FoxP3⁻ cells cultured under Th17 cell differentiation not exposed to the same RXR agonist. In yet other aspects of this embodiment, a RXR agonist decreases IL-17A expression in naive CD4⁺ CD25⁻ FoxP3⁻ cells cultured under Th17 cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to naive CD4⁺ CD25⁻ FoxP3⁻ cells cultured under Th17 cell differentiation not exposed to the same RXR agonist.

Aspects of the present specification provide, in part, a RXR agonist having activity that both promotes Treg cell differentiation and inhibits Th17 cell differentiation. In aspects of this embodiment, a RXR agonist promotes Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500% as well as inhibits Th17 cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%. In other aspects of this embodiment, a RXR agonist promotes Treg cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, as well as inhibits Th17 cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%.

In an embodiment, a RXR agonist has activity that results in increased FoxP3 and/or α4β7 expression as well as decreases IL-17A expression in cells exposed to the RXR agonist. In aspects of this embodiment, a RXR agonist increases FoxP3 and/or α4β7 expression in cells by at least 10%, at least 20%, at least 30%, at least 40%, at least 50%, at least 60%, at least 70%, at least 80%, at least 90%, at least 100%, at least 200%, at least 300%, at least 400%, or at least 500%, as well as decreases IL-17A expression in cells by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same RXR agonist. In other aspects of this embodiment, a RXR agonist increases FoxP3 and/or α4β7 expression in cells by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, as well as decreases IL-17A expression in cells by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to cells not exposed to the same RXR agonist.

In another aspect of this embodiment, a RXR agonist has activity that results in increased FoxP3 and/or α4β7 expression in naive CD4⁺ CD25⁻ FoxP3⁻ cells cultured under Treg cell differentiation conditions as well as decreases IL-17A expression in naive CD4⁺ CD25⁻ FoxP3⁻ cells cultured under Th17 cell differentiation conditions. In other aspects of this embodiment, a RXR agonist increases FoxP3 and/or α4β7 expression in naive CD4⁺ CD25⁻ FoxP3⁻ cells cultured under Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive CD4⁺ CD25⁻ FoxP3⁻ cells cultured under Treg cell differentiation not exposed to the same RXR agonist as well as decreases IL-17A expression in naive CD4⁺ CD25⁻ FoxP3⁻ cells cultured under Th17 cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive CD4⁺ CD25⁻ FoxP3⁻ cells cultured under Th17 cell differentiation not exposed to the same RXR agonist.

In yet other aspects of this embodiment, a RXR agonist increases FoxP3 and/or α4β7 expression in naive CD4⁺ CD25⁻ FoxP3⁻ cells cultured under Treg cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to naive CD4⁺ CD25⁻ FoxP3⁻ cells cultured under Treg cell differentiation not exposed to the same RXR agonist as well as decreases IL-17A expression in naive CD4⁺ CD25⁻ FoxP3⁻ cells cultured under Th17 cell differentiation by about 10% to about 25%, about 10% to about 50%, about 10% to about 75%, about 10% to about 100%, about 10% to about 200%, about 10% to about 300%, about 10% to about 400%, about 10% to about 500%, about 25% to about 50%, about 25% to about 75%, about 25% to about 100%, about 25% to about 200%, about 25% to about 300%, about 25% to about 400%, about 25% to about 500%, about 50% to about 100%, about 50% to about 200%, about 50% to about 300%, about 50% to about 400%, or about 50% to about 500%, relative to naive CD4⁺ CD25⁻ FoxP3⁻ cells cultured under Th17 cell differentiation not exposed to the same RXR agonist.

Aspects of the present specification provide, in part, a composition comprising a RXR agonist. A RXR agonist includes the compounds disclosed herein. The compositions disclosed herein may, or may not, comprise any number and combination of compounds disclosed herein. For instance, a composition can comprise, e.g., two or more compounds disclosed herein, three or more compounds disclosed herein, four or more compounds disclosed herein, or five or more compounds disclosed herein.

A compound disclosed herein, or a composition comprising such a compound, is generally administered to an individual as a pharmaceutical composition. Pharmaceutical compositions may be prepared by combining a therapeutically effective amount of at least one compound as disclosed herein, or a pharmaceutically acceptable acid addition salt thereof, as an active ingredient, with conventional acceptable pharmaceutical excipients, and by preparation of unit dosage forms suitable for therapeutic use. As used herein, the term "pharmaceutical composition" and refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition produced using the methods disclosed herein may be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phase, such as, e.g., an emulsion. A pharmaceutical composition disclosed herein intended for such administration may be prepared according to any method known to the art for the manufacture of pharmaceutical compositions.

Liquid formulations suitable for parenteral injection may comprise physiologically acceptable sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Semi-solid formulations suitable for topical administration include, without limitation, ointments, creams, salves, and gels. In such solid formulations, the active compound may be admixed with at least one inert customary excipient (or carrier) such as, a lipid and/or polyethylene glycol.

Solid formulations suitable for oral administration include capsules, tablets, pills, powders and granules. In such solid formulations, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

In liquid and semi-solid formulations, a concentration of a therapeutic compound disclosed herein typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In semi-solid and solid formulations, an amount of a therapeutic compound disclosed herein typically may be between about 0.01% to about 45% by weight. In aspects of this embodiment, an amount of a therapeutic compound disclosed herein may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

A compound disclosed herein, or a composition comprising such a compound, may also be incorporated into a drug delivery platform in order to achieve a controlled compound release profile over time. Such a drug delivery platform comprises a compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hyrophilic and Hydrophobic Agents, U.S. Pat. No. 7,048,946; Hughes, et. al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform releases a compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present invention provide, in part, an autoimmune disorder. An autoimmune disorder arises from an overactive immune response of the body against substances and tissues normally present in the body resulting in a break in tolerance toward self-antigens. In other words, the body actually attacks its own cells because the immune system mistakes some part of the body as a pathogen and attacks it. Characterized by the development of pathogenic T cell populations infiltrating the target organ or tissue, autoimmune disorders may be restricted to certain organs or involve a particular tissue in different places.

Autoimmune diseases can be broadly divided into systemic and organ-specific autoimmune disorders, depending on the principal clinico-pathologic features of each disease. Systemic autoimmune diseases include, without limitation, systemic lupus erythematosus (SLE), Sjögren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Non-limiting examples of an autoimmune disorder that can be treated using a compound or a composition disclosed herein include an acute disseminated encephalomyelitis (ADEM), an Addison's disease, an allergy, allergic rhinitis, an Alzheimer's disease, an anti-phospholipid antibody syndrome (APS), an arthritis such as, e.g., a monoarthritis, an oligoarthritis, or a polyarthritis like an osteoarthritis, a rheumatoid arthritis, a juvenile idiopathic arthritis, a septic arthritis, a spondyloarthropathy, a gout, a pseudogout, or Still's disease, an asthma, an autoimmune deficiency syndrome (AIDS), an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an endometriosis, a gastrointestinal disorder such as, e.g., an irritable bowel disease or an inflammatory bowel disease like Crohn's disease or an ulcerative colitis, a Goodpasture's syndrome, a Graves' disease, a Guillain-Barré syndrome (GBS), a Hashimoto's thyroiditis, a hidradenitis suppurativa, an idiopathic thrombocytopenic purpura, an interstitial cystitis, a lupus, such as, e.g., a discoid lupus erythematosus, a drug-induced lupus erythematosus, a lupus nephritis, a neonatal lupus, a subacute cutaneous lupus erythematosus, or a systemic lupus erythematosus, a morphea, a multiple sclerosis (MS), a myasthenia gravis, a myopathy such as, e.g., a dermatomyositis, an inclusion body myositis, or a polymyositis, a myositis, a narcolepsy, a neuromyotonia, a Parkinson's disease, a pemphigus vulgaris, a pernicious anaemia, a primary biliary cirrhosis, a psoriasis, a recurrent disseminated encephalomyelitis, a rheumatic fever, a schizophrenia, a scleroderma, a Sjögren's syndrome, a skin disorder such as, e.g., dermatitis, an eczema, a statis dermatitis, a hidradenitis suppurativa, a psoriasis, a rosacea or a scleroderma, a tenosynovitis, a uveitis, vasculitis such as, e.g., a Buerger's disease, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a microscopic polyarteritis/polyangiitis, a polyarteritis nodosa, a polymyalgia rheumatica (PMR), a rheumatoid vasculitis, a Takayasu arteritis, or a Wegener's granulomatosis, or a vitiligo. See Pamela D. Van Schaack & Kenneth L. Tong, Treatment of Autoimmune Disorder with a Neurotoxin, U.S. Patent Publication 2006/138059, which is hereby incorporated by reference in its entirety.

One type of autoimmune disorder is an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple's disease and Behcet's disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

Another type of autoimmune disorder is a myopathy. Myopathies are caused by problems with the immune system attacking components of the muscle, leading to signs of inflammation in the muscle Inflammatory myopathies include, without limitation, dermatomyositis, inclusion body myositis, and polymyositis.

Another type of autoimmune disorder is a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behcet's disease, or other connective tissue disorders, vasculitis secondary to viral infection.

Another type of autoimmune disorder is a skin disorder. Skin disorders include, without limitation, a dermatitis, including chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, psoriasis including plaqure psoriasis, nail psoriasis, guttate psoriasis, scalp psoriasis, inverse psoriasis, pustular psoriasis, and erythrodermis psoriasis, rosacea and scleroderma including morphea.

Another type of autoimmune disorder is a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

Aspects of the present invention provide, in part, a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T cell mediated and humoral immune (antibodies) mechanisms. The number of mismatched alleles determines the speed and magnitude of the rejection response. Different mechanisms tend to act against different transplants.

A transplant rejection can be classified as a hyperacute rejection, an acute rejection, or a chronic rejection. Hyperacute rejection is a complement-mediated response in recipients with pre-existing antibodies to the donor (for example, ABO blood type antibodies). Hyperacute rejection occurs within minutes after the transplant and must be immediately removed to prevent a severe systemic inflammatory response. Rapid agglutination of the blood occurs.

Acute rejection may begin as early as one week after transplantation (as opposed to hyperacute rejection, which is immediate). The risk of acute rejection is highest in the first three months after transplantation. However, acute rejection can also occur months to years after transplantation. The reason that acute rejection usually begins one week after transplantation is that T-cells are involved in the rejection mechanism. These T-cells must differentiate before rejection begins. The T-cells cause cells in the transplanted tissue to lyse, or produce cytokines that cause necrosis of the transplanted tissue. A single episode of acute rejection is not a cause for concern if recognized and treated promptly, and rarely leads to organ failure. Acute rejection occurs to some degree in all transplants (except those between identical twins) unless the immune response in altered through the use of immunosuppressive drugs. It is caused by mismatched HLA, which are present on all cells of the body. There are a large number of different alleles of each HLA, so a perfect match between all HLA in the donor tissue and the recipient's body is extremely rare.

Chronic rejection of a transplanted organ or tissue is where the rejection is due to a poorly understood chronic inflammatory and immune response against the transplanted tissue. Chronic rejection after lung transplantation is the leading cause of long-term morbidity and mortality in lung transplant patients Also included in the term "transplant rejection" is a graft-versus-host disease (GVHD). GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. The acute or fulminant form of the disease (aGVHD) is normally observed within the first 100 days post-transplant,[2] and is a major challenge to transplants owing to associated morbidity and mortality. The chronic form of graft-versus-host-disease (cGVHD) normally occurs after 100 days. The appearance of moderate to severe cases of cGVHD adversely influences long-term survival. Acute and chronic GVHD appear to involve different immune cell subsets, different cytokine profiles, somewhat different host targets, and respond differently to treatment.

Acute GVHD is characterized by selective damage to the liver, skin and mucosa, gastrointestinal tract, immune system (the hematopoietic system, e.g., the bone marrow and the thymus) itself, and the lungs in the form of idiopathic pneumonitis. Acute GVHD of the GI tract can result in severe intestinal inflammation, sloughing of the mucosal membrane, severe diarrhea, abdominal pain, nausea, and vomiting. This is typically diagnosed via intestinal biopsy. Liver GVHD is measured by the bilirubin level in acute patients. Skin GVHD results in a diffuse maculopapular rash, sometimes in a lacy pattern. Acute GVHD is staged as follows: overall grade (skin-liver-gut) with each organ staged individually from a low of 1 to a high of 4. Patients with grade IV GVHD usually have a poor prognosis. If the GVHD is severe and requires intense immunosuppression involving steroids and additional agents to get under control, the patient may develop severe infections as a result of the immunosuppression and may die of infection. Chronic GVHD also attacks the above organs, but over its long-term course can also cause damage to the connective tissue and exocrine glands.

Aspects of the present invention provide, in part, reducing a symptom associated with an autoimmune disorder or transplant rejection. The actual symptoms associated with an autoimmune disorder or transplant rejection disclosed herein are well known and can be determined by a person of ordinary skill in the art by taking into account factors, including, without limitation, the location of the autoimmune disorder or transplant rejection, the cause of the autoimmune disorder or transplant rejection, the severity of the autoimmune disorder or transplant rejection, the tissue or organ affected by the autoimmune disorder or transplant rejection, and the autoimmune disorder or transplant rejection associated with the inflammation. Non-limiting examples of a symptom reduced by a method of treating an autoimmune disorder or transplant rejection disclosed herein include inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disorder or transplant rejection, an increase in the size of an organ or tissue, or the destruction of an organ or tissue. Non-limiting examples of an inflammation symptom reduced by a method of treating an autoimmune disorder disclosed herein include edema, hyperemia, erythema, bruising, tenderness, stiffness, swollenness, fever, a chill, congestion of the respiratory tract including nose and/or bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

Aspects of the present invention provide, in part, a mammal. A mammal includes a human, and a human can be a patient. Other aspects of the present invention provide, in part, an individual. An individual includes a mammal and a human, and a human can be a patient.

Aspects of the present invention provide, in part, administering a compound or a composition disclosed herein. As used herein, the term "administering" means any delivery mechanism that provides a compound or a composition disclosed herein to an individual that potentially results in a clinically, therapeutically, or experimentally beneficial result.

Administration of a compound or a composition disclosed herein include a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A compound or a composition disclosed herein can be administered to a mammal using a variety of routes. Routes of administration suitable for treating an autoimmune disorder or transplant rejection as disclosed herein include both local and systemic administration. Local administration results in significantly more delivery of a composition to a specific location as compared to the entire body of the mammal, whereas, systemic administration results in delivery of a composition to essentially the entire body of the individual. Routes of administration suitable for or treating an autoimmune disorder or transplant rejection as disclosed herein also include both central and peripheral administration. Central administration results in delivery of a compound or a composition to essentially the central nervous system of the individual and includes, e.g., intrathecal administration, epidural administration as well as a cranial injection or implant. Peripheral administration results in delivery of a compound or a composition to essentially any area of an individual outside of the central nervous system and encompasses any route of administration other than direct administration to the spine or brain. The actual route of administration of a compound or a composition disclosed herein used can be determined by a person of ordinary skill in the art by taking into account factors, including, without limitation, the type of an autoimmune disorder or transplant rejection, the location of the autoimmune disorder or transplant rejection, the cause of the autoimmune disorder or transplant rejection, the severity of the autoimmune disorder or transplant rejection, the duration of treatment desired, the degree of relief desired, the duration of relief desired, the particular compound or composition used, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof. An effective dosage amount of a compound or a composition disclosed herein can thus readily be determined by the person of ordinary skill in the art considering all criteria and utilizing his best judgment on the individual's behalf.

In an embodiment, a compound or a composition disclosed herein is administered systemically to a mammal. In another embodiment, a compound or a composition disclosed herein is administered locally to a mammal. In an aspect of this embodiment, a compound or a composition disclosed herein is administered to a site of autoimmune disorder or transplant rejection of a mammal. In another aspect of this embodiment, a compound or a composition disclosed herein is administered to the area surrounding an autoimmune disorder or transplant rejection of a mammal.

Aspects of the present specification provide, in part, administering a therapeutically effective amount of a compound or a composition disclosed herein. As used herein, the term "therapeutically effective amount" is synonymous with "therapeutically effective dose" and when used in reference to treating an autoimmune disorder means the minimum dose of a compound or composition disclosed herein necessary to achieve the desired therapeutic effect and includes a dose sufficient to reduce a symptom associated with an autoimmune disorder or transplant rejection. In aspects of this embodiment, a therapeutically effective amount of a compound or a composition disclosed herein reduces a symptom associated with an autoimmune disorder or transplant rejection by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a compound or a composition disclosed herein reduces a symptom associated with an autoimmune disorder or transplant rejection by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a compound or a composition disclosed herein reduces a symptom associated with an autoimmune disorder or transplant rejection by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a compound or a composition disclosed herein is the dosage sufficient to reduces a symptom associated with an autoimmune disorder or transplant rejection for, e.g., at least one week, at least one month, at least two months, at least three months, at least four months, at least five months, at least six months, at least seven months, at least eight months, at least nine months, at least ten months, at least eleven months, or at least twelve months.

The amount of active component in a compound or a composition disclosed herein for treating an autoimmune disorder or transplant rejection can be varied so that a suitable dosage is obtained. The actual therapeutically effective amount of a compound or a composition disclosed herein to be administered to a mammal can be determined by a person of ordinary skill in the art by taking into account factors, including, without limitation, the type of the autoimmune disorder or transplant rejection, the location of the autoimmune disorder or transplant rejection, the cause of the autoimmune disorder or transplant rejection, the severity of the autoimmune disorder or transplant rejection, the duration of treatment desired, the degree of relief desired, the duration of relief desired, the particular compound or composition used, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof. An effective dosage amount of a compound or a composition disclosed herein can thus readily be determined by the person of ordinary skill in the art considering all criteria and utilizing his best judgment on the individual's behalf.

Additionally, where repeated administration of a compound or a composition disclosed herein is used, the actual effect amount of a compound or a composition disclosed herein will further depend upon factors, including, without limitation, the frequency of administration, the half-life of the compound or composition disclosed herein, or any combination thereof. In is known by a person of ordinary skill in the art that an effective amount of a compound or a composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering a compound or a composition disclosed herein to a mammal, a therapeutically effective amount generally is in the range of about 0.001 mg/kg/day to about 100.0 mg/kg/day. In aspects of this embodiment, an effective amount of a compound or a composition disclosed herein can be, e.g., about 0.01 mg/kg/day to about 0.1 mg/kg/day, about 0.03 mg/kg/day to about 3.0 mg/kg/day, about 0.1 mg/kg/day to about 3.0 mg/kg/day, or about 0.3 mg/kg/day to about 3.0 mg/kg/day. In yet other aspects of this embodiment, a therapeutically effective amount of a compound or a composition disclosed herein can be, e.g., at least 0.001 mg/kg/day, at least 0.01 mg/kg/day, at least 0.1 mg/kg/day, at least 1.0 mg/kg/day, at least 10 mg/kg/day, or at least 100 mg/kg/day. In yet other aspects of this embodiment, a therapeutically effective amount of a compound or a composition disclosed herein can be, e.g., at most 0.001 mg/kg/day, at most 0.01 mg/kg/day, at most 0.1 mg/kg/day, at most 1.0 mg/kg/day, at most 10 mg/kg/day, or at most 100 mg/kg/day.

As another non-limiting example, when administering a compound or a composition disclosed herein to a mammal, a therapeutically effective amount generally is in the range of about 0.001 mg/m$^2$/day to about 100.0 mg/m$^2$/day. In aspects of this embodiment, an effective amount of a compound or a composition disclosed herein can be, e.g., about 0.01 mg/m$^2$/day to about 0.1 mg/m$^2$/day, about 0.03 mg/m$^2$/ day to about 3.0 mg/m²/day, about 0.1 mg/m²/day to about 3.0 mg/m²/day, or about 0.3 mg/m²/day to about 3.0 mg/m²/day. In yet other aspects of this embodiment, a therapeutically effective amount of a compound or a composition disclosed herein can be, e.g., at least 0.001 mg/m²/day, at least 0.01 mg/m²/day, at least 0.1 mg/m²/day, at least 1.0 mg/m²/day, at least 10 mg/m²/day, or at least 100 mg/m²/day. In yet other aspects of this embodiment, a therapeutically effective amount of a compound or a composition disclosed herein can be, e.g., at most 0.001 mg/m²/day, at most 0.01 mg/m²/day, at most 0.1 mg/m²/day, at most 1.0 mg/m²/day, at most 10 mg/m²/day, or at most 100 mg/m²/day.

Dosing can be single dosage or cumulative (serial dosing), and can be readily determined by one skilled in the art. For instance, treatment of an autoimmune disorder or transplant rejection may comprise a one-time administration of an effective dose of a compound or a composition disclosed herein. As a non-limiting example, an effective dose of a compound or a composition disclosed herein can be administered once to a mammal, e.g., as a single injection or deposition at or near the site exhibiting a symptom of an autoimmune disorder or transplant rejection or a single oral administration of the compound or a composition. Alternatively, treatment of an autoimmune disorder or transplant rejection may comprise multiple administrations of an effective dose of a compound or a composition disclosed herein carried out over a range of time periods, such as, e.g., daily, once every few days, weekly, monthly or yearly. As a non-limiting example, a compound or a composition disclosed herein can be administered once or twice weekly to a mammal. The timing of administration can vary from mammal to mammal, depending upon such factors as the severity of a mammal's symptoms. For example, an effective dose of a compound or a composition disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a compound or a composition disclosed herein that is administered can be adjusted accordingly.

A compound or a composition disclosed herein as disclosed herein can also be administered to a mammal in combination with other therapeutic compounds to increase the overall therapeutic effect of the treatment. The use of multiple compounds to treat an indication can increase the beneficial effects while reducing the presence of side effects.

Aspects of the present specification may also be described as follows:

1. A method of treating an autoimmune disorder, the method comprising the step of administering to an individual in need thereof a therapeutically effective amount of a RXR agonist, wherein administration of the RXR agonist reduces a symptom associated with the autoimmune disorder, thereby treating the individual.

2. A method of treating inflammation as a result of an autoimmune disorder, the method comprising the step of administering to an individual in need thereof a therapeutically effective amount of a RXR agonist, wherein administration of the compound or composition reduces a symptom associated with inflammation, thereby treating the individual.

3. A method of treating a transplant rejection, the method comprising the step of administering to an individual in need thereof a therapeutically effective amount of a RXR agonist, wherein administration of the RXR agonist reduces a symptom associated with the transplant rejection, thereby treating the individual.

4. Use of a RXR agonist in the manufacture of a medicament in the treatment of an autoimmune disorder, an inflammation as a result of an autoimmune disorder, and/or a transplant rejection.

5. Use of a RXR agonist to treat an autoimmune disorder, an inflammation as a result of an autoimmune disorder, or a transplant rejection, wherein administration of the RXR agonist reduces a symptom associated with the autoimmune disorder or transplant rejection, thereby treating the individual.

6. The method or use according to any one of embodiments 1-5, wherein the RXR agonist is a compound having the structure of formula I:

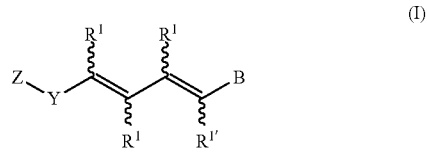

wherein Z is a radical shown in Formula II:

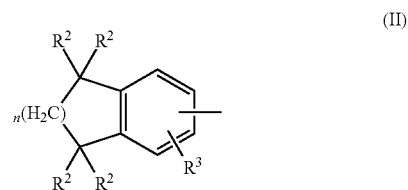

Y is cycloalkyl or cycloalkenyl of 3 to 8 carbons optionally substituted with one or two $R^4$ groups, or Y is selected from phenyl, pyridyl, thienyl, furyl, pyrrolyl, pyridazinyl, pyrimidiyl, pyrazinyl, thiazolyl, oxazolyl, and imidazolyl, the groups being optionally substituted with one or two $R^4$ groups, the divalent Y radical being substituted by the Z and —($CR^1$=$CR^1$=$CR^1$=$CR^1$)— groups on adjacent carbons; $R^1$ and $R^2$ independently are H, lower alkyl or fluoroalkyl; $R^3$ is hydrogen, lower alkyl, Cl or Br; $R^4$ is lower alkyl, fluoroalkyl or halogen, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$OCOR^7$, —$CR^7(OR^{12})_2$, —$CR^7OR^{13}O$, or tri-lower alkylsilyl, where $R^7$ is an alkyl, cycloalkyl or alkenyl group, containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons; and n is 1 or 2.

7. The method or use according to any one of embodiments 1-5, wherein the RXR agonist is a compound having the structure of formula I:

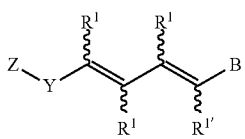

(I)

wherein Z is a radical shown in Formula II:

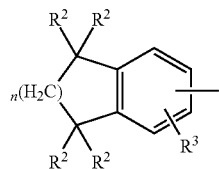

(II)

Y is selected from thienyl and furyl, the groups being optionally with one or two $R^4$ groups, the divalent Y radical being substituted by the Z and —($CR^1$=$CR^1$—$CR^1$=$CR^1$)— groups on adjacent carbons; $R^1$ and $R^2$ independently are H, lower alkyl or fluoroalkyl; $R^3$ is hydrogen, lower alkyl, Cl or Br; $R^4$ is lower alkyl, fluoroalkyl or halogen, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —OCOR$^7$, —CR$^7$(OR$^{12}$)$_2$, —CR$^7$OR$^{13}$O, or tri-lower alkylsilyl, where $R^7$ is an alkyl, cycloalkyl or alkenyl group, containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ carbons, or a cycloalkyl groups of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons; and n is 1 or 2.

8. The method or use according to any one of embodiments 1-7, wherein the RXR agonist is a compound having the structure of formula III:

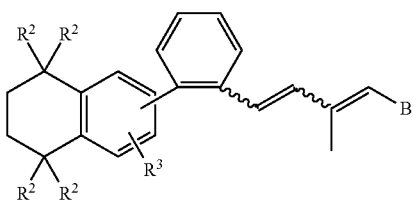

(III)

wherein $R^2$ is hydrogen or lower alkyl; $R^3$ is hydrogen or lower alkyl, and B is hydrogen, COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or tri-lower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

9. The method or use according to any one of embodiments 1-8, wherein the RXR agonist is a compound having the structure of formula IV:

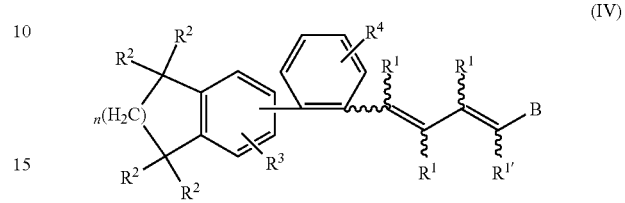

(IV)

wherein n is 1 or 2; $R^1$ and $R^2$ independently are H, lower alkyl or fluoroalkyl; $R^3$ is hydrogen, lower alkyl, Cl or Br; $R^4$ is H, lower alkyl, fluoroalkyl or halogen, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl where $R^7$ is an alkyl, cycloalkyl or alkenyl group containing 1 to 5 carbons, $R^8$ is an alkyl group of 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

10. The method or use according to any one of embodiments 1-9, wherein the RXR agonist is a compound having the structure of formula V:

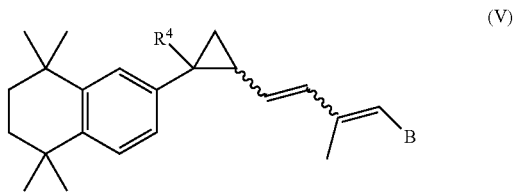

(V)

where $R^4$ is lower alkyl of 1 to 6 carbons; B is —COOH or —COOR$^8$ where $R^8$ is lower alkyl of 1 to 6 carbons, and the configuration about the cyclopropane ring is cis, and the configuration about the double bonds in the pentadienoic acid or ester chain attached to the cyclopropane ring is trans in each of the double bonds, or a pharmaceutically acceptable salt of the compound.

11. The method or use according to any one of embodiments 1-10, wherein the RXR agonist is a compound having the structure of formula VI:

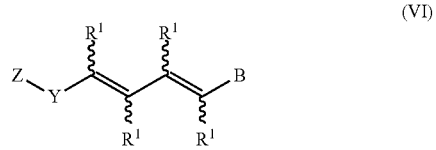

(VI)

wherein Z is a radical shown in Formula VII:

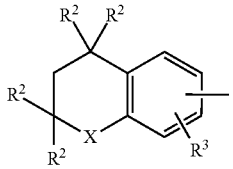
(VII)

Y is cycloalkyl or cycloalkenyl of 3 to 8 carbons optionally substituted with one or two $R^4$ groups, or Y is selected from phenyl, pyridyl, thienyl, furyl, pyrrolyl, pyridazinyl, pyrimidiyl, pyrazinyl, thiazolyl, oxazolyl, and imidazolyl, the groups being optionally substituted with one or two $R^4$ groups, the divalent Y radical being substituted by the Z and —($CR^1$=$CR^1$—$CR^1$=$CR^1$)— groups on adjacent carbons; X is S or O; $R^1$ and $R^2$ independently are H, lower alkyl or fluoroalkyl; $R^3$ is hydrogen, lower alkyl, Cl or Br; $R^4$ is lower alkyl, fluoroalkyl or halogen, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$OCOR^7$, —$CR^7(OR^{12})_2$, —$CR^7OR^{13}O$, or tri-lower alkylsilyl, where $R^7$ is an alkyl, cycloalkyl or alkenyl group, containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

12. The method or use according to any one of embodiments 1-11, wherein the RXR agonist is a compound having the structure of formula VIII:

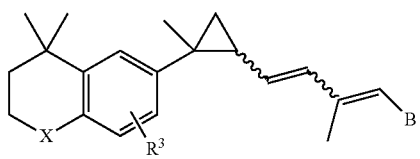
(VII)

wherein X is S or O; $R^2$ is hydrogen or lower alkyl; $R^3$ is hydrogen or lower alkyl, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2-5 carbons.

13. The method or use according to any one of embodiments 1-12, wherein the RXR agonist is a compound having the structure of formula IX:

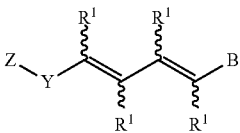
(VI)

wherein Z is a radical shown in Formula X:

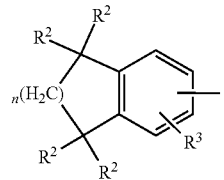
(X)

Y is selected from pyridyl, pyrrolyl, pyridazinyl, pyrimidinyl, pyrazinyl, thiazolyl, oxazolyl, and imidazolyl, the groups being optionally substituted with one or two $R^4$ groups, the divalent Y radical being substituted by the Z and —($CR^1$=$CR^1$—$CR^1$=$CR^1$)— groups on adjacent carbons; X is $NR^5$; n is 1 or 2; $R^1$ and $R^2$ independently are H, lower alkyl or fluoroalkyl; $R^3$ is hydrogen, lower alkyl, Cl or Br; $R^4$ is lower alkyl, fluoroalkyl or halogen; $R^5$ is H or lower alkyl, and B is hydrogen, —COOH or a pharmaceutically acceptable salt thereof, —$COOR^8$, —$CONR^9R^{10}$, —$CH_2OH$, —$CH_2OR^{11}$, —$CH_2OCOR^{11}$, —CHO, —$CH(OR^{12})_2$, —$CHOR^{13}O$, —$COR^7$, —$CR^7(OR^{12})_2$, —$CR^7OR^{13}O$, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

14. The method or use according to any one of embodiments 1-13, wherein the RXR agonist is a compound having the structure of formula IX:

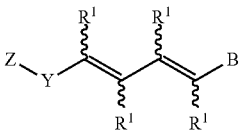
(IX)

wherein Z is a radical shown in Formula XI:

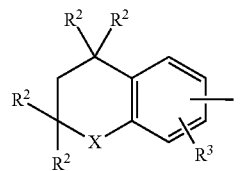
(XI)

Y is selected from pyridyl, pyrrolyl, pyridazinyl, pyrimidinyl, pyrazinyl, thiazolyl, oxazolyl, and imidazolyl, the groups being optionally substituted with one or two $R^4$ groups, the divalent Y radical being substituted by the Z and —(CR$^1$=CR$^1$—CR$^1$=CR$^1$)— groups on adjacent carbons; X is NR$^5$; n is 1 or 2; $R^1$ and $R^2$ independently are H, lower alkyl or fluoroalkyl; $R^3$ is hydrogen, lower alkyl, Cl or Br; $R^4$ is lower alkyl, fluoroalkyl or halogen; $R^5$ is H or lower alkyl, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

15. The method or use according to any one of embodiments 1-14, wherein the RXR agonist is a compound having the structure of formula XII:

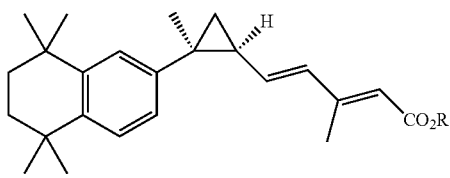

(XII)

wherein R is H, lower alkyl or 1 to 6 carbons, or a pharmaceutically acceptable salt of the compound.

16. The method or use according to any one of embodiments 1-5, wherein the RXR agonist is a compound having the structure of formula XII:

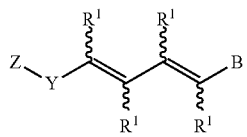

(XIII)

wherein Z is a radical shown in Formula XIV:

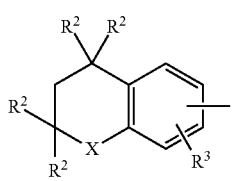

(XIV)

Y is cyclopropyl, the Y group being optionally substituted with one or two $R^4$ groups, the divalent Y radical being substituted by the Z and —(CR$^1$=CR$^1$—CR$^1$=CR$^1$)— groups on adjacent carbons; X is NR$^5$; $R^1$ and $R^2$ independently are H, lower alkyl or fluoroalyl; $R^3$ is hydrogen, lower alkyl, Cl or Br; $R^4$ is lower alkyl, fluoroalkyl or hydrogen; $R^5$ is H or lower alkyl, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

17. The method or use according to any one of embodiments 1-16, wherein the RXR agonist is a compound having the structure of formula XV:

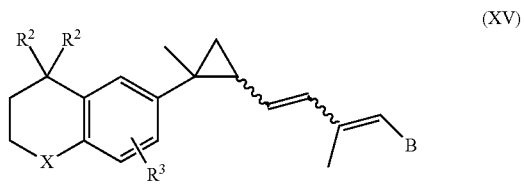

(XV)

wherein X is NR$^5$; $R^5$ is H or lower alkyl; $R^2$ is H or lower alkyl; $R^3$ is H or lower alkyl, and B is hydrogen, —COOH or a pharmaceutically acceptable salt thereof, —COOR$^8$, —CONR$^9$R$^{10}$, —CH$_2$OH, —CH$_2$OR$^{11}$, —CH$_2$OCOR$^{11}$, —CHO, —CH(OR$^{12}$)$_2$, —CHOR$^{13}$O, —COR$^7$, —CR$^7$(OR$^{12}$)$_2$, —CR$^7$OR$^{13}$O, or trilower alkylsilyl, where $R^7$ is an alkyl, cycloalkyl or alkenyl group containing 1 to 5 carbons, $R^8$ is an alkyl group of 1 to 10 carbons, a cycloalkyl group of 5 to 10 carbons or trimethylsilylalkyl where the alkyl group has 1 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons.

18. The method or use according to any one of embodiments 1-17, wherein the RXR agonist is a compound having the structure of formula XVI:

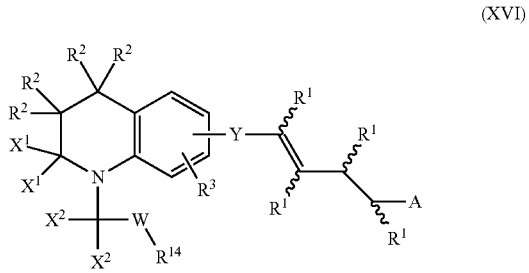

(XVI)

where Y is a bivalent radical having Formula XVII:

(XVII)

the two X¹ groups jointly represent an oxo (═O) or thione (═S) function, or X¹ is independently selected from H or alkyl of 1 to 6 carbons; the two X² groups jointly represent an oxo (═O) or a thione (═S) function, or X² independently selected from H or alkyl of 1 to 6 carbons, with the proviso that one of the joint X¹ grouping or of the joint X² grouping represents an oxo (═O) or thione (═S) function; W is O, $C(R^1)_2$, or W does not exist; $R^1$ is independently H, lower alkyl of 1 to 6 carbons, or lower fluoroalkyl of 1 to 6 carbons; $R^2$ is independently H, lower alkyl of 1 to 6 carbons, or lower fluoroalkyl of 1 to 6 carbons; $R^3$ is hydrogen, lower alkyl of 1 to 6 carbons, $OR^1$, fluoro substituted lower alkyl of 1 to 6 carbons halogen, $NO_2$, $NH_2$, —NHCO($C_1$-$C_6$) alkyl, or —NHCO($C_1$-$C_6$) alkenyl; A is hydrogen, —COOH or a pharmaceutically acceptable salt thereof, —COOR⁸, —CONR⁹R¹⁰, —CH₂OH, —CH₂OR¹¹, —CH₂OCOR¹¹, —CHO, —CH(OR¹²)₂, —CH(OR¹³O), —COR⁷, —CR⁷(OR¹²)₂, —CR⁷(OR¹³O), or —Si($C_1$-$C_6$)₃, where $R^7$ is an alkyl, cycloalkyl or alkenyl group containing 1 to 5 carbons, $R^8$ is an alkyl group of 1 to 10 carbons or (trimethylsilyl)alkyl where the alkyl group has 1 to 10 carbons, or a cycloalkyl group of 5 to 10 carbons, or $R^8$ is phenyl or lower alkyphenyl, $R^9$ and $R^{10}$ independently are hydrogen, an alkyl group of 1 to 10 carbons, or a cycloalkyl group of 5-10 carbons, or phenyl, hydroxyphenyl or lower alkylphenyl, $R^{11}$ is lower alkyl, phenyl or lower alkylphenyl, $R^{12}$ is lower alkyl, and $R^{13}$ is divalent alkyl radical of 2 to 5 carbons, and $R^{14}$ is H, alkyl of 1 to 10 carbons, fluoro-substituted alkyl of 1 to 10 carbons, alkenyl of 2 to 10 carbons and having 1 to 3 double bonds.

19. The method or use according to any one of embodiments 1-18, wherein the RXR agonist is a compound having the structure of formula XVIII:

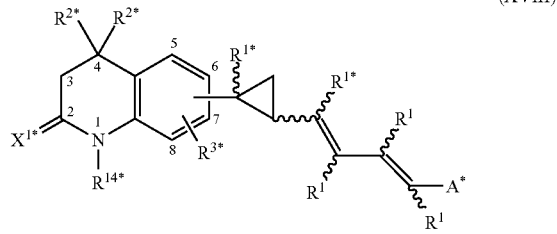

(XVIII)

wherein $R^1$ is independently H, lower alkyl of 1 to 6 carbons, or lower fluoroalkyl of 1 to 6 carbons; $R^{1*}$ is hydrogen or $C_{1-6}$-alkyl; $R^{2*}$ is independently H, lower alkyl of 1 to 6 carbons, or lower fluoroalkyl of 1 to 6 carbons; $R^{3*}$ is hydrogen, lower alkyl of 1 to 6 carbons, fluoro substituted lower alkyl of 1 to 6 carbons or halogen; $X^{1*}$ is an oxo (═O) or a thione (═S) group; A* is hydrogen, —COOH or a pharmaceutically acceptable salt thereof, —COOR⁸, —CONR⁹R¹⁰, where $R^8$ is an alkyl group of 1 to 10 carbons or (trimethylsilyl)alkyl where the alkyl group has 1 to 10 carbons, or a cycloalkyl group of 5 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl, hydroxyphenyl or lower alkylphenyl, and the cyclopropyl group is attached to the 6 or 7 position of the tetrahydroquinoline moiety, and $R^{14*}$ is alkyl of 1 to 10 carbons or fluoro-substituted alkyl of 1 to 10 carbons.

20. The method or use according to any one of embodiments 1-19, wherein the RXR agonist is a compound having the structure of formulae XIX, XX, or XXI:

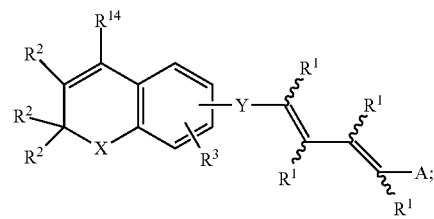

(XIX)

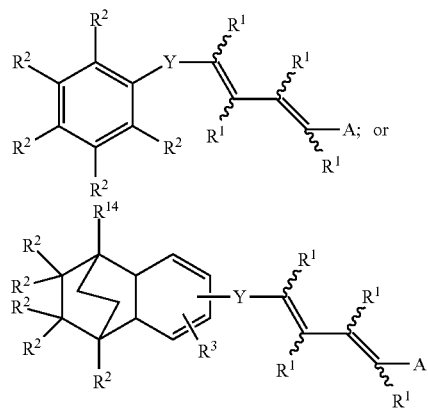

(XX)

where X is O, S, or $(CR^1R^1)_n$ where n is 0, 1 or 2; Y is a bivalent radical having Formulae XXII or XXIII where o is an integer between 1 through 4

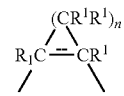

(XXII)

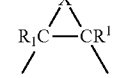

(XXIII)

or Y is a bivalent aryl or 5 or 6 membered heteroaryl radical having 1 to 3 heteroatoms selected from N, S and O, the aryl or heteroaryl groups being unsubstituted, or substituted with 1 to 3 $C_{1-6}$ alkyl or with 1 to 3 $C_{1-6}$ fluoroalkyl groups with the proviso that when the compound is in accordance with Formula II then Y is not a 5 or 6 membered ring; $X^1$ is S or NH; $R^1$ is independently H, lower alkyl of 1 to 6 carbons, or lower fluoroalkyl of 1 to 6 carbons; $R^2$ is independently H, lower alkyl of 1 to 6 carbons, $OR^1$, adamantly, or lower fluoroalkyl of 1 to 6 carbons, or the two $R^2$ groups jointly represent an oxo (═O) group with the proviso that when the compound is in accordance with Formula II then at least one of the $R^2$ substituents is branched-chain alkyl or adamantly; $R^3$ is hydrogen, lower alkyl of 1 to 6 carbons, $OR^1$, fluoro substituted lower alkyl of 1 to 6 carbons or halogen, $NO_2$, $NH_2$, —NHCO($C_1$-$C_6$) alkyl, or —NHCO($C_1$-$C_6$) alkenyl; A is —COOH or a pharmaceutically acceptable salt thereof, COOR⁸, —CONR⁹R¹⁰, —CH₂OH, —CH₂OR¹¹, —CH₂OCOR¹¹, —CHO, —CH(OR¹²)₂, —CH(OR¹³O), —COR⁷, —CR⁷(OR¹²)₂, —CR⁷(OR¹³O), or —Si($C_{1-6}$alkyl)₃, where $R^7$ is an alkyl, cycloalkyl or alkenyl group containing 1 to 5 carbons, $R^8$ is an alkyl group of 1 to 10 carbons or (trimethylsilyl) alkyl where the alkyl group has 1 to 10 carbons, or a cycloalkyl group of 5 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl, hydroxyphenyl or lower alkylphenyl, $R^{12}$ is lower alkyl, and $R^{13}$ is divalent alkyl radical of 2-5 carbons, and $R^{14}$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$-$C_{10}$-alkylphenyl, naphthyl, $C_1$-$C_{10}$-alkylnaphthyl, phenyl-$C_1$-$C_{10}$-alkyl, naphthyl-$C_1$-$C_{10}$ alkyl, $C_1$-$C_{10}$-alkenylphenyl having 1 to 3 double bonds, $C_1$-$C_{10}$-alkynylphenyl having 1 to 3 triple bonds, phenyl-$C_1$-$C_{10}$ alkenyl having 1 to 3 double bonds, phenyl-$C_1$-$C_{10}$ alkenyl having 1 to 3 triple bonds, hydroxyl alkyl of 1 to 10 carbons, hydroxyalkenyl having 2 to 10 carbons and 1 to 3 double bonds, hydroxyalkynyl having 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds where the acyl group is represented by —$COR^8$, or $R^{14}$ is a 5 or 6 membered heteroaryl group having 1 to 3 heteroatoms, the heteroatoms being selected from a group consisting of O, S, and N, the heteroaryl group being unsubstituted or substituted with a $C_1$-$C_{10}$ alkyl group, with a $C_1$-$C_{10}$ fluoroalkyl group, or with halogen, and the dashed line in Formula XXII represents a bond or absence of a bond.

21. The method or use according to any one of embodiments 1-20, wherein the RXR agonist is a compound having the structure of formula XXIV:

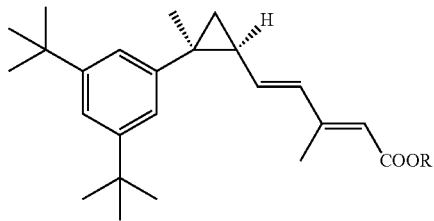

(XXIV)

wherein R is H, lower alkyl of 1 to 6 carbons, or a pharmaceutically acceptable salt of the compound.

22. The method or use according to any one of embodiments 1-21, wherein the RXR agonist is a compound having the structure of formula XXV:

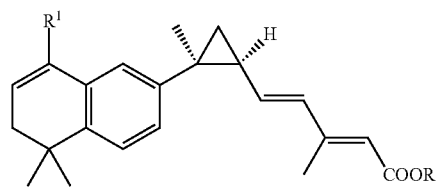

(XXV)

wherein R is H, lower alkyl of 1 to 6 carbons, and $R^1$ is iso-propyl or tertiary-butyl, or a pharmaceutically acceptable salt of the compound.

23. The method or use according to any one of embodiments 1-22, wherein the RXR agonist is a compound having the structure of formula XXVI:

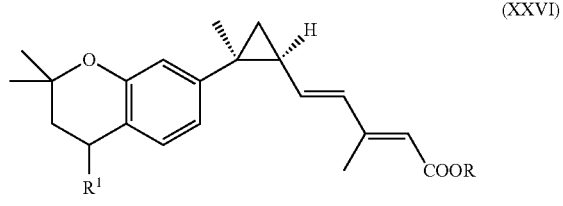

(XXVI)

wherein R is H, lower alkyl of 1 to 6 carbons, and $R^1$ is iso-propyl, n-butyl or tertiary-butyl, or a pharmaceutically acceptable salt of the compound.

24. The method or use according to any one of embodiments 1-23, wherein the RXR agonist is a compound having the structure of formula XXVII:

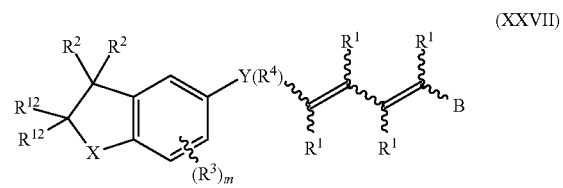

(XXVII)

where X is O or S; Y is a bivalent cycloalkyl or cycloalkenyl radical optionally substituted with one to four $R^4$ groups, the cycloalkenyl radical having 5 to 6 carbons and one double bond, or Y is a bivalent aryl or 5 or 6 membered heteroaryl radical having 1 to 3 heteroatoms selected from N, S and O, the aryl or heteroaryl groups optionally substituted with 1 to 4 $R^4$ groups with the proviso that the cycloalkyl or the cycloalkenyl radical is not substituted on the same carbon with the condensed cyclic moiety and with the diene containing moiety; $R^1$ is independently H, alkyl of 1 to 6 carbons, or fluoroalkyl of 1 to 6 carbons; $R^2$ is independently H, alkyl of 1 to 8 carbons, or fluoroalkyl of 1 to 8 carbons; $R^{12}$ is independently H, alkyl of 1 to 8 carbons, or fluoroalyl of 1 to 8 carbons; $R^3$ is hydrogen, alkyl of 1 to 10 carbons, fluoro substituted alkyl of 1 to 10 carbons, halogen, alkoxy of 1 to 10 carbons, or alkylthio of 1 to 10 carbons; $NO_2$, $NH_2$, —$NHCO(C_1$-$C_6)$ alkyl, —$NHCO(C_1$-$C_6)$ alkenyl, —$NR^1H$ or $N(R^1)_2$, benzyloxy, $C_1$-$C_6$ alkyl-substituted benzyloxy, or $R^3$ is selected from the groups shown below,

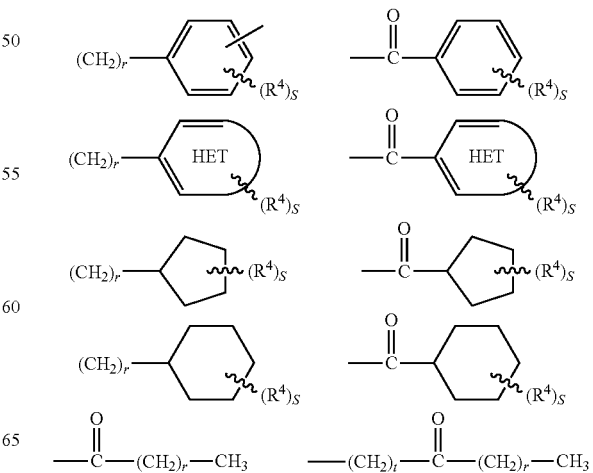

-continued

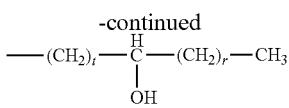

R⁴ is H, halogen, alkyl of 1 to 10 carbons, fluoro substituted alkyl of 1 to 6 carbons, alkoxy of 1 to 10 carbons, or alkylthio of 1 to 10 carbons; m is an integer having the values of 0 to 3; r is an integer having the values of 1 to 10; s is an integer having the values 1 to 4; t is an integer having the values 1 to 5;

represents a 5 or 6 membered heteroaryl ring having 1 to 3 heteroatoms selected from the group consisting of N, S and O; B is hydrogen, COOH or a pharmaceutically acceptable salt thereof, —COOR⁸, —CONR⁹R¹⁰, —CH₂OH, —CH₂OR¹¹, —CH₂OCOR¹¹, —CHO, —CH(OR¹²)₂, —CHOR¹³O, —COR⁷, —CR⁷(OR¹²)₂, —CR⁷OR¹³O, or trilower alkylsilyl, where R⁷ is an alkyl, cycloalkyl or alkenyl group containing 1 to 5 carbons, R⁸ is an alkyl group of 1 to 10 carbons, a cycloalkyl group of 5 to 10 carbons or trimethylsilylalkyl where the alkyl group has 1 to 10 carbons, or R⁸ is phenyl or lower alkylphenyl, R⁹ and R¹⁰ independently are hydrogen, an alkyl group of 1 to 10 carbons, or a cycloalkyl group of 5-10 carbons, or phenyl or lower alkylphenyl, R¹¹ is lower alkyl, phenyl or lower alkylphenyl, R¹² is lower alkyl, and R¹³ is divalent alkyl radical of 2 to 5 carbons.

25. The method or use according to any one of embodiments 1-24, wherein the RXR agonist is a compound having the structure of formula XXVIII:

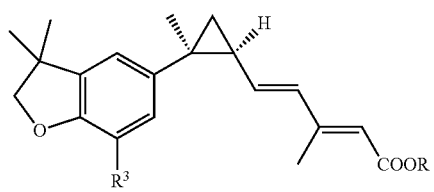

(XXVIII)

wherein R¹ is H or methyl; R⁸ is H, alkyl of 1 to 6 carbons, or a pharmaceutically acceptable cation, and R³ is hydrogen, alkyl of 1 to 10 carbons, halogen, alkoxy of 1 to 10 carbons, or R³ is selected from the groups shown below

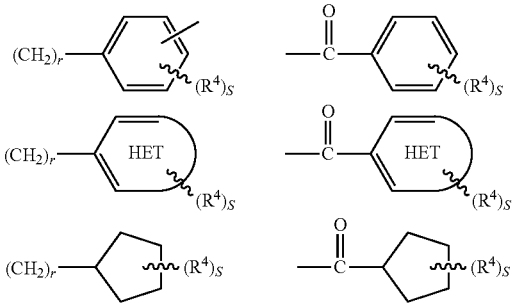

-continued

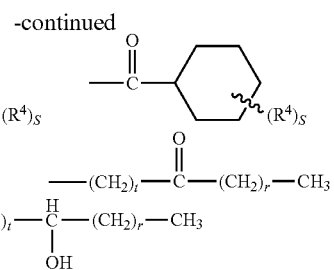

where R⁴ is H, halogen, alkyl of 1 to 10 carbons, carbons, alkoxy of 1 to 10; r is an integer having the values of 1 to 10; s is an integer having the values 1 to 4;

represents a 5 or 6 membered heteroaryl ring having 1 to 3 heteroatoms selected from the group consisting of N, S and O, and t is an integer having the values 1 to 5.

26. The method or use according to any one of embodiments 1-25, wherein the RXR agonist is 3,7-dimethyl-6(S),7(S)-methano,7-[1,1,4,4-tetramethyl-1,2,3,4-tetrahydronaphth-7-yl]2(E),4(E) heptadienoic acid, and has the structure of formula XXIX:

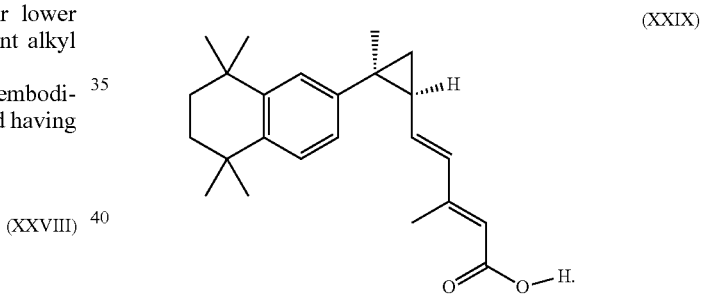

(XXIX)

27. The method or use according to any one of embodiments 1, 2, or 4-26, wherein the autoimmune disorder is systemic autoimmune disorder or organ-specific autoimmune disorder.

28. The method or use according to any one of embodiments 1, 2, or 4-27, wherein the autoimmune disorder is an acute disseminated encephalomyelitis (ADEM), an Addison's disease, an allergy, allergic rhinitis, an Alzheimer's disease, an anti-phospholipid antibody syndrome (APS), an arthritis, an asthma, an autoimmune deficiency syndrome (AIDS), an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an endometriosis, a gastrointestinal disorder, a Goodpasture's syndrome, a Graves' disease, a Guillain-Barré syndrome (GBS), a Hashimoto's thyroiditis, a hidradenitis suppurativa, an idiopathic thrombocytopenic purpura, an interstitial cystitis, a lupus, a morphea, a multiple sclerosis (MS), a myasthenia gravis, a myopathy such as, e.g., a dermatomyositis, an inclusion body myositis, or a polymyositis, a myositis, a narcolepsy, a neuromyotonia, a Parkinson's disease, a pemphigus vulgaris, a pernicious anaemia, a primary biliary cirrhosis, a psoriasis, a recurrent disseminated encephalomyelitis, a rheumatic fever, a schizophrenia, a scleroderma, a Sjögren's syndrome, a skin disorder, a tenosynovitis, a uveitis, a vasculitis, or a vitiligo.

29. The method or use according to embodiment 28, wherein the skin disorder is a dermatitis, an eczema, a statis dermatitis, a hidradenitis suppurativa, a psoriasis, a rosacea or a scleroderma.

30. The method or use according to embodiment 29, wherein the eczema is an atopic eczema, a contact eczema, a xerotic eczema, a seborrhoeic dermatitis, a dyshidrosis, a discoid eczema, a venous eczema, a dermatitis herpetiformis, a neurodermatitis, or an autoeczematization.

31. The method or use according to embodiment 29, wherein the psoriasis is a plaqure psoriasis, a nail psoriasis, a guttate psoriasis, a scalp psoriasis, an inverse psoriasis, a pustular psoriasis, or an erythrodermis psoriasis.

32. The method or use according to embodiment 28, wherein the arthritis is a monoarthritis, an oligoarthritis, or a polyarthritis.

33. The method or use according to embodiment 28, wherein the arthritis is an auto-immune disease or a non-autoimmune disease.

34. The method or use according to embodiment 28, wherein the arthritis is an osteoarthritis, a rheumatoid arthritis, a juvenile idiopathic arthritis, a septic arthritis, a spondyloarthropathy, a gout, a pseudogout, or Still's disease 35. The method or use according to embodiment 34, wherein the spondyloarthropathy is an ankylosing spondylitis, a reactive arthritis (Reiter's syndrome), a psoriatic arthritis, an enteropathic arthritis associated with inflammatory bowel disease, a Whipple disease or a Behcet disease.

36. The method or use according to embodiment 28, wherein the gastrointestinal disorder is an irritable bowel disease or an inflammatory bowel.

37. The method or use according to embodiment 36, wherein the inflammatory bowel is a Crohn's disease or an ulcerative colitis.

38. The method or use according to embodiment 28, wherein the lupus is a discoid lupus erythematosus, a drug-induced lupus erythematosus, a lupus nephritis, a neonatal lupus, a subacute cutaneous lupus erythematosus, or a systemic lupus erythematosus.

39. The method or use according to embodiment 28, wherein the vasculitis is a Buerger's disease, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a microscopic polyarteritis/polyangiitis, a polyarteritis nodosa, a polymyalgia rheumatica (PMR), a rheumatoid vasculitis, a Takayasu arteritis, or a Wegener's granulomatosis.

40. The method or use according to any one of embodiments 3-26, wherein the transplant rejection is a hyperacute rejection, an acute rejection, or a chronic rejection.

41. The method or use according to any one of embodiments 3-27, wherein the transplant rejection is a graft-versus-host-disease.

42. The method or use according to any one of embodiments 1-41, wherein the therapeutically effective amount is about 0.01 mg/kg/day to about 100 mg/kg/day.

43. The method or use according to embodiment 42, wherein the therapeutically effective amount is about 0.1 mg/kg/day to about 10 mg/kg/day.

44. The method or use according to any one of embodiments 1-41, wherein the therapeutically effective amount is about 0.1 mg/m2/day to about 100 mg/m2/day.

45. The method or use according to embodiment 44, wherein the therapeutically effective amount is about 15 mg/m2/day to about 60 mg/m2/day.

46. The method or use according to any one of embodiment 1 or 3-45, wherein the symptom reduced is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disorder or a transplant rejection, an increase in the size of an organ or tissue, or the destruction of an organ or tissue.

47. The method or use according to embodiment 2 or 46, wherein the inflammation symptom reduced is edema, hyperemia, erythema, bruising, tenderness, stiffness, swollenness, fever, a chill, congestion of the respiratory tract including nose and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

48. The method or use according to any one of embodiments 1-47, wherein the RXR agonist is a pure RXR agonist.

49. The method or use according to embodiment 48, wherein the RXR agonist is a pure RXR agonist that activates a permissive heterodimer by 1% or less, 2% or less, 3% or less, 4% or less, 5% or less, 6% or less, 7% or less, 8% or less, 9% or less, or 10% or less relative to the ability of a non-pure RXR agonist to activate the same permissive heterodimer.

50. The method or use according to any one of embodiments 1-49, wherein the RXR agonist has activity that promotes Treg cell differentiation.

51. The method or use according to embodiment 1-50, wherein the RXR agonist promotes Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%.

52. The method or use according to any one of embodiments 1-51, wherein the RXR agonist increases Foxp3 and/or α4β7 expression in cells exposed to the RXR agonist.

53. The method or use according to embodiment 52, wherein the RXR agonist increases Foxp3 and/or α4β7 expression by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same RXR agonist.

54. The method or use according to any one of embodiments 1-51, wherein the RXR agonist increases Foxp3 and/or α4β7 expression in naive $CD4^+$ $CD25^-$ $FoxP3^-$ cells cultured under Treg cell differentiation conditions.

55. The method or use according to embodiment 54, wherein the RXR agonist increases Foxp3 and/or α4β7 expression in naive $CD4^+$ $CD25^-$ $FoxP3^-$ cells cultured under Treg cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive $CD4^+$ $CD25^-$ $FoxP3^-$ cells cultured under Treg cell differentiation not exposed to the same RXR agonist.

56. The method or use according to any one of embodiments 1-55, wherein the RXR agonist has activity that inhibits Th17 cell differentiation.

57. The method or use according to embodiment 1-56, wherein the RXR agonist inhibits Th17 cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%.

58. The method or use according to any one of embodiments 1-57, wherein the RXR agonist decreases IL-17A expression in cells exposed to the RXR agonist.

59. The method or use according to embodiment 58, wherein the RXR agonist decreases IL-17A expression by at least 10%, at least 20%, at least 30%, at least 40%, at least 50%, at least 60%, at least 70%, at least 80%, at least 90%, at least 100%, at least 200%, at least 300%, at least 400%, or at least 500%, relative to cells not exposed to the same RXR agonist.

60. The method or use according to any one of embodiments 1-59, wherein the RXR agonist decreases IL-17A expression in naive $CD4^+$ $CD25^-$ $FoxP3^-$ cells cultured under Th17 cell differentiation conditions.

61. The method or use according to embodiment 60, wherein the RXR agonist decreases IL-17A expression in naive $CD4^+$ $CD25^-$ $FoxP3^-$ cells cultured under Th17 cell differentiation by at least 10%, at least 20%, at least 30%, at least 40%, at least 50%, at least 60%, at least 70%, at least 80%, at least 90%, at least 100%, at least 200%, at least 300%, at least 400%, or at least 500%, relative to naive $CD4^+$ $CD25^-$ $FoxP3^-$ cells cultured under Treg cell differentiation not exposed to the same RXR agonist.

62. A method of promoting Treg cell differentiation in an individual, the method comprising the step of administering to the individual in need thereof a therapeutically effective amount of a RXR agonist, wherein administration of the RXR agonist promotes Treg cell differentiation.

63. Use of a RXR agonist to promote Treg cell differentiation in an individual, wherein administration of the RXR agonist to the individual promotes Treg cell differentiation.

64. The method according to embodiment 62 or use according to embodiment 63, wherein administration of the RXR agonist to the individual also inhibits Th17 cell differentiation.

65. The method or use according to any one of embodiments 62-64, wherein the RXR agonist is according to any one of embodiments 6-26 or 48-61.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating an autoimmune disorder, inflammation associated with an autoimmune disorder, or a transplant rejection using the RXR agonists disclosed herein, uses of a RXR agonists disclosed herein to manufacture a medicament and/or treat an autoimmune disorder, inflammation associated with an autoimmune disorder, or a transplant rejection, methods of promoting Treg cell differentiation in an individual, inhibiting Th17 cell differentiation, or both, as well as uses of a RXR agonists disclosed herein to promote Treg cell differentiation in an individual, inhibit Th17 cell differentiation, or both.

Example 1

RXR Agonists Induce Treg Cell Differentiation

Figure 1B:
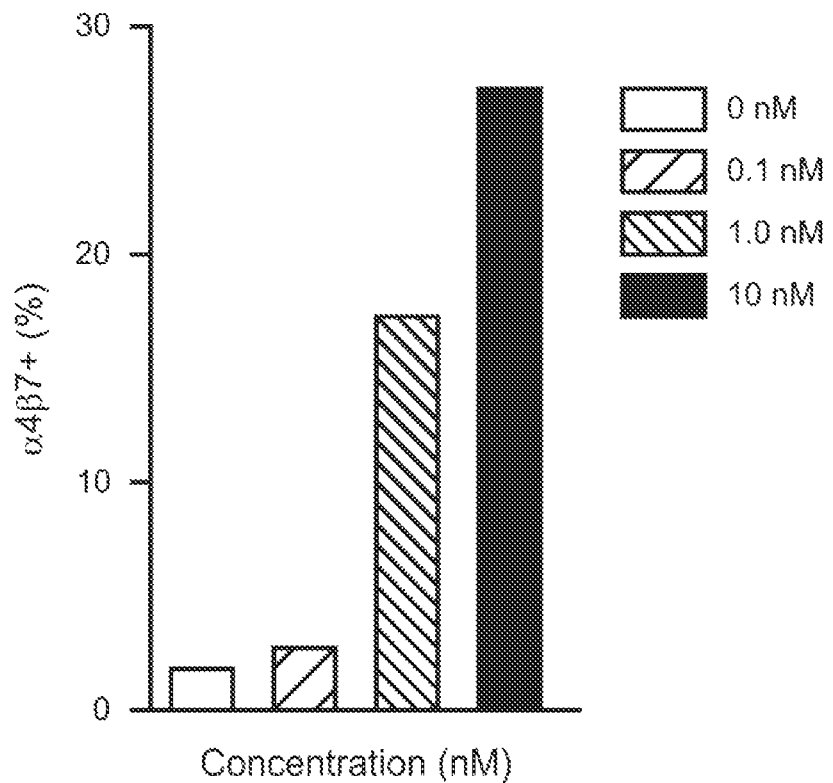

To determine whether a RXR agonist can induce Treg cell differentiation, the ability of an RXR agonist to promote Treg cell differentiation under Treg cell differentiation conditions was assessed by monitoring Foxp3 and $\alpha 4\beta 7$ expression. Naive $CD4^+$ $CD25^-$ $FoxP3^-$ cells were purified from a Foxp3-GFP mouse using flow cytometry by sorting and isolating based upon a $GFP^-$ phenotype. These cells were then cultured under Treg cell differentiation conditions by treating the cells with $\alpha CD3$ and $\alpha CD28$ polyclonal antibodies in the presence of IL-2 and TGF-$\beta$. The cultured cells were incubated with RXR agonist 194204 (Formula XXIX) at 0.1 nM, 1.0 nM and 10 nM and the expression of Foxp3 and $\alpha 4\beta 7$ was analyzed. The results indicate that RXR agonist exerted significant impact on the expression of Foxp3, inducing nearly 100% $Foxp3^+$ T cells at concentrations of 1 nM or higher. FIG. 1A. These results also indicate that RXR agonist 194204 also induced expression of $\alpha 4\beta 7$ (a gut homing receptor). FIG. 1B. These results indicate that RXR agonists could be useful in reducing a symptom of an autoimmune disorder or a transplant rejection.

Example 2

RXR Agonists Regulate T Cell Differentiation

Figure 2A:
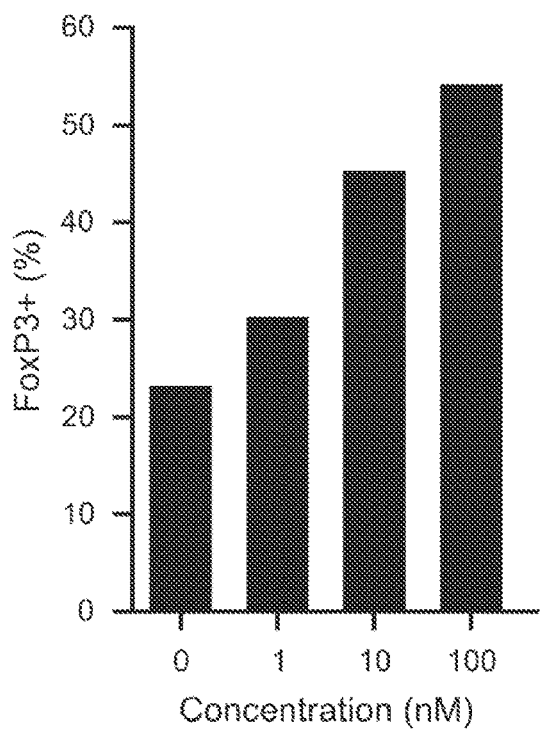
FIG. 2A-B shows RXR agonist effects on differentiation.
Figure 2B:
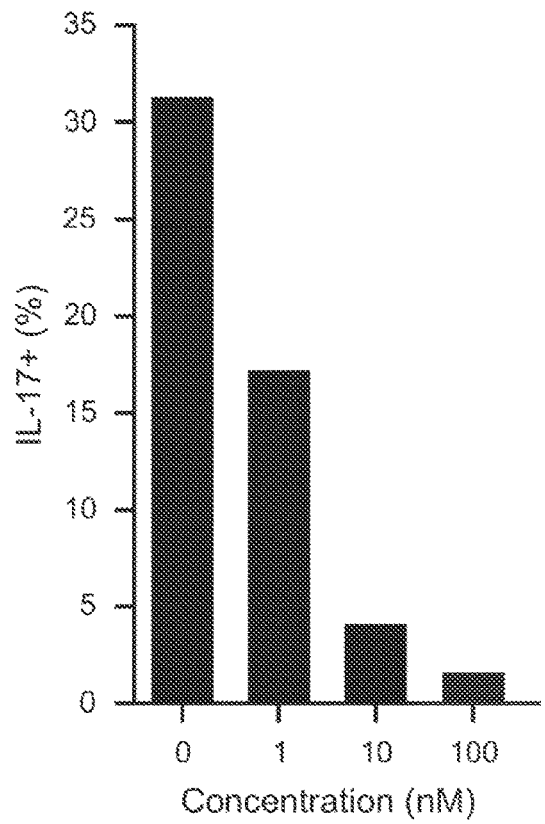

To determine whether a RXR agonist can regulate T cell differentiation, the ability of an RXR agonist to promote Treg cell differentiation and inhibit Th17 cell differentiation under Th17 cell differentiation conditions was assessed by monitoring Foxp3 and IL-17A expression. Naive $CD4^+$ $CD25^-$ $FoxP3^-$ cells were purified from a Foxp3-GFP mouse using flow cytometry by sorting and isolating based upon a $GFP^-$ phenotype. These cells were then cultured under Th17 cell differentiation conditions in media with 0 nM, 1 nM, 10 nM, and 100 nM of RXR agonist 194204 (Formula XXIX) and the expression of Foxp3 and IL-17A was analyzed. See, e.g., Elias, et al., Retinoic Acid Inhibits Th17 Polarization and Enhances FoxP3 Expression through a Stat-3/Stat-5 Independent Pathway, Blood 111(3): 1-13-1020 (2008). The results indicated that as the concentration of the RXR agonist increased, Foxp3 expression increased, indicating an increased presence of Treg cells. FIG. 2A. Additionally, the data demonstrate that as the concentration of the RXR agonist increased, IL-17A expression decreased, indicating a decreased presence of Th17 cells. FIG. 2B. These results indicate that RXR agonists regulate T cell differentiation by promoting differentiation of immunosuppressive Treg cells and concurrently inhibiting differentiation of inflammatory Th17 cells from naïve T cells in vitro.

Example 3

RXR Agonists Regulate T Cell Differentiation Independent of RAR Signaling

Figure 3:
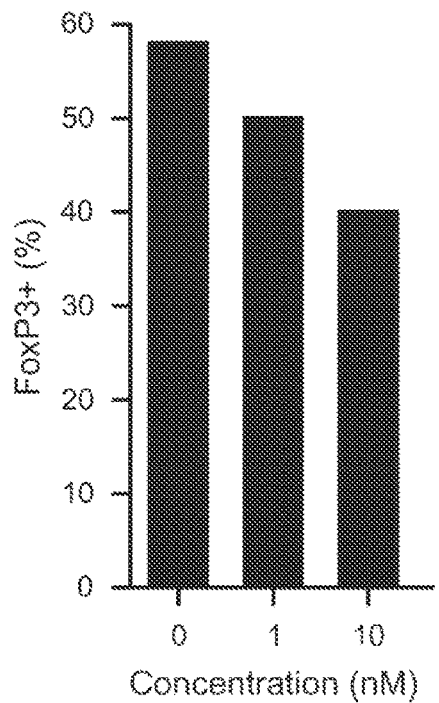
FIG. 3 shows the effects of RAR signaling inhibition on RXR agonist inducement of Treg differentiation.

To determine whether a RXR agonist can mediate its effects via RAR/RXR receptor heterodimers, via RXR receptor homodimers, or via some other RXR containing complex, T cells were incubated with a RXR agonist in the presence of a pan-RAR antagonist and the expression of Foxp3 was assessed. Naive CD4+ CD25− FoxP3− cells were purified from a Foxp3-GFP mouse using flow cytometry by sorting and isolating based upon a GFP− phenotype. These cells were then cultured under Treg cell differentiation conditions by treating the cells with αCD3 and αCD28 polyclonal antibodies in the presence of IL-2 and TGF-β. The cultured cells were incubated with RXR agonist 194204 (Formula XXIX) at 1.0 nM together with 0 nM, 1 nM, or 10 nM of a pan-RAR antagonist 194310. The cultured cells were then assayed for the expression of Foxp3. The results indicate that the inclusion of a pan-RAR antagonist only partially blocked the induction of Foxp3 expression observed with an RXR agonist alone. FIG. 3. However, this partial inhibition of Fox3p expression may actually be due to the blocking of the effects of endogenous RA in the culture medium. As such, these results indicate that the observed conversion of T cells into Treg cells appears to occur through the use of RXR receptor homodimers and/or some other RXR containing complex, and not through a RAR-mediated mechanism.

Example 4

T Cell Differentiation is Mediated Through RXR Signaling by RXR Agonists

To determine whether a RXR agonist can mediate its effects via an RXRα receptor homodimers, RXRβ receptor homodimers, RXRγ receptor homodimers, or any combination thereof, or the corresponding RAR/RXR heterodimers, receptor-mediated transactivation assays were performed. For transactivation assays assessing RXR homodimer signaling, CV-1 cells were transfected with 1) an expression construct including a full length RXRα, RXRβ, or RXRγ; and 2) a rCRBPII/RXRE-tk-Luc reporter construct that included RXR homodimer-specific RXRE/DR1 responsive element linked to a luciferase gene. For transactivation assays assessing RAR/RXR heterodimer signaling, CV-1 cells were transfected with 1) an expression construct comprising a fusion protein including an estrogen receptor (ER) DNA binding domain linked to the ligand binding domain of RARα, RARβ, or RARγ and 2) a ERE-tk-Luc reporter construct that included an estrogen receptor responsive element linked to a luciferase gene. The ER-RAR fusion proteins provided an accurate readout of only the transfected ER-RAR. After transfection, CV-1 cells were treated with RXR agonist 194204 (Formula XXIX) at increasing concentrations for 20 hours before measuring luciferase activity. Luciferase activity is expressed as percent of maximal activity obtained using 1 µM RXR agonist 194204 for RXRs and 1 µM all-trans-retinoic acid (ATRA) for RARs (Table 1). Data are mean values±SE from five independent experiments.

TABLE 1

RXR Agonist Potencies in Activating RXRs and RARs

| Compound | Structure | EC$_{50}$ (nM) Efficacy (% of 1 µM 194204) | | | EC$_{50}$ (nM) Efficacy (% of 1 µM ATRA) | | |
|---|---|---|---|---|---|---|---|
| | | RXRα | RXRβ | RXRγ | RARα | RARβ | RARγ |
| 194204 | | 0.08 ± 0.01 100 | 0.47 ± 0.05 100 | 0.09 ± 0.01 100 | >1,000 | >1,000 | >1,000 |

Figure 4:
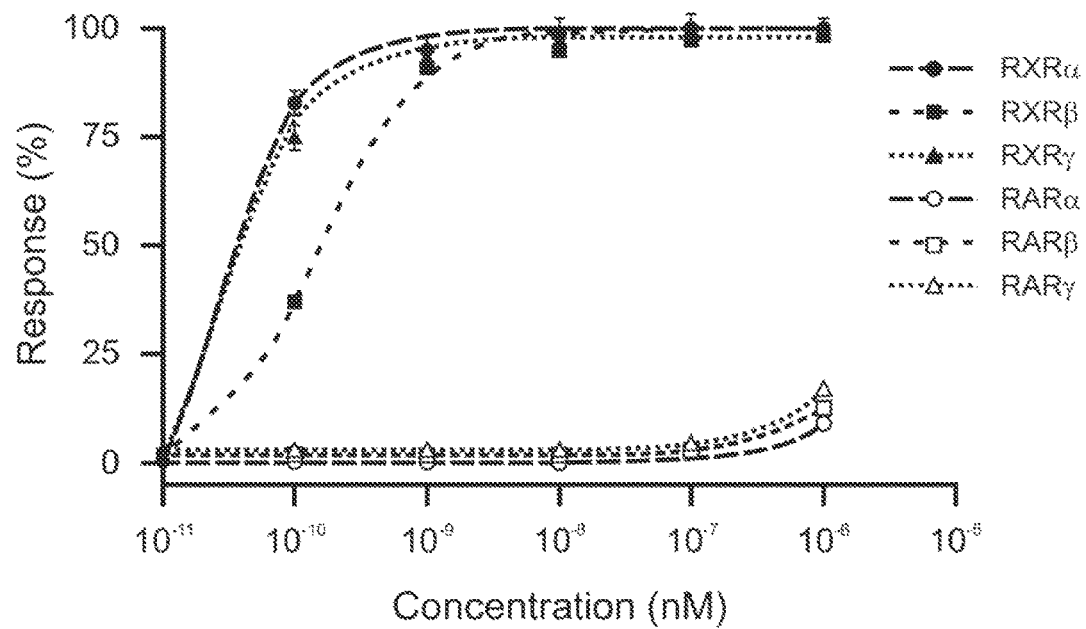
FIG. 4 shows RXR agonist activation of transcription from $RXR\alpha$, $RXR\beta$, $RXR\gamma$, $RAR\alpha$, $RAR\beta$, and $RAR\gamma$ using transactivation assays.

These results indicate that RXR agonist 194204 activated RXR receptors with very high potency (EC$_{50}$<0.5 nM) for all three RXR subtypes (Table 1). In contrast, EC$_{50}$ of the RXR agonist for RARs was >1,000 nM with minimal activity detected at ≥1 µM. This difference represents >2,000-fold selectivity for RXRs over RARs in functional transactivation assays. Additionally, these data demonstrate that RXR agonist 194204 was more than 1,000-fold more potent in activating RXR receptors rather than RAR receptors. FIG. 4. These results indicate that Treg differentiation was mediated through a RXR signaling pathway and not via a RAR signaling pathway. Also, using appropriate receptor and reporter constructs, RXR agonist 194204 was shown not to transactivate so called "permissive RXR heterodimers", such as, e.g., PPAR/RXR, FXR/RXR and LXR/RXR. In this regard, RXR agonist 194204 is distinct from other RXR agonists.

Example 5

Binding Affinity of RXR Agonists

To determine the binding affinity for a RXR agonist, competitive displacement assays were performed. RXRα, RXRβ, RXRγ, RARα, RARβ, or RARγ were expressed in SF21 cells using a baclovirus expression system and the resulting proteins were purified. To determine the binding affinity for a RXR agonist for an RXR, purified RXRα, RXRβ, and RXRγ were separately incubated with 10 nM [$^3$H]-9CRA, and the binding affinity of the RXR agonist 194204 (Formula XXIX) was determined by competitive displacement of [$^3$H]-9CRA from the receptor. To determine the binding affinity for a RXR agonist for an RAR, purified RARα, RARβ, and RARγ were incubated with 5 nM [$^3$H]-ATRA, and the binding affinity of the RXR agonist 194204 (XXIX) was determined by competitive displacement of

[³H]-ATRA from the receptor. Ki values are mean values of at least two independent experiments (Table 2). Standard errors (±) among independent experiments are indicated.

As shown in Table 2, RXR agonist 194204 displayed high affinity for RXRα, RXRβ, and RXRγ with Ki values being 1.7, 16, and 43 nM, respectively. In contrast, the RXR agonist 194204 bound with very low affinity to each of the RARs (Ki values being >1,000 nM). These data indicate that 194204 is highly selective for the RXRs relative to the RARs.

TABLE 2

RXR Agonist Binding Affinities

| Compound | Structure | RXR Binding Affinity Ki (nM) | | | RAR Binding Affinity Ki (nM) | | |
|---|---|---|---|---|---|---|---|
| | | RXRα | RXRβ | RXRγ | RARα | RARβ | RARγ |
| 194204 | [structure] | 1.7 ± 0.1 | 16 ± 1.0 | 43 ± 3.0 | 6344 ± 674 | 7552 ± 638 | 4742 ± 405 |

Example 6

RXR Agonists Attenuate EAE in B6 Mice

To determine whether a RXR agonist can attenuate multiple sclerosis, C57BL/6 (B6) mice were immunized (day 0) to induce EAE by subcutaneous (s.c.) injection at the base of their spine with 200 uL of adjuvant containing 125 ug myelin oligodendrocyte glycoprotein peptide (35-55) (MOG peptide; Peptides International, Louisville, Ky.) and 400 ug non-viable *M. tuberculosis* H37 desiccate emulsified in a mixture of incomplete Freund's adjuvant and phosphate buffered saline (PBS). Mice were also given 200 ng of pertussis toxin in PBS administered by inter-peritoneal (i.p.) injection on the same day as MOG emulsion injection (day 0) and 2 days later (day 2). Starting on day 7 after immunization, mice were given the RXR agonist 194204 (50 ug) or vehicle control i.p. every other day for the duration of the experiment (n=6-7 mice/group). Statistics show the results of a Mann Whitney test (analyzed from start of treatment to the end of the experiment). Mice were scored using the following scale: 0—Mice have no disease, 1—Mice have distal limp tail or rear leg weakness (paresis), 1.5—Mice have distal limp tail and rear leg weakness, 2—Mice have complete limp tail and rear leg weakness, 2.5—Mice have complete limp tail and weakness in both rear legs, 3—Mice have complete limp tail and paralysis in both rear legs, 3.5—Mice have complete limp tail, paralysis in both rear legs, and forelimb weakness. Mice receiving a score of 3.5 were immediately euthanized.

Figure 5:
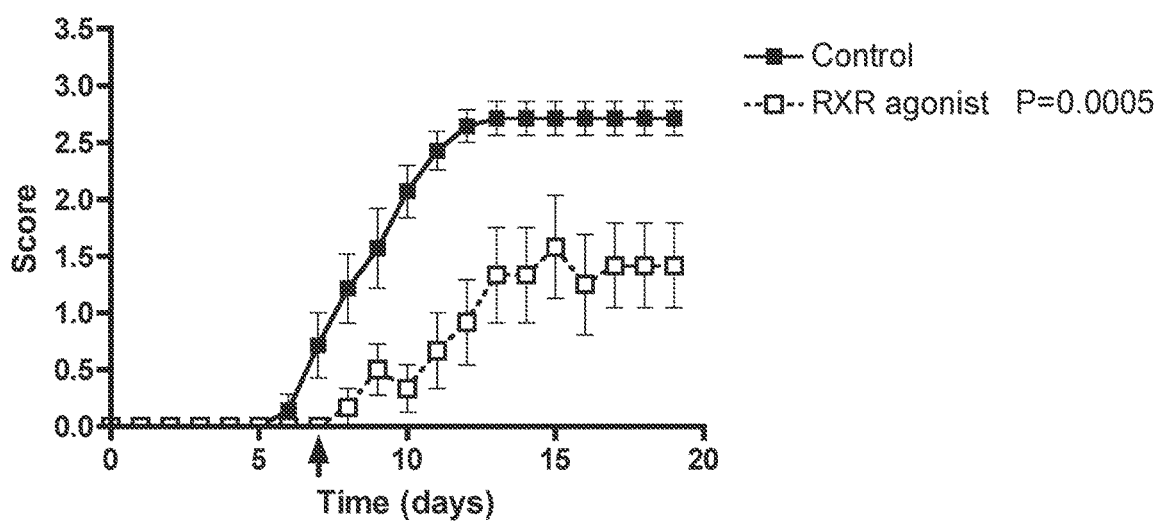
FIG. 5 shows that RXR agonists attenuate experimental autoimmune encephalomyelitis (EAE) in C57BL/6 mice.

FIG. 5 depicts scores of disease severity over time. The results indicate that administration of a RXR agonist significantly reduces the symptoms of EAE in mice. Efficacy of the RXR agonist was observed after the first administration (day 7) and maintained throughout the course of the study (day 20).

Example 7

RXR Agonist-Treated Mice have Reduced Central Nervous System Infiltrating Cells

To determine whether a RXR agonist can reduce central nervous system (CNS) infiltrating cells, C57BL/6 (B6) mice were treated as described in Example 6. On day 20 after immunization, mice were sacrificed and perfused with phosphate buffered saline (PBS). Brain and spinal cord tissue was isolated, digested with DNase and Liberase DL (Roche Diagnostics, Indianapolis, Ind.) for 30 minutes, and homogenized through 70 micron nylon mesh filters. Resulting cells were placed over a Percoll gradient to remove myelin. The remaining cells (microglia and CNS infiltrating cells) were counted, stained for molecules of interest, and run on a flow cytometer. Based on the frequencies obtained by FACS of these cell populations, total cell numbers of CNS infiltrating leukocytes expressing CD45, including $CD4^+$ T cells and $CD11c^+$ $CD11b^+$ myeloid dendritic cells (DC), were calculated.

Figure 6A:
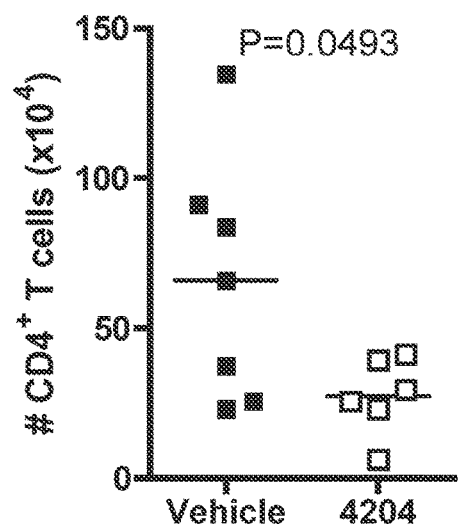
FIG. 6A-B shows that RXR agonists reduce leukocyte infiltration into the central nervous system.
Figure 6B:
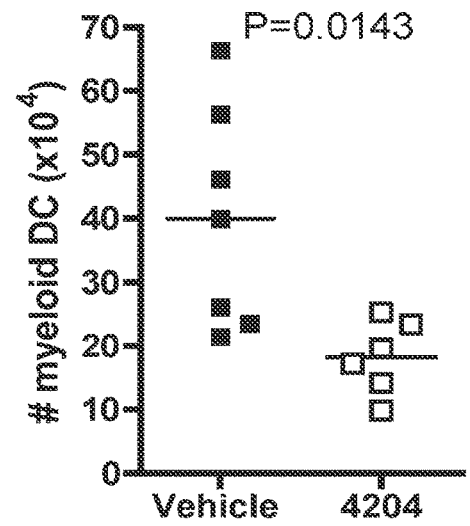

FIG. 6 compares the number of $CD4^+$ cells or $CD11c^+$ $CD11b^+$ cells (myeloid DC) in mice treated with the RXR agonist 194204 verses the vehicle control. There was a significant reduction in the infiltration of both $CD4^+$ cells and $CD11c^+$ $CD11b^+$ cells in animals treated with a RXR agonist as compared to the control. As disease is propagated in the CNS through the $CD4^+$ cells infiltrating the CNS and becoming re-activated by $CD11c^+$ $CD11b^+$ cells, this suggests that part of the mechanism of action in this model is to limit the presence of the cells in the CNS.

Example 8

RXR Agonists Attenuate EAE in SJL Mice

To determine whether a RXR agonist can attenuate multiple sclerosis, SJL mice were immunized to induce EAE by s.c. injection at the base of their spine with 200 uL of adjuvant containing 200 ug proteolipid proteins (139-151) (PLP peptide; Peptides International, Louisville, Ky.) and 400 ug of non-viable *M. tuberculosis* H37 desiccate emulsified in a mixture of incomplete Freund's adjuvant and PBS. Mice were also given 150 ng of pertussis toxin in PBS i.p. on the same day as PLP emulsion injection and 2 days later. Starting day 7 after immunization, mice were given the RXR agonist 194204 (50 ug) or vehicle control i.p. every other day for the duration of the experiment (n=6 mice/group). Mice were scored using the scale described in Example 6.

Figure 7:
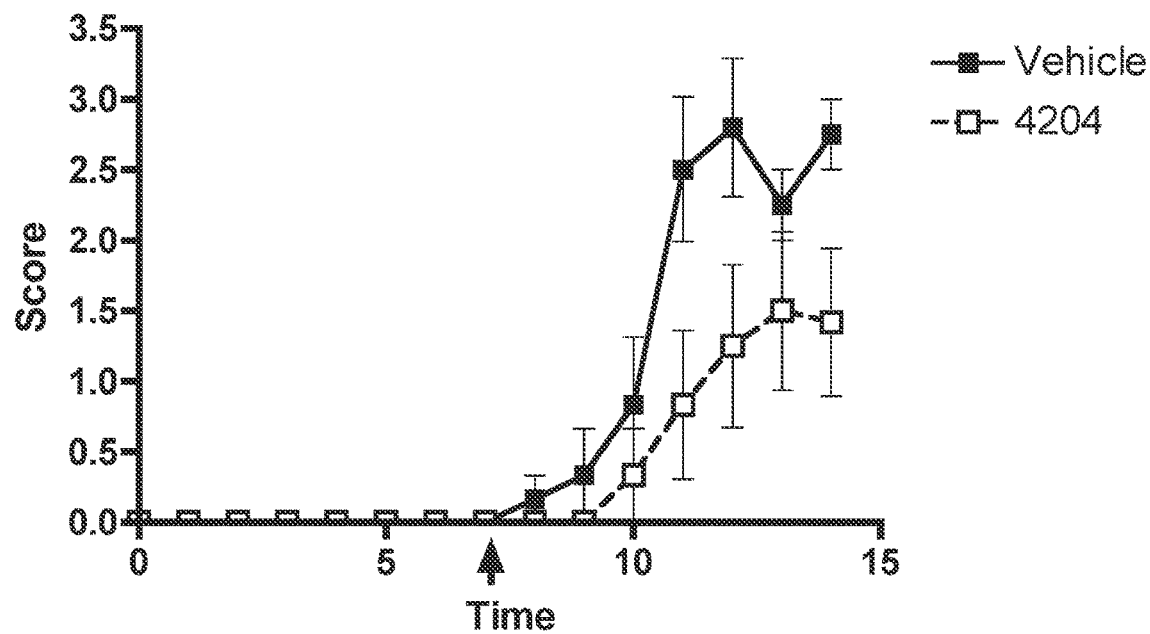
FIG. 7 shows RXR agonists attenuate EAE in SJL mice.

The results indicate that administration of a RXR agonist significantly reduces the symptoms of EAE in mice. Table 3 shows the features of a RXR agonist 194204 treatment in SLJ mice. FIG. 7 depicts scores of disease severity over time. Efficacy of the RXR agonist was observed after the second administration (day 8) and maintained throughout the course of the study (day 14).

TABLE 3

RXR agonist Treatment in SJL Mice

| Clinical Features | Vehicle | 4204 |
|---|---|---|
| Mean Maximum Score | 3.2 ± 0.6 | 1.5 ± 1.4 |
| Disease Incidence | 6/6 | 4/6 |
| Death from Disease | 4/6 | 0/6 |

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of treating an autoimmune gastrointestinal disorder, wherein the autoimmune gastrointestinal disorder is an inflammatory bowel disease or celiac disease, the method comprising elevating Treg cell numbers and suppressing Th17 cell numbers in an individual having the autoimmune gastrointestinal disorder by administering a therapeutically effective amount of a retinoid X receptor (RXR) agonist having the structure of formula XII:

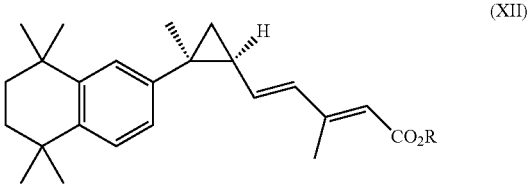
(XII)

or a pharmaceutically acceptable salt thereof;
wherein R is H or lower alkyl of 1 to 6 carbons;
wherein the therapeutically effective amount is about 0.001 mg/kg/day to about 100 mg/kg/day;
wherein the inflammatory bowel disease is ulcerative colitis or Crohn's disease; and
whereby the balance between Treg and Th17 cell development is modulated to restrain autoimmunity.

2. The method according to claim 1, wherein the RXR agonist is 3,7-dimethyl-6(S),7(S)-methano,7-[1,1,4,4-tetramethyl-1,2,3,4-tetrahydronaphth-7-yl]2(E),4(E) heptadienoic acid, and has the structure of formula XXIX:

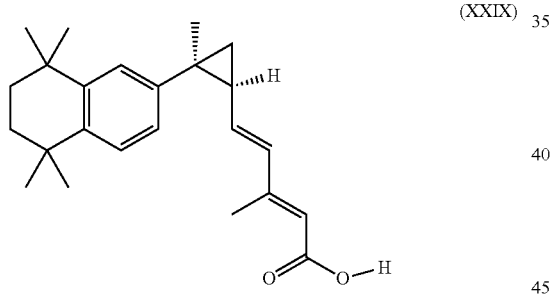
(XXIX)

or a pharmaceutically acceptable salt thereof.

3. The method according to claim 1, wherein the therapeutically effective amount is about 0.001 mg/kg/day to about 0.2 mg/kg/day.

4. The method according to claim 1, wherein the therapeutically effective amount is about 0.1 mg/kg/day to about 3.0 mg/kg/day.

5. The method according to claim 1, wherein R is H.

6. The method according to claim 2, wherein the RXR agonist is a salt of the compound of formula XXIX.

7. The method of claim 1, wherein the inflammatory bowel disease is an ulcerative colitis.

8. The method of claim 1, wherein the inflammatory bowel disease is Crohn's disease.

9. A method of treating an autoimmune aspect of an autoimmune gastrointestinal disorder, wherein the autoimmune gastrointestinal disorder is an inflammatory bowel disease or celiac disease, the method comprising concurrently promoting differentiation of Treg cells and inhibiting differentiation of Th17 cells using a single agent by administering to an individual having the autoimmune gastrointestinal disorder a therapeutically effective amount of a retinoid X receptor (RXR) agonist having the structure of formula XII:

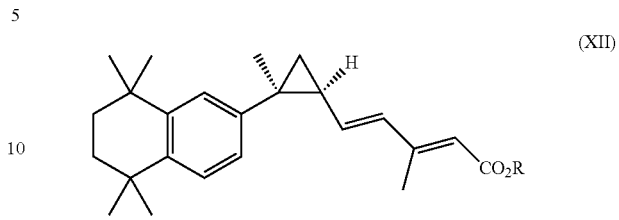
(XII)

or a pharmaceutically acceptable salt thereof;
wherein R is H or lower alkyl of 1 to 6 carbons;
wherein the therapeutically effective amount is about 0.001 mg/kg/day to about 100 mg/kg/day;
wherein the inflammatory bowel disease is ulcerative colitis or Crohn's disease; and
wherein the autoimmune aspect comprises inflammation, an elevated Th17 to Treg cell ratio, or tissue destruction;
whereby the autoimmune aspect of the autoimmune gastrointestinal disorder is reduced.

10. The method of claim 9, wherein the inflammatory bowel disease is an ulcerative colitis.

11. The method of claim 9, wherein the inflammatory bowel disease is Crohn's disease.

12. The method according to claim 9, wherein the RXR agonist is 3,7-dimethyl-6(S),7(S)-methano,7-[1,1,4,4-tetramethyl-1,2,3,4-tetrahydronaphth-7-yl]2(E),4(E) heptadienoic acid, and has the structure of formula XXIX:

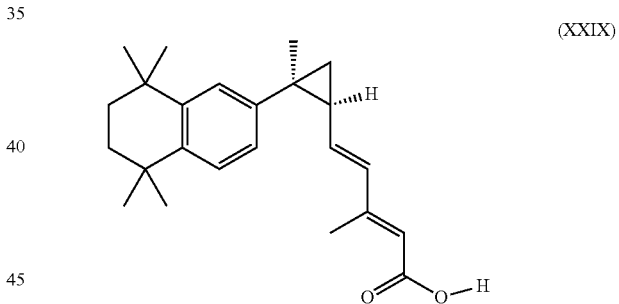
(XXIX)

or a pharmaceutically acceptable salt thereof.

13. The method according to claim 9, wherein the therapeutically effective amount is about 0.001 mg/kg/day to about 0.2 mg/kg/day.

14. The method according to claim 9, wherein the therapeutically effective amount is about 0.1 mg/kg/day to about 3.0 mg/kg/day.

15. The method according to claim 9, wherein R is H.

16. The method according to claim 12, wherein the RXR agonist is a salt of the compound of formula XXIX.

17. The method according to claim 1, wherein the RXR agonist is administered topically.

18. The method according to claim 9, wherein the RXR agonist is administered topically.

19. The method of claim according to claim 1, wherein the therapeutically effective amount is about 0.01 mg/kg/day to about 0.1 mg/kg/day.

20. The method of claim according to claim 9, wherein the therapeutically effective amount is about 0.01 mg/kg/day to about 0.1 mg/kg/day.

21. The method according to claim 1, wherein elevating Treg cell numbers comprises promoting differentiation of Treg cells.

22. The method according to claim 1, wherein suppressing Th17 cell numbers comprises inhibiting Th17 cell differentiation.

23. The method according to claim 9, wherein the ratio of Th17 cells to Treg cells is reduced.

* * * * *